(12) United States Patent
Vandyck et al.

(10) Patent No.: US 9,126,986 B2
(45) Date of Patent: Sep. 8, 2015

(54) HETERO-BICYCLIC DERIVATIVES AS HCV INHIBITORS

(71) Applicant: Janssen R&D Ireland, Co Cork (IE)

(72) Inventors: Koen Vandyck, Paal-Beringen (BE); Wim Gaston Verschueren, Berchem (BE); Pierre Jean-Marie Bernard Raboisson, Rosieres (BE)

(73) Assignee: Janssen Sciences Ireland UC, Little Island, Co. Cork (IE)

( * ) Notice: Subject to any disclaimer, the term of this patent is extended or adjusted under 35 U.S.C. 154(b) by 0 days.

(21) Appl. No.: 14/368,335

(22) PCT Filed: Dec. 27, 2012

(86) PCT No.: PCT/EP2012/076934
§ 371 (c)(1),
(2) Date: Jun. 24, 2014

(87) PCT Pub. No.: WO2013/098313
PCT Pub. Date: Jul. 4, 2013

(65) Prior Publication Data
US 2014/0357626 A1 Dec. 4, 2014

(30) Foreign Application Priority Data
Dec. 28, 2011 (EP) .................................. 11195840

(51) Int. Cl.
| | | |
|---|---|---|
| *C07D 401/14* | (2006.01) | |
| *C07D 403/14* | (2006.01) | |
| *C07D 417/14* | (2006.01) | |
| *C07D 491/113* | (2006.01) | |
| *A61K 31/517* | (2006.01) | |
| *A61K 31/4709* | (2006.01) | |
| *A61K 31/438* | (2006.01) | |
| *A61K 31/5415* | (2006.01) | |
| *A61K 31/549* | (2006.01) | |
| *A61P 31/14* | (2006.01) | |
| *A61K 31/4412* | (2006.01) | |
| *A61K 31/513* | (2006.01) | |
| *A61K 31/527* | (2006.01) | |
| *C07D 491/10* | (2006.01) | |
| *A61K 31/506* | (2006.01) | |
| *A61K 45/06* | (2006.01) | |
| *C07D 491/107* | (2006.01) | |

(52) U.S. Cl.
CPC .......... *C07D 401/14* (2013.01); *A61K 31/4412* (2013.01); *A61K 31/4709* (2013.01); *A61K 31/506* (2013.01); *A61K 31/513* (2013.01); *A61K 31/517* (2013.01); *A61K 31/527* (2013.01); *A61K 31/549* (2013.01); *A61K 45/06* (2013.01); *C07D 403/14* (2013.01); *C07D 417/14* (2013.01); *C07D 491/10* (2013.01); *C07D 491/107* (2013.01); *C07D 491/113* (2013.01)

(58) Field of Classification Search
CPC ............. C07D 417/14; C07D 491/113; C07D 401/14; C07D 403/14; A61K 45/06; A61K 31/517; A61K 31/4709; A61K 31/435; A61K 31/5415; A61K 31/549
USPC ...................... 544/12, 51, 284; 546/122, 153; 514/223.2, 227.8, 266.23, 312
See application file for complete search history.

(56) References Cited

U.S. PATENT DOCUMENTS

| | | | |
|---|---|---|---|
| 5,807,876 | A | 9/1998 | Armistead et al. |
| 6,054,472 | A | 4/2000 | Armistead et al. |
| 6,344,465 | B1 | 2/2002 | Armistead et al. |
| 6,498,178 | B2 | 12/2002 | Stamos et al. |
| 7,704,992 | B2 | 4/2010 | Bachand et al. |
| 8,088,368 | B2 | 1/2012 | Guo et al. |

(Continued)

FOREIGN PATENT DOCUMENTS

| | | |
|---|---|---|
| FR | 2 900 404 A1 | 4/2006 |
| WO | 97/40028 A1 | 10/1997 |

(Continued)

OTHER PUBLICATIONS

Genelot et al., "*Optimised procedures for the one-pot selective syntheses of indoxyls and 4-quinolones by a carbonylative Sonogashira/cyclisation sequence*", Applied Catalysis, A: General 2009, 369, 1-2, 125-132.

(Continued)

*Primary Examiner* — Venkataraman Balasubramanian
(74) *Attorney, Agent, or Firm* — Andrea Jo Kamage

(57) ABSTRACT

Inhibitors of HCV replication of formula I, including stereochemically isomeric forms, and salts, hydrates, solvates thereof, wherein R and R' have the meaning as defined herein. The present invention also relates to processes for preparing said compounds, pharmaceutical compositions containing them and their use, alone or in combination with other HCV inhibitors, in HCV therapy.

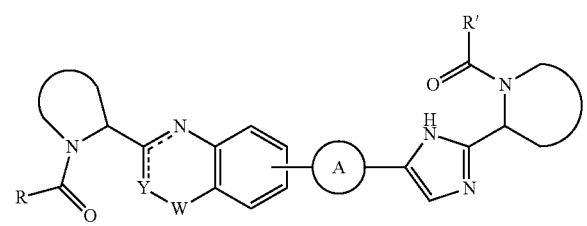

14 Claims, No Drawings

(56) References Cited

U.S. PATENT DOCUMENTS

| | | | |
|---|---|---|---|
| 8,101,643 B2 | 1/2012 | Qiu et al. | |
| 8,188,133 B2 | 5/2012 | Liberatore et al. | |
| 8,273,341 B2 | 9/2012 | Guo et al. | |
| 8,815,849 B2 * | 8/2014 | Vandyck et al. | 514/223.2 |
| 2011/0064698 A1 | 3/2011 | Or et al. | |

FOREIGN PATENT DOCUMENTS

| | | |
|---|---|---|
| WO | 98/40381 A1 | 9/1998 |
| WO | 00/56331 A1 | 9/2000 |
| WO | 2000/57877 A1 | 10/2000 |
| WO | 02/18369 A2 | 3/2002 |
| WO | 03/003727 A1 | 1/2003 |
| WO | 2004/000830 A1 | 12/2003 |
| WO | 2004/005264 A2 | 1/2004 |
| WO | 2004/050035 A2 | 6/2004 |
| WO | WO 2006/133326 A1 | 12/2006 |
| WO | 2007/000706 A2 | 1/2007 |
| WO | 2007/014927 A2 | 2/2007 |
| WO | 2007/039578 A1 | 4/2007 |
| WO | WO 2007039578 A1 | 4/2007 |
| WO | 2007/071434 A1 | 6/2007 |
| WO | 2007/073195 A1 | 6/2007 |
| WO | 2007/117692 A2 | 10/2007 |
| WO | 2008/021936 A2 | 2/2008 |
| WO | WO 2008/021927 A2 | 2/2008 |
| WO | WO 2008/021928 A2 | 2/2008 |
| WO | WO 2008/048589 A2 | 4/2008 |
| WO | WO 2008/070447 A2 | 6/2008 |
| WO | 2008/125599 A1 | 10/2008 |
| WO | 2009/102318 A1 | 8/2009 |
| WO | 2009/102325 A1 | 8/2009 |
| WO | WO 2010/017401 A1 | 2/2010 |
| WO | 2010/065674 A1 | 6/2010 |
| WO | WO 2010/065668 A1 | 6/2010 |
| WO | WO 2010/065681 A1 | 6/2010 |
| WO | 2010/091413 A1 | 8/2010 |
| WO | 2010/096302 A1 | 8/2010 |
| WO | 2010/099527 A1 | 9/2010 |
| WO | 2010/117635 A1 | 10/2010 |
| WO | 2010/132601 A1 | 11/2010 |
| WO | 2011/009084 A2 | 1/2011 |
| WO | WO 2011/119860 A1 | 9/2011 |
| WO | 2012/013643 A1 | 2/2012 |

OTHER PUBLICATIONS

Kumar et al., "*Simple and chemoselective reduction of aromatic nitro compounds to aromatic amines: reduction with hydriodic acid revisited*", Tetrahedron Letters, 2001, 42, 33, 5601-5603.

Lohmann et al., "*Replication of Subgenomic Hepatitis C Virus RNAs in a Hepatoma Cell Line*" 1999, Science, 285:110-113.

Kreiger et al., "*Enhancement of Hepatitis C Virus RNA Replication by Cell Culture-Adaptive Mutations*", (2001) Journal of Virology 75: 4614-4624.

Lohmann et al., "*Viral and Cellular Determinants of Hepatitis C Virus RNA Replication in Cell Culture*", (2003) Journal of Virology 77: 3007-3019.

Yi et al., "*Adaptive Mutations Producing Efficient Replication of Genotype 1a Hepatitis C Virus RNA in Normal Huh7 Cells*", (2004) Journal of Virology 78: 7904-7915.

Akira Matsuda et al., "*Radical Deoxygenation of Tert-Alcohols in 2'-Branched-Chain Sugar Pryimidine Nucleosides: Synthesis and Antileukemic Activity of 2'-Deoxy-2' (S)-Methylcytidine*", Chem Pharm Bull., vol. 35, No. 9, pp. 3967-3970 (1987).

Bodansky, Peptide Chemistry, $2^{nd}$ rev. ed. Spring-Verlag, Berlin, Germany (Table of Contents) (1993).

Eisuke Murakami et al., "*Mechanism of Activation of β-D-2'-Deoxy-2'-Fluoro-2'-Methylcytidine and Inhibition of Hepatitis C Virus NS5B RNA Polymerase*", Antimicrobial Agents and Chemotherapy, vol. 51, No. 2, pp. 503-509 (2007).

Hirokazu Awano et al., "*Synthesis and Antiviral Activity of 5-Substituted (2's)-2'-Deoxy-2'-C-Methylcytidines and—uridines*", Arch. Pharm. Med. Chem. 329, pp. 66-72 (1996).

Klaus Klumpp, et al. "*2'-Deoxy-4'-azido Nucleoside Analogs Are Highly Potent Inhibitors of Hepatitis C Virus Replication Despite the Lack of 2'-α-Hydroxyl Groups*", The Journal of Biological Chemistry, vol. 283, pp. 2167-2175 (2008).

L. W. Brox, et al., "*Studies on the Growth Inhibition and Metabolism of 2'-Deoxy-2'-fluorocytidine in Cultured Human Lymphoblasts*", Cancer Research, vol. 34., pp. 1838-1842 (1974).

Lars Petter Jordheim, et al., "*Advances in the Development of Nucleoside and Nucleotide Analogues for Cancer and Viral Diseases*", Nature Reviews, Drug Discovery, vol. 12, pp. 447-464 (2013).

Li et al., "*Identification of 1-isopropylsulfonyl-2-amine benzimidazoles as a new class of inhibitors of hepatitis B virus*", European Journal of Medicinal Chemistry 42(11-12):1358-1364 (2007).

M. A. Ivanov, et al., "*Synthesis and Biological Properties of Pyrimidine 4'-Fluoronucleosides and 4'-Fluorouridine 5'-O-Triphosphate*", Russian Journal of Bioorganic Chemistry, vol. 36, No. 4, pp. 488-496 (2010).

Michael J. Sofia, et al., "*Discovery of a β-D-2'-Deoxy-2'-α fluoro-2'-β-C-methyluridine Nucleotide Prodrug (PSI-7977) for the Treatment of Hepatitis C Virus*", Journal of Medicinal Chemistry, vol. 53, pp. 7202-7218 (2010).

Michael J. Sofia, et al., "*Nucleoside, Nucleotide, and Non-Nucleoside Inhibitors of Hepatitis C Virus NS5B RNA-Dependent RNA-Polymerase*", Journal of Medicinal Chemistry, vol. 55, pp. 2481-2531 (2012).

Peng Liu, et al., "*Fluorinated Nucleosides: Synthesis and Biological Implication*", J Fluor Chem., 129 (9), pp. 743-766 (2008).

Ciapetti et al., "*Molecular Variations Based on Isosteric Replacements*" The practice of Medical Chemistry (3rd edition), Chapter 15 pp. 290-342 (2008).

Wallen, Erik A., "*Dicarboxylic Acid bis(L-Prolyl-pyrrolidine) Amides as prolyl Oligopeptidase Inhibitors*", J. Med. Chem 45 pp. 1581-4584 (2002).

* cited by examiner

HETERO-BICYCLIC DERIVATIVES AS HCV INHIBITORS

CROSS-REFERENCE TO RELATED APPLICATIONS

This application claims the benefit of International Application Number PCT/EP2012/076934, filed 27 Dec. 2012, which claims the benefit of Application Number EP11195840.1, filed 28 Dec. 2011. The entire contents of each of the aforesaid applications are incorporated herein by reference in their entirety.

TECHNICAL FIELD

This invention relates to hetero-bicyclic derivatives, in particular, but not limited to quinolinone and quinazolinone derivatives, which are inhibitors of the hepatitis C virus (HCV), their synthesis and their use, alone or in combination with other HCV inhibitors, in the treatment or prophylaxis of HCV.

BACKGROUND ART

HCV is a single stranded, positive-sense RNA virus belonging to the Flaviviridae family of viruses in the hepacivirus genus. The viral genome translates into a single open reading frame that encodes for multiple structural and non-structural proteins.

Following the initial acute infection, a majority of infected individuals develop chronic hepatitis because HCV replicates preferentially in hepatocytes but is not directly cytopathic. In particular, the lack of a vigorous T-lymphocyte response and the high propensity of the virus to mutate appear to promote a high rate of chronic infection. Chronic hepatitis can progress to liver fibrosis, leading to cirrhosis, end-stage liver disease, and HCC (hepatocellular carcinoma), making it the leading cause of liver transplantations.

There are six major HCV genotypes and more than 50 subtypes, which are differently distributed geographically. HCV genotype 1 is the predominant genotype in Europe and in the US. The extensive genetic heterogeneity of HCV has important diagnostic and clinical implications, perhaps explaining difficulties in vaccine development and the lack of response to current therapy.

Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades.

Current HCV therapies are based on (pegylated) interferon-alpha (IFN-α) in combination with ribavirin. This combination therapy yields a sustained virologic response in 40% of patients infected by genotype 1 HCV and about 80% of those infected by genotypes 2 and 3. Beside the limited efficacy on HCV genotype 1, this combination therapy has significant side effects including influenza-like symptoms, hematologic abnormalities, and neuropsychiatric symptoms. Hence there is a need for more effective, more convenient and better-tolerated treatments.

Experience with HIV drugs, in particular with HIV protease inhibitors, has taught that sub-optimal pharmacokinetics and complex dosing regimens quickly result in inadvertent compliance failures. This in turn means that the 24 hour trough concentration (minimum plasma concentration) for the respective drugs in an HIV regime frequently falls below the $IC_{90}$ or $ED_{90}$ threshold for large parts of the day. It is considered that a 24 hour trough level of at least the $IC_{50}$, and more realistically, the $IC_{90}$ or $ED_{90}$, is essential to slow down the development of drug escape mutants. Achieving the pharmacokinetics and rate of drug metabolism necessary to allow such trough levels provides a stringent challenge to drug design.

The NS5A protein of HCV is located downstream of the NS4B protein and upstream of the NS5B protein. Upon post-translational cleavage by the viral serine protease NS3/4A, the NS5A matures into a zinc containing, three-domain phosphoprotein that either exists as a hypophosphorylated (56-kDa, p56) or hyperphosphorylated species (58-kDa, p58). NS5A of HCV is implicated in multiple aspects of the viral lifecycle including viral replication and infectious particle assembly as well as modulation of the environment of its host cell. Although no enzymatic function has been ascribed to the protein it is reported to interact with numerous viral and cellular factors.

A number of patents and patent applications disclose compounds with HCV inhibitory activity, in particular targeting NS5A. WO2006/133326 discloses stilbene derivatives while WO 2008/021927 and WO 2008/021928 disclose biphenyl derivatives having NS5A HCV inhibitory activity. WO 2008/048589 discloses 4-(phenylethynyl)-1H-pyrazole derivatives and their antiviral use. WO 2008/070447 discloses a broad range of HCV inhibiting compounds including a benzimidazole moiety. WO-2010/017401 and WO-2010/065681 both disclose bis-imidazole inhibitors of HCV NS5A.

There is a need for HCV inhibitors that may overcome the disadvantages of current HCV therapy such as side effects, limited efficacy, the emerging of resistance, and compliance failures, as well as improve the sustained viral load response.

The present invention concerns a group of HCV inhibiting hetero-bicyclic derivatives, in particular, but not limited to quinolinone and quinazolinone derivatives, with useful properties regarding one or more of the following parameters: antiviral efficacy, favorable profile of resistance development, reduced or lack of toxicity and genotoxicity, favorable pharmacokinetics and pharmacodynamics, ease of formulation and administration, and limited or lack of drug-drug interactions with other drug substances, in particular other anti-HCV agents.

Compounds of the invention may also be attractive due to the fact that they lack activity against other viruses, in particular against HIV. HIV infected patients often suffer from co-infections such as HCV. Treatment of such patients with an HCV inhibitor that also inhibits HIV may lead to the emergence of resistant HIV strains.

DESCRIPTION OF THE INVENTION

In one aspect, the present invention provides compounds of Formula I

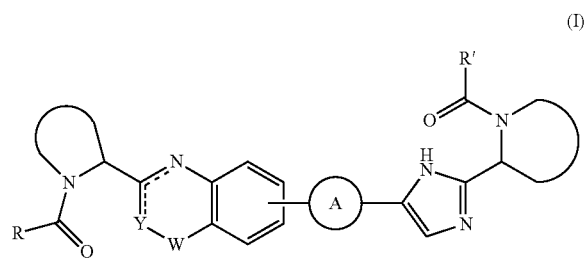

(I)

or a stereoisomer thereof, wherein:
Y is CH or N, CR$_4$;
W is carbonyl, sulfonyl or CR$_5$R$_6$;

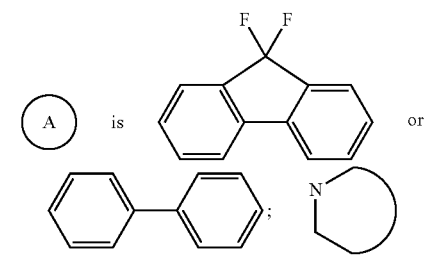

independently is selected from a group comprising

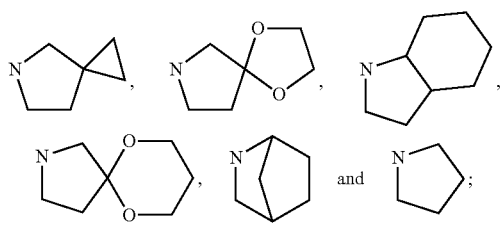

R and R' are independently selected from —CR$_1$R$_2$R$_3$, aryl optionally substituted with 1 or 2 substituents selected from halo and methyl, or heterocycloalkyl, wherein
- R$_1$ is selected from C$_{1-4}$alkyl, C$_{2-4}$alkyl substituted with methoxy or hydroxyl, and phenyl optionally substituted with 1 or 2 substituents independently selected from halo and methyl;
- R$_2$ is hydroxyl, amino, mono- or di-C$_{1-4}$alkylamino, C$_{1-4}$alkyl-carbonylamino, C$_{1-4}$alkyloxycarbonylamino;
- R$_3$ is hydrogen or C$_{1-4}$alkyl;
- R$_4$ is hydrogen, C$_{1-4}$alkyl or Fluoro;
- R$_5$ and R$_6$, each independently, are C$_{1-4}$alkyl; or CR$_5$R$_6$ together form C$_{3-7}$cycloalkyl, oxetane, tetrahydrofurane;

or a pharmaceutically acceptable salts or a solvate thereof.

Additionally, the invention relates to a product containing (a) a compound according to the present invention, and (b) another HCV inhibitor, as a combined preparation for simultaneous, separate or sequential use in the treatment of HCV infections.

In a further aspect, the invention concerns the use of compounds of formula Ia-c, or subgroups thereof, as specified herein, for inhibiting HCV. Alternatively, there is provided the use of said compounds for the manufacture of a medicament for inhibiting HCV.

In a first embodiment, the present invention provides a subgroup of compounds of formula I, which can be represented by the formula (Ia);

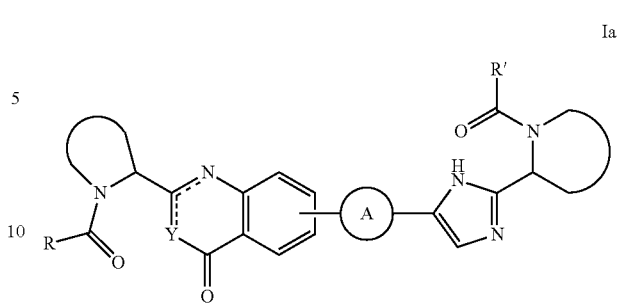

Of particular interest are compounds of formula I or subgroups thereof as defined herein, that are according to formula Ib and Ic.

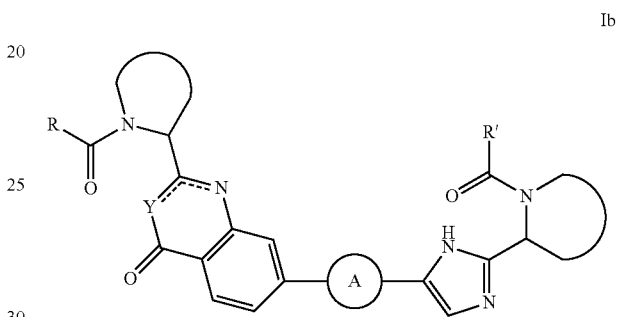

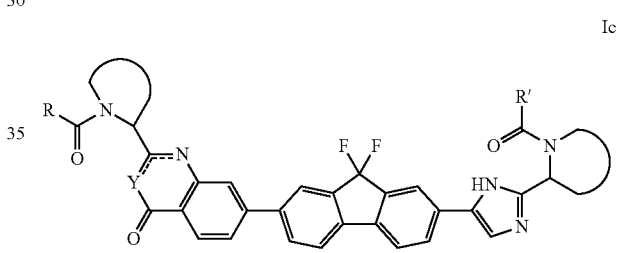

In a preferred embodiment,

independently is selected from a group comprising

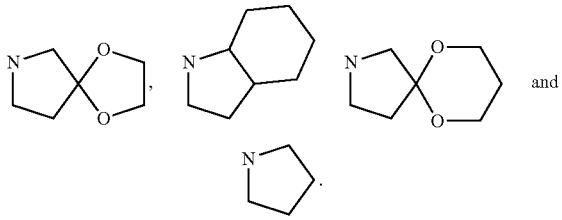

Preferably, at least one

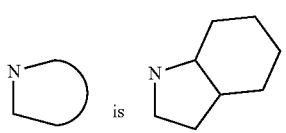

More preferably compounds of the invention provides compounds which can be represented by the formula Id

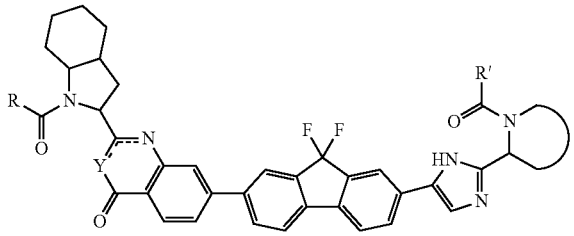

Id

In a further embodiment of the invention, $R_2$ selected from the group comprising $C_{1-4}$alkylcarbonylamino or $C_{1-4}$alkyloxycarbonylamino.

In yet another embodiment of the invention, $R_1$ is selected from branched $C_{3-4}$alkyl; $C_{2-3}$alkyl substituted with methoxy; and phenyl optionally substituted with 1 substituent selected from halo and methyl.

In yet another embodiment of the invention, $R_3$ is hydrogen.

In a further embodiment R and R' are identical.

In yet a further embodiment $R_2$ is $C_{1-4}$alkylcarbonylamino or $C_{1-4}$alkyloxycarbonylamino, and $R^3$ is hydrogen.

In a further aspect, the invention provides a compound of formula I or a pharmaceutically acceptable salt, hydrate, or solvate thereof, for use in the treatment or prophylaxis (or the manufacture of a medicament for the treatment or prophylaxis) of HCV infection. Representative HCV genotypes in the context of treatment or prophylaxis in accordance with the invention include but are not limited to genotype 1b (prevalent in Europe) and 1a (prevalent in North America). The invention also provides a method for the treatment or prophylaxis of HCV infection, in particular of the genotype 1a or 1b, comprising administering to a subject in need thereof, a therapeutically effective amount of a compound as defined hereinbefore.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms or stereoisomers of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphorsulfonic acid. Alternatively, enantiomers may be separated by chromatographic techniques using chiral stationary phases. Said pure stereochemically isomeric forms may also be derived from the corresponding pure stereoisomeric forms of the appropriate starting materials, provided that the reaction occurs stereospecifically. Preferably, if a specific stereoisomer is desired, said compound is synthesized by stereospecific methods of preparation. These methods will advantageously employ enantiomerically pure starting materials.

The diastereomeric racemates of the compounds of formula I can be obtained separately by conventional methods. Appropriate physical separation methods that may advantageously be employed are, for example, selective crystallization and chromatography, e.g. column chromatography or supercritical fluid chromatography.

The compounds of formula I and subgroups of compounds of formula I as defined hereinbefore have several centers of chirality. Of interest are the stereogenic centers of the pyrrolidine ring at the 2-carbon atom. The configuration at this position may be that corresponding to L-proline, i.e.

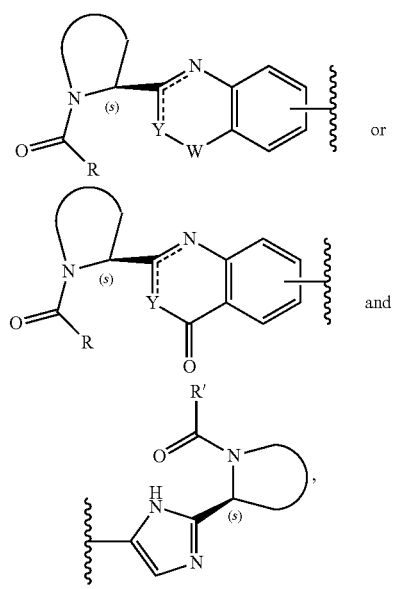

or that corresponding to D-proline, i.e.

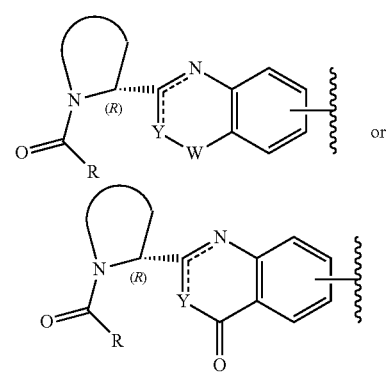

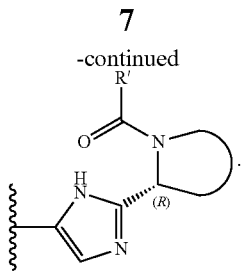

Also of interest is the configuration of the group —CR$_1$R$_2$R$_3$ wherein R$_3$ is H: when R$_1$ is selected from branched C$_{3-4}$alkyl; C$_{2-3}$alkyl substituted with methoxy, then the S-configuration is preferred; when R$_1$ is selected from phenyl optionally substituted with 1 or 2 substituents independently selected from halo and methyl; then the R-configuration is preferred.

The pharmaceutically acceptable addition salts comprise the therapeutically active non-toxic acid and base addition salt forms of the compounds of formula (I) or subgroups thereof. Of interest are the free, i.e. non-salt forms of the compounds of formula I, or of any subgroup of compounds of formula I specified herein.

The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propionic, hydroxyacetic, lactic, pyruvic, oxalic (i.e. ethanedioic), malonic, succinic (i.e. butanedioic acid), maleic, fumaric, malic (i.e. hydroxyl-butanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of formula (I) containing an acidic proton may also be converted into their base addition salts, in particular metal or amine addition salt forms, by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "solvates" covers any pharmaceutically acceptable solvates that the compounds of formula I as well as the salts thereof, are able to form. Such solvates are for example hydrates, alcoholates, e.g. ethanolates, propanolates, and the like.

Some of the compounds of formula I may also exist in tautomeric forms. For example, tautomeric forms of amide (—C(═O)—NH—) groups are iminoalcohols (—C(OH)═N—). Tautomeric forms, although not explicitly indicated in the structural formulae represented herein, are intended to be included within the scope of the present invention.

As used herein, "C$_{1-4}$alkyl" as a group or part of a group defines saturated straight or branched chain hydrocarbon groups having from 1 to 4 carbon atoms such as for example methyl, ethyl, 1-propyl, 2-propyl, 1-butyl, 2-butyl, 2-methyl-1-propyl, 2-methyl-2-propyl. For the purpose of the present invention, of interest amongst C$_{1-4}$alkyl is C$_{3-4}$alkyl, i.e. straight or branched chain hydrocarbon groups having 3 or 4 carbon atoms such as 1-propyl, 2-propyl, 1-butyl, 2-butyl, 2-methyl-1-propyl, 2-methyl-2-propyl. Of particular interest may be branched C$_{3-4}$alkyl such as 2-propyl, 2-butyl, 2-methyl-1-propyl, 2-methyl-2-propyl.

The term "C$_{3-6}$cycloalkyl" as a group or part thereof, defines saturated cyclic hydrocarbon groups having from 3 to 6 carbon atoms that together form a cyclic structure. Examples of C$_{3-6}$cycloalkyl include cyclopropyl, cyclobutyl, cyclopentyl and cyclohexyl.

"C$_{1-4}$alkoxy" as a group or part of a group means a group of formula —O—C$_{1-4}$alkyl wherein C$_{1-4}$alkyl is as defined above. Examples of C$_{1-4}$alkoxy are methoxy, ethoxy, n-propoxy, isopropoxy.

The term "halo" is generic to fluoro, chloro, bromo and iodo.

As used herein, the term "(═O)" or "oxo" forms a carbonyl moiety when attached to a carbon atom. It should be noted that an atom can only be substituted with an oxo group when the valency of that atom so permits.

As used herein for the purpose of defining "aryl" as a group or part thereof means an aromatic ring structure optionally comprising one or two heteroatoms selected from N, O and S, in particular from N and O. Said aromatic ring structure may have 5 or 6 ring atoms.

As used herein, the prefix "hetero-" in the definition of a group means that the group comprises at least 1 heteroatom selected from N, O and S, in particular N and O. For example, the term "heteroaryl" means an aromatic ring structure as defined for the term "aryl" comprising at least 1 heteroatom selected from N, O and S, in particular from N and O, for example furanyl, oxazolyl, pyridinyl. Alternatively, the term "heteroC$_{3-6}$cycloalkyl" means saturated cyclic hydrocarbon group as defined for "C$_{3-6}$cycloalkyl" further comprising at least 1 heteroatom selected from N, O and S, in particular from N and O, for example tetrahydrofuranyl, tetrahydropyranyl, piperidinyl.

Where the position of a group on a molecular moiety is not specified (for example a substituent on phenyl) or is represented by a floating bond, such group may be positioned on any atom of such a moiety, as long as the resulting structure is chemically stable. When any variable is present more than once in the molecule, each definition is independent.

Whenever used herein, the term "compounds of formula I", or "the present compounds" or similar terms, it is meant to include the compounds of formula I, including the possible stereoisomeric forms, and the pharmaceutically acceptable salts and solvates thereof.

General Synthetic Methods

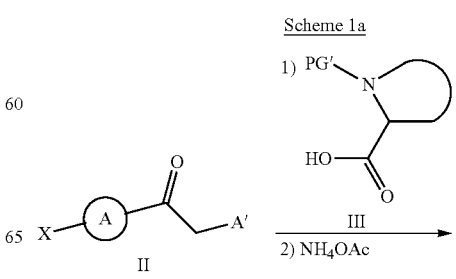

Scheme 1a

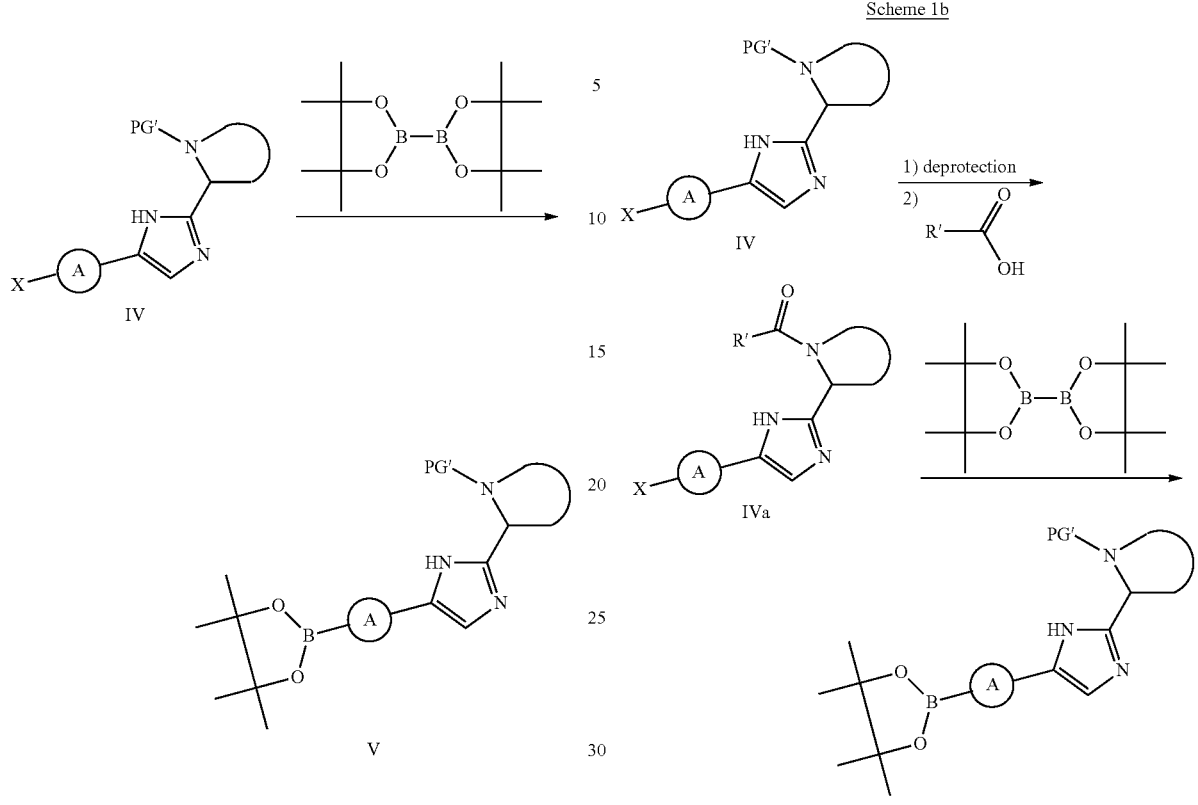

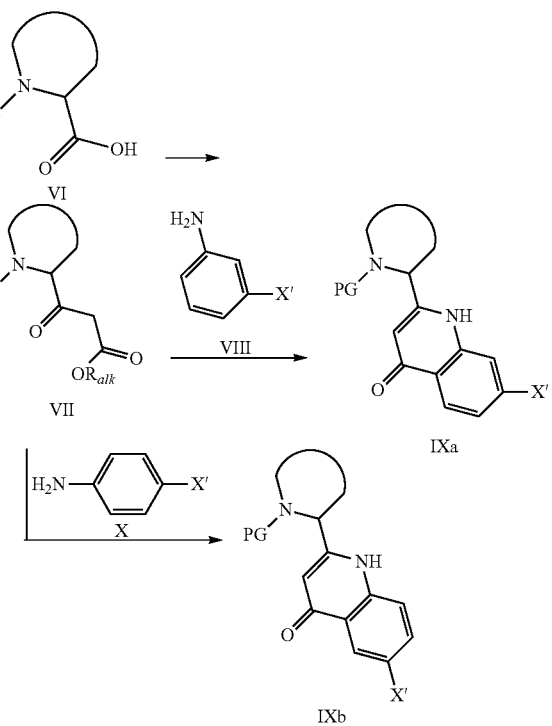

Building blocks used in the synthesis of compounds of formula I are described in scheme 1. α-Amino ketone IIa (Scheme 1, A'=NH$_2$), with X a halogen, in particular bromo or iodo, is coupled with a suitably protected derivative III, wherein PG' is a protective group on the nitrogen, preferably tert-butoxycarbonyl, in the presence of a coupling reagent for amino-group acylation, preferably HATU, in the presence of a base such as DIPEA. The thus formed intermediate is cyclized to an imidazole compound of general formula IV by treatment with ammonium acetate, preferably at a temperature ranging between 0° C. and 150° C.

Alternatively, the intermediate imidazole IV can be obtained by coupling an α-halo ketone IIb wherein X and A' each independently represent a halo atom, X preferably selected from iodo or bromo and A' preferably selected from chloro, bromo or iodo, with a suitably protected compound III wherein PG' is a protective group on the nitrogen, preferably tert-butoxycarbonyl, in the presence of a suitable base, for example DIPEA, followed by cyclization to the imidazole intermediate IV as described above. This intermediate IV can be transformed to a boronic ester of formula V under Pd catalyzed conditions, for example in the presence of Pd(dppf)Cl$_2$, bis(pinacolato)diboron and a base, for example potassium acetate.

Similarly, compounds of formula IVa may be transformed to compounds of formula Va as depicted in scheme 1b. IVa can be obtained by removing the protecting group PG' (e.g. by using HCl in dioxane or TMSOTf/lutidine in CH$_2$Cl$_2$ in case PG' equals tert-butyloxycarbonyl), followed by coupling of the resulting amine with an acid of formula R'(CO)OH under typical amide bond formation conditions (e.g. by treatment with HATU or HBTU and a base like DIPEA or the use of EDCI/HOBt/DIPEA).

Other building blocks are described in schemes 2a, 2b, 2c and 3a, 3b, 3c, 3d, 3e.

In scheme 2a, the acid derivative VI is converted into an β-ketoester VII by methods known in literature, for example, by activation of the carboxylic acid with DCC or CDI, followed by, for example, reaction with Meldrum's acid and subsequent decarboxylation in the presence of an alcohol, or as an alternative by condensation with a monoalkyl malonate magnesium salt followed by decarboxylation. The β-ketoester VII ($R_{alk}$ referring to $C_{1-4}$alkyl) is then condensed with VIII or X, followed by cyclisation to IXa and IXb respectively (X' is a halogen selected from iodo or bromo, preferably bromo). This condensation can be performed in toluene in the presence of acetic acid. Cyclisation to the compounds of formula IXa and IXb, can be performed thermally by refluxing in Dowtherm™ A (blend of diphenyl oxide and biphenyl). A preferred example of the protecting group PG is benzyloxycarbonyl (CBz).

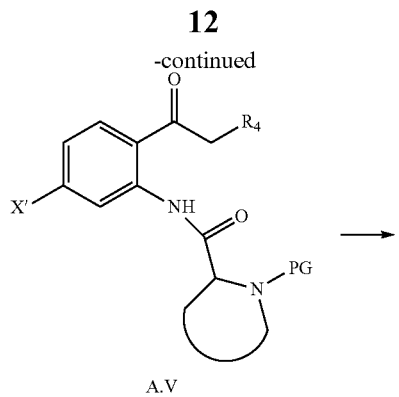

A.V

Scheme 2b

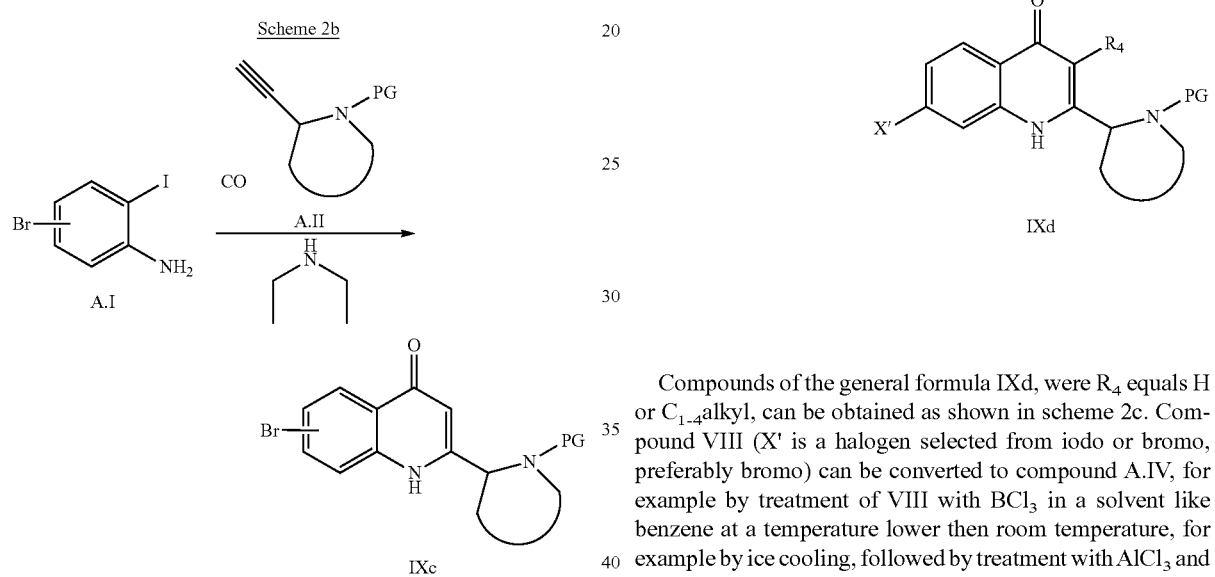

Alternatively, compounds of the general formula IXc can be obtained by a Pd catalyzed carbonylative Sonogashira/cyclization sequence as described in Scheme 2b.

Starting from iodo-aniline compound A.I, under procedures similar as described in *Applied Catalysis, A: General* 2009, 369, 1-2, 125-132 and references cited therein.

Scheme 2c

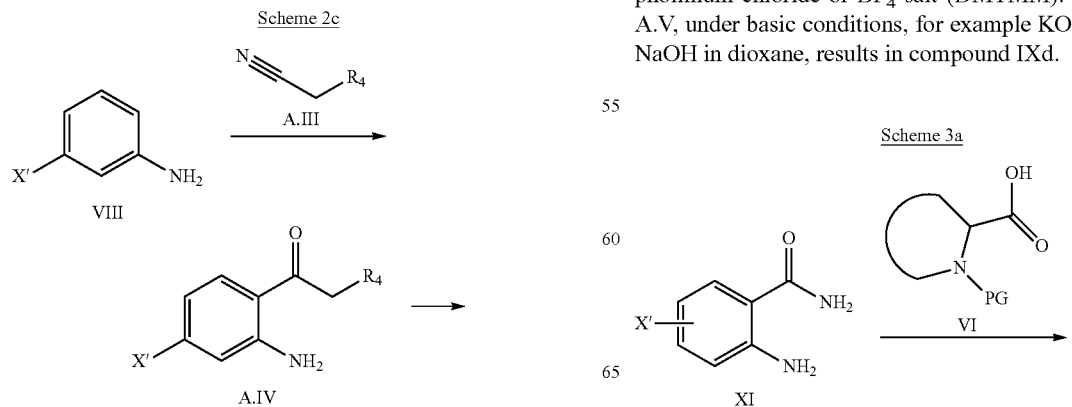

Compounds of the general formula IXd, were $R_4$ equals H or $C_{1-4}$alkyl, can be obtained as shown in scheme 2c. Compound VIII (X' is a halogen selected from iodo or bromo, preferably bromo) can be converted to compound A.IV, for example by treatment of VIII with $BCl_3$ in a solvent like benzene at a temperature lower then room temperature, for example by ice cooling, followed by treatment with $AlCl_3$ and nitrile A.III ($R_4$ equals H or $C_{1-4}$alkyl) for example at reflux in benzene. After hydrolysis, compound A.IV can be obtained. Amide bond formation starting from A.IV and VI results in the formation of compound A.V. This reaction can be effected by converting compound VI to an acid halogenide, for example an acid fluoride or acid chloride, followed by reaction with A.IV in the presence of a base. Another example is the formation of A.V from VI and A.IV by use of the coupling reagent 4-(4,6-Dimethoxy[1.3.5]triazin-2-yl)-4-methylmorpholinium chloride or $BF_4$ salt (DMTMM). Cyclisation of A.V, under basic conditions, for example KOH in EtOH, or NaOH in dioxane, results in compound IXd.

Scheme 3a

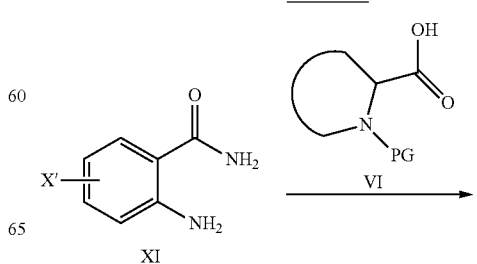

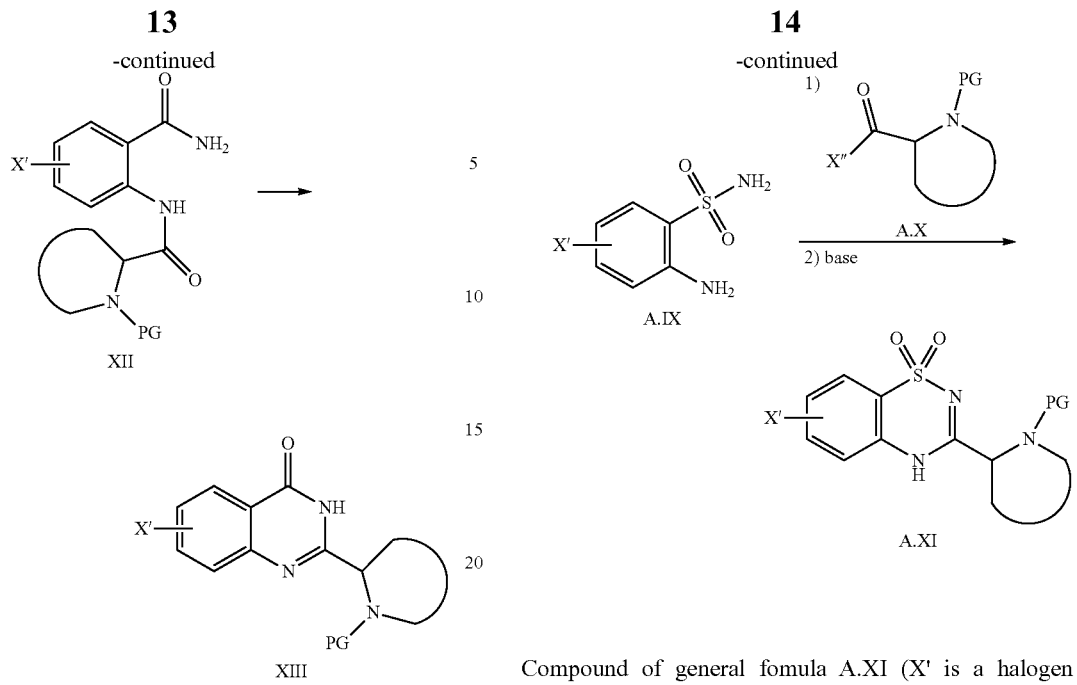

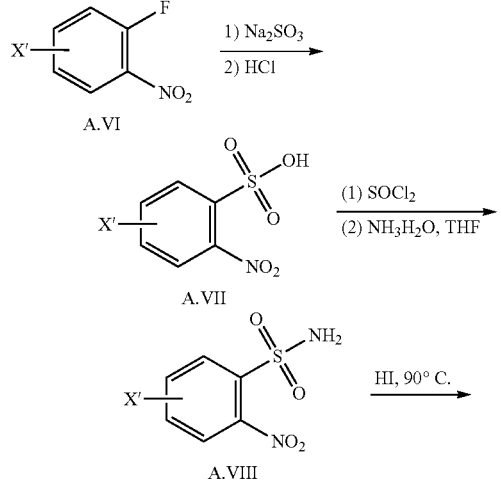

The synthesis of compounds of the formula XIII is described in Scheme 3a. Amide bond formation starting from XI (X' is a halogen selected from iodo or bromo, preferably bromo) and VI results in the formation of compound XII. This reaction can be effected by converting compound VI to an acid halogenide, for example an acid fluoride or acid chloride followed by reaction with XI in the presence of a base. Another example is the formation of XII from VI and XI by use of the coupling reagent 4-(4,6-Dimethoxy[1.3.5]triazin-2-yl)-4-methylmorpholinium chloride (DMTMM). Compounds XII are then converted to compounds of the general formula XIII under basic conditions, for example KOH or $Na_2CO_3$ in ethanol.

Compound of general fomula A.XI (X' is a halogen selected from iodo or bromo, preferably bromo) can be obtained as shown in scheme 3b. Using methods described in literature (WO2007039578; Tet. Lett. 2001, 42, 33, 5601-5603), fluoride A.VI can be converted to A.IX. The latter is coupled with and acid halogenide A.X (where X" equals chloro or fluoro) in the presence of a base, for example triethylamine, followed by cyclization to compound A.XI under basic conditions like for example 2N aqueous $K_2CO_3$ at reflux.

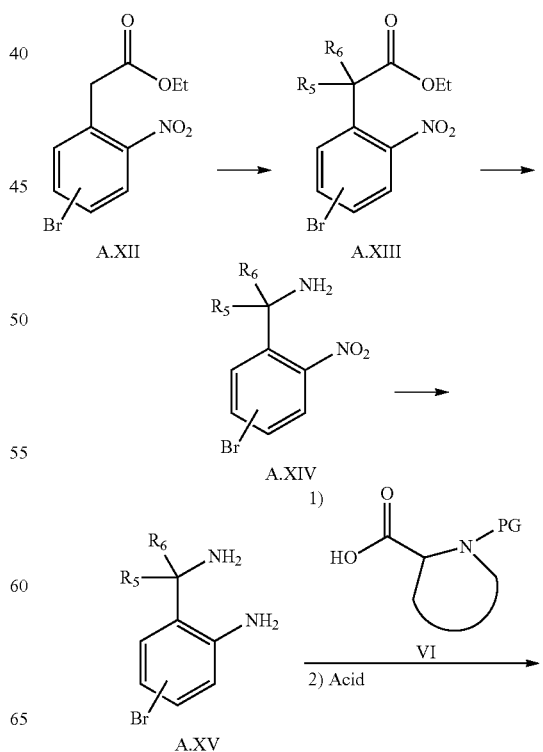

-continued

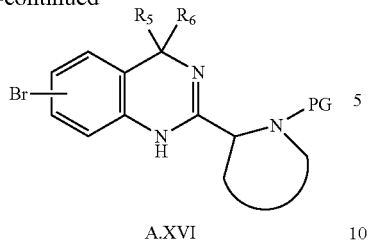

A.XVI

-continued

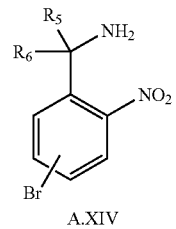

A.XIV

Compound of general fomula A.XVI can be obtained as shown in scheme 3c. Dialkylation of ester A.XII with the appropriate alkylhalogenide, for example MeI in the case $R_5=R_6=$Methyl, in the presence of a base, for example NaH, results in compound A.XIII. This ester can be converted to compound A.XIV by subsequent hydrolysis, acyl azide formation (for example by treatment of the corresponding acid of A.XIII with diphenylphosphoryl azide) and Curtius reaction. After reduction of compound A.XIV to A.XV, the latter compound is converted to compound A.XVI by coupling with acid VI, for example by treatement with HATU and a base like triethylamine, and subsequent cyclisation to compound A.XVI under acidic conditions, for example in acetic acid at 50° C.

An alternative procedure for the synthesis of compound A.XIV (for example in case $R_5$ and $R_6$ together with the carbon that connects them, form an oxetane) is depicted in scheme 3d. The anion, generated by transmetalation reaction of for example buthyl-lithium and compound A.XVII at low temperature, for example −78° C., can be reacted with a sulfineamide A.XVIII. After deprotection of the formed sulfineamide, under acidic conditions, compound A.XIV is obtained, which can be further transformed to A.XVI as described in Scheme 3c.

Scheme 4

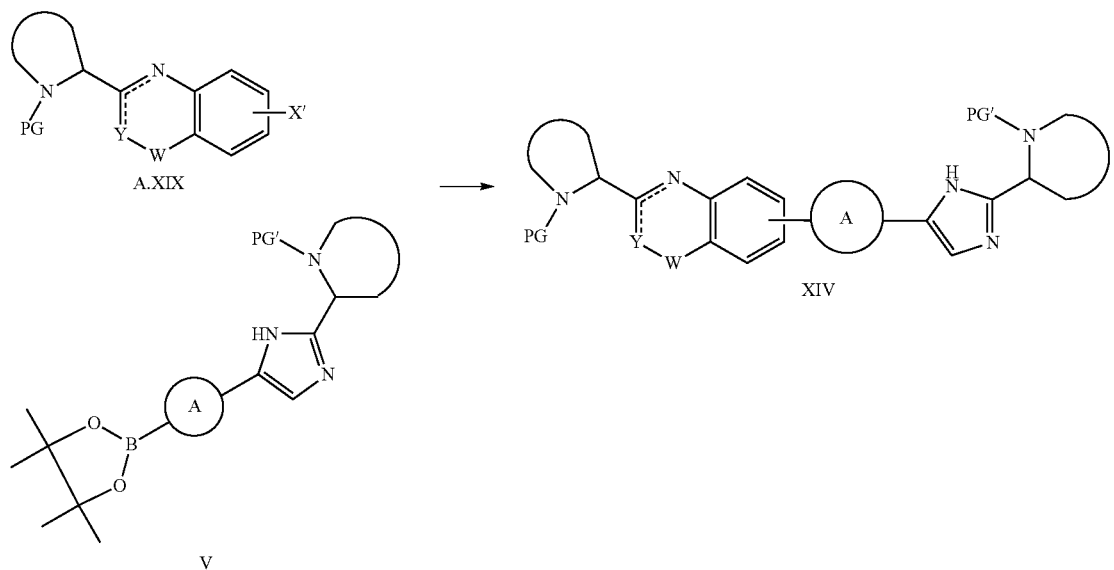

Scheme 3d

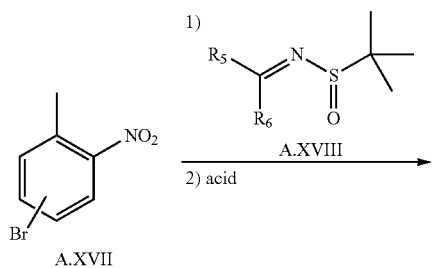

The building blocks A.XIX, obtained by methods similar as described in schemes 2 (a, b, c) and schemes 3 (a, b, c and d) and V (Scheme 1) can be converted to structure XIV, using Suzuki-Miyaura conditions (scheme 4). A similar Suzuki-Miyaura reaction can be performed when V is substituted by Va and/or A.XIX by A.XIXa, resulting in compounds with general formula XXI, XXIII or I. A.XIXa can be obtained from A.XIX by selectively removing the protecting group PG, (e.g. by using HCl in dioxane, TMSOTf/lutidine in $CH_2Cl_2$, or TFA in $CH_2Cl_2$ in case PG equals tert-butyloxycarbonyl or HBr in $HOAc/H_2O$ in case PG equals benzyloxycarbonyl), followed by coupling of the resulting amine with an acid of formula R(CO)OH under typical amide bond formation conditions (e.g. by treatment with HATU or HBTU and a base like DIPEA or the use of EDCI/HOBt/DIPEA) (scheme 3e).

Scheme 3e

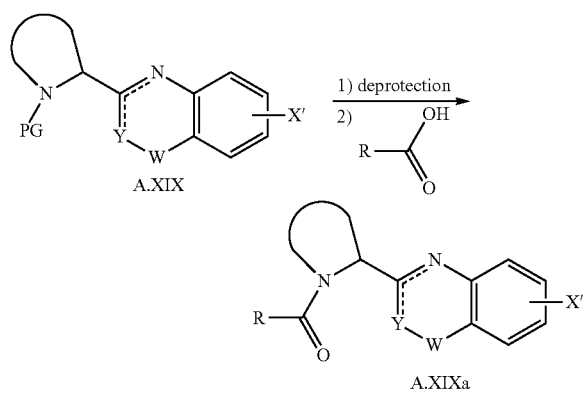

Scheme 5

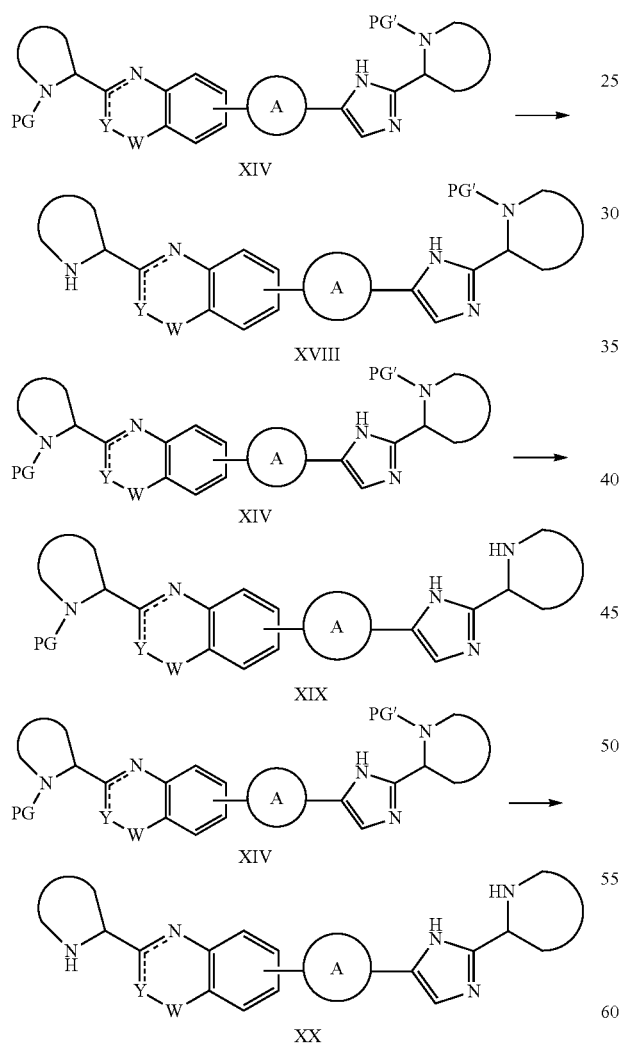

When PG' and PG in schemes 1 to 4 represent R'(C=O)— and R(C=O)— respectively, compounds of general structure XIV fall under the definition of compounds of formula I. In that case schemes 4 describes the synthesis of compounds of formula I. Alternatively, XIV can be deprotected as described in scheme 5. For example by treatment with acid (for example HCl in iPrOH) when PG or PG' represent tert butyloxycarbonyl (Boc). Compound XX can be transformed to a compound of formula Ie wherein R and R' are identical, by classical amide formation between an acid R—(C=O)OH and bisamine XX as described in scheme 6. Preferred methods are the use of HATU in the presence of a base like DIPEA, or HOBt in the presence of EDCI and NEt$_3$.

Scheme 6

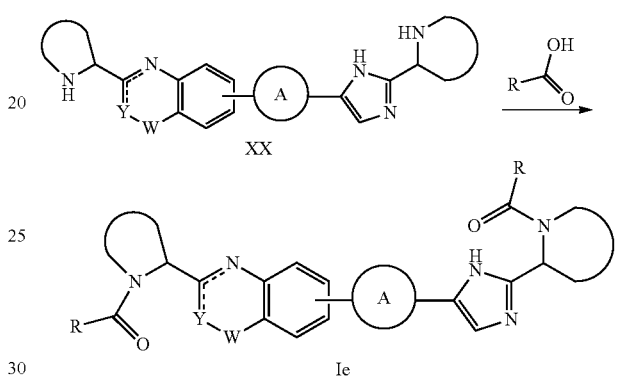

Where PG' differs from PG, selective deprotection is possible, as described in scheme 5, resulting in compounds XVIII or XIX starting from XIV. For example in case PG' equals tert-butyloxycarbonyl (Boc) and PG equals benzyloxycarbonyl (Cbz), selective deprotection can be effected by removing the Boc-protective group under acidic conditions like HCl in iPrOH at room temperature, or by removing the CBz-protective group under reducing conditions like hydrogen in the presence of a catalyst, e.g. Pd(OH)$_2$.

When PG' represents R'(C=O)— or PG represents R(C=O)—, the synthesis of compounds XIV as described in scheme 1 to 4 results in compounds of formula XXI (Scheme 7) or XXIII (Scheme 8) respectively. Compounds XXI and XXIII can be obtained from compound XIX and R'(C=O) OH or XVIII and R(C=O)OH respectively, under typical amide formation conditions. These compounds can then be transformed to compounds of formula I. Selective deprotection of XXI to XXII followed by amide bond formation between XXII and R(C=O)—OH results in compounds of the formula I. An analogous reaction sequence can then be applied to transform XXIII into XXIV and onwards to compounds of formula I.

Scheme 7

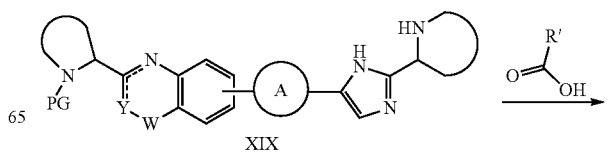

-continued

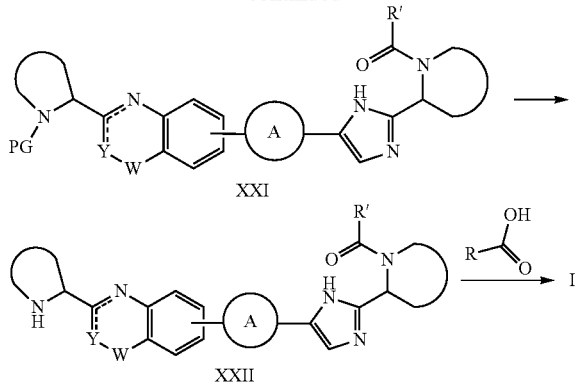

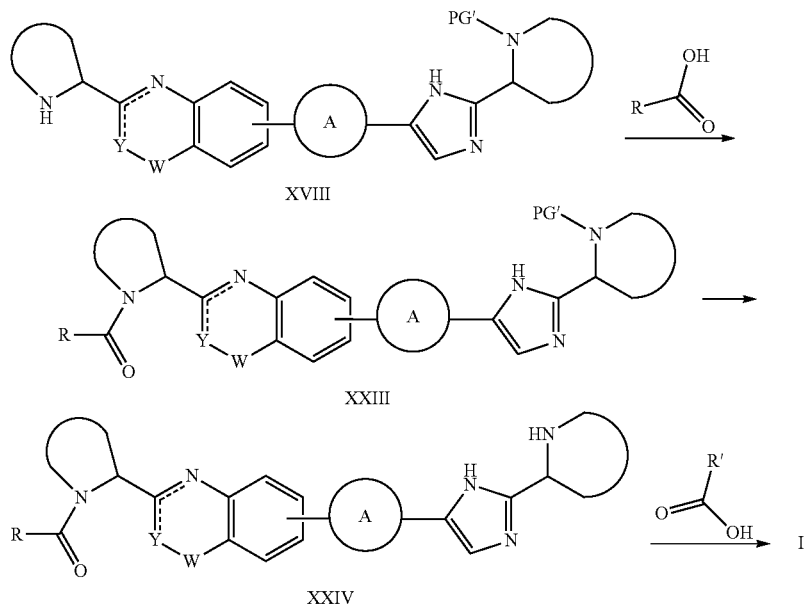

In a further aspect, the present invention concerns a pharmaceutical composition comprising a therapeutically effective amount of a compound of formula I as specified herein, and a pharmaceutically acceptable carrier. A therapeutically effective amount in this context is an amount sufficient to stabilize or to reduce HCV infection in infected subjects, or an amount sufficient to prevent HCV infection in subjects at risk of being infected. In still a further aspect, this invention relates to a process of preparing a pharmaceutical composition as specified herein, which comprises intimately mixing a pharmaceutically acceptable carrier with a therapeutically effective amount of a compound of formula I, as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula I show activity against HCV and can be used in the treatment and prophylaxis of HCV infection or diseases associated with HCV. The latter include progressive liver fibrosis, inflammation and necrosis leading to cirrhosis, end-stage liver disease, and hepatocellular carcinoma. A number of the compounds of this invention moreover are known to be active against mutated strains of HCV. Additionally, compounds of this invention may have attractive properties in terms of bioavailability, show a favorable pharmacokinetic profile, including an acceptable half-life, AUC (area under the curve), peak and trough values, and lack unfavorable phenomena such as insufficiently rapid onset or tissue retention.

The in vitro antiviral activity against HCV of the compounds of formula I can be tested in a cellular HCV replicon system based on Lohmann et al. (1999) Science 285:110-113, with the further modifications described by Krieger et al. (2001) Journal of Virology 75: 4614-4624 and Lohmann et al. (2003) Journal of Virology 77: 3007-3019 for genotype 1b and by Yi et al. (2004) Journal of Virology 78: 7904-7915 for genotype 1a (incorporated herein by reference), which is further exemplified in the examples section. This model, while not a complete infection model for HCV, is widely accepted as the most robust and efficient model of autonomous HCV RNA replication currently available. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

Due to their anti-HCV properties, the compounds of formula I or subgroups thereof, as specified herein, are useful in the inhibition of HCV replication, in particular in the treatment of warm-blooded animals, in particular humans, infected with HCV, and for the prophylaxis of HCV infections in warm-blooded animals, in particular humans. The present invention furthermore relates to a method of treating a warm-blooded animal, in particular a human, infected by HCV, or being at risk of infection by HCV, said method comprising the administration of a therapeutically or prophylactively effective amount of a compound of formula I, as defined hereinbefore.

The compounds of formula I as specified herein may therefore be used as a medicine, in particular as an anti-HCV medicine. Said use as a medicine or method of treatment comprises the systemic administration to HCV infected subjects or to subjects susceptible to HCV infection of an amount effective to relieve or prevent the symptoms and conditions associated with HCV infection.

The present invention also relates to the use of the present compounds in the manufacture of a medicament for the treatment or the prevention of HCV infection.

In general it is contemplated that an effective antiviral daily amount would be from about 0.01 to about 50 mg/kg, or about 0.02 to about 30 mg/kg body weight. It may be appropriate to administer the required dose as two, three, four or more sub-doses at appropriate intervals throughout the day. Said sub-doses may be formulated as unit dosage forms, for example, containing about 1 to about 500 mg, or about 1 to about 300 mg, or about 1 to about 100 mg, or about 2 to about 50 mg of active ingredient per unit dosage form.

Combination Therapy

The invention also relates to a combination of a compound of formula I, a pharmaceutically acceptable salt or solvate thereof, and another antiviral compound, in particular another anti-HCV compound. The term "combination" relates to a product containing (a) a compound of formula I, as defined hereinbefore, and (b) another anti-HCV inhibitor, as a combined preparation for simultaneous, separate or sequential use in the treatment of HCV infections.

The combinations of the present invention may be used as medicaments. Accordingly, the present invention relates to the use of a compound of formula (I) or any subgroup thereof as defined above for the manufacture of a medicament useful for inhibiting HCV activity in a mammal infected with HCV viruses, wherein said medicament is used in a combination therapy, said combination therapy in particular comprising a compound of formula (I) and at least one other anti-HCV agent, e.g. IFN-α, pegylated IFN-α, ribavirin, albuferon, taribavirin, nitazoxanide Debio025 or a combination thereof.

Other agents that may be combined with the compounds of the present invention include, for example, nucleoside and non-nucleoside inhibitors of the HCV polymerase, protease inhibitors, helicase inhibitors, NS4B inhibitors and agents that functionally inhibit the internal ribosomal entry site (IRES) and other agents that inhibit HCV cell attachment or virus entry, HCV RNA translation, HCV RNA transcription, replication or HCV maturation, assembly or virus release. Specific compounds in these classes include HCV protease inhibitors such as telaprevir (VX-950), boceprevir (SCH-503034), narlaprevir (SCH-900518), ITMN-191 (R-7227), TMC-435350 (TMC-435), MK-7009, BI-201335, BI-2061 (ciluprevir), BMS-650032, ACH-1625, ACH-1095, GS 9256, VX-985, IDX-375, VX-500, VX-813, PHX-1766, PHX2054, IDX-136, IDX-316, ABT-450, EP-013420 (and congeners) and VBY-376; the nucleoside HCV polymerase inhibitors useful in the invention include TMC649128, R7128, PSI-7851, PSI 7977, INX-189,IDX-184, IDX-102, R1479, UNX-08189, PSI-6130, PSI-938 and PSI-879 and various other nucleoside and nucleotide analogs and HCV inhibitors including those derived as 2'-C-methyl modified nucleosides, 4'-aza modified nucleosides, and 7'-deaza modified nucleosides. Non-nucleoside HCV polymerase inhibitors useful in the invention include HCV-796, HCV-371, VCH-759, VCH-916, VCH-222, ANA-598, MK-3281, ABT-333, ABT-072, PF-00868554, BI-207127, GS-9190, A-837093, JKT-109, GL-59728, GL-60667, ABT-072, AZD-2795 and TMC647055.

The following examples are meant to illustrate the invention and should not be construed as a limitation of its scope.

EXPERIMENTAL PART

LCMS Methods

Method A: General: mobile phase A: H$_2$O (0.1% TFA; B: CH$_3$CN (0.05% TFA) Stop Time: 2 min; gradient time (min) [% A/% B] 0.01 [90/10] to 0.9 [20/80] to 1.5[20/80] to 1.51 [90/10]; flow: 1.2 mL/min; column temp.: 50° C.

Method A1: Shimadzu LCMS 2010, Shim-pack XR-ODS, 3*30 mm

Method A2: Xtimate C18 2.1*30 mm, 3 um

Method A3: SHIMADZU Shim pack 2*30

Method B: Agilent 1100, YMC-PACK ODS-AQ, 50×2.0 mm 5 μm mobile phase A: H$_2$O (0.1% TFA; B: CH$_3$CN (0.05% TFA Stop Time: 10 min; gradient time(min) [% A/% B] 0 [100/0] to 1 [100/0] to 5[40/60] to 7.5 [40/60] to 8 [100/0]; flow: 0.8 mL/min; column temp.: 50° C.

Method C: Agilent 1100, YMC-PACK ODS-AQ, 50×2.0 mm 5 μm mobile phase A: H$_2$O (0.1% TFA; B: CH$_3$CN (0.05% TFA); Stop Time: 10 min; gradient time(min) [% A/% B] 0 [90/10] to 0.8 [90/10] to 4.5[20/80] to 7.5 [20/80] to 8 [90/10]; flow: 0.8 mL/min; column temp.: 50° C.

Method D: Shimadzu LCMS 2010, Shim-pack XR-ODS, 3*30 mm, mobile phase A: H$_2$O (0.1% TFA; B: CH$_3$CN (0.05% TFA) Stop Time: 2 min; gradient time(min) [% A/% B] 0.01 [100/0] to 0.9 [70/30] to 1.5[70/30] to 1.51 [100/0]; flow: 1.2 mL/min; column temp.: 50° C.

Method E: Liquid Chromatography: Waters Alliance 2695, UV detector: Waters 996 PDA, range: 210-400 nm; Mass detector: Waters ZQ, ion source: ES+, ES− Column used: SunFire C18 3.5μ 4.6×100 mm mobile phase A: 10 mM NH$_4$OOCH+0.1% HCOOH in H$_2$O; mobile phase B: CH$_3$OH; column temp.: 50° C.; flow: 1.5 mL/min. gradient time(min) [% A/% B] 0 [65/35] to 7[5/95] to 9.6[5/95] to 9.8[65/35] to 12 [65/35].

Method F: Xtimate C18 2.1*30 mm, 3 um, mobile phase A: H$_2$O (1.5 mL TFA/4 L); B: CH$_3$CN (0.75 mL TFA/4 L) Stop Time: 3 min; gradient time(min) [% A/% B] 0.0 [90/10] to 1.35 [20/80] to 2.25 [20/80] to 2.26 [90/10]; 3.0 [90/10] flow: 0.8 mL/min; column temp.: 50° C.

Method G: General conditions: mobile phase A: H$_2$O (1.5 mL TFA/4 L); B: CH$_3$CN (0.75 mL TFA/4 L) Stop Time: 2 min; gradient time(min) [% A/% B] 0.0 [100/0] to 0.9 [40/60] to 1.5 [40/60] to 1.51 [100/0]; 2.0 [100/0] flow: 1.2 mL/min; column temp.: 50° C. Method G1: Xtimate C18, 2.1*30 mm, 3 um Method H: General conditions: mobile phase A: H$_2$O (0.1% TFA); B: CH$_3$CN (0.05% TFA) Stop Time: 10 min; gradient time(min) [% A/% B] 0.0 [90/10] to 0.8 [90/10] to 4.5 [20/80] to 7.5 [20/80]; 9.5 [90/10] flow: 0.8 mL/min; column temp.: 50° C. Method H1: Agilent TC-C18, 2.1*50 mm, 5 um Method I: Shimadzu LCMS 2010, Shim-pack XR-ODS, 3*30 mm, mobile phase A: H$_2$O (0.1% TFA; B: CH$_3$CN (0.05% TFA) Stop Time: 7 min; gradient time(min) [% A/% B]0.01 [90/10] to 6.0 [20/80] to 6.5[20/80] to 6.51 [90/10]; flow: 0.8 mL/min; column temp.: 50° C.

Method J: Agilent TC-C18, 50×2.1 mm, 5 μm, mobile phase A: H$_2$O (0.1% TFA; B: CH$_3$CN (0.05% TFA) Stop Time: 10 min; Post Time: 0.5 min; gradient time(min) [% A/% B]0 [100/0] to 1 [100/0] to 5[40/60] to 7.5 [15/85] to 9.5 [100/0]; flow: 0.8 mL/min; column temp.: 50° C.

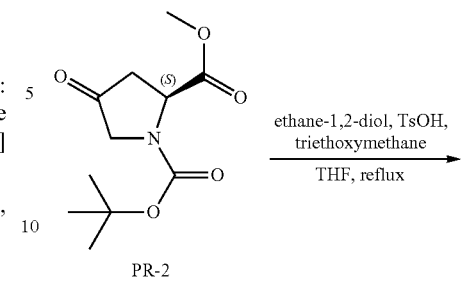

PR-2

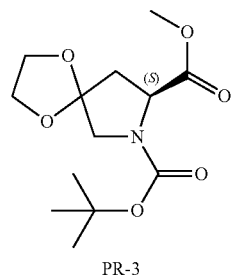

PR-3

Compound PR-2 (30 g, 123 mmol) in THF (120 mL), ethane-1,2-diol (53.6 g, 864 mmol), triethoxymethane (54.6 g, 369 mmol) and TsOH (3 g, 3.69 mmol) were added at 25° C. The mixture was stirred at refluxed for 5 hours. The mixture was poured into aqueous NH$_4$Cl (400 mL) and extracted with ethyl acetate (3×100 mL). The combined organic layers were washed with brine and dried over Na$_2$SO$_4$. The organic phase was concentrated in vacuo. The obtained residue was purified by silica gel column chromatography (hexane:ether acetate=10:1) resulting in compound PR-3 (8.4 g).

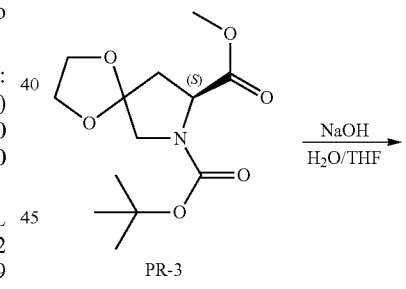

PR-3

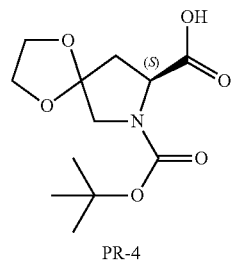

PR-4

To a stirred solution of compound PR-3 (8.4 g, 29.3 mmol) in THF/H$_2$O (100 mL, 1:1) was added NaOH (5.85 g, 146 mmol). The reaction mixture was stirred at 20° C. for 1 hour and treated with ethyl acetate (20 mL). The inorganic layer was separated, adjusted to pH=4 with 2N HCl, and extracted with CH$_2$Cl$_2$ (3×50 mL). The combined organic layer was washed with brine, dried over Na$_2$SO$_4$ and concentrated in vacuo to resulting in compound PR-4 (5.9 g).

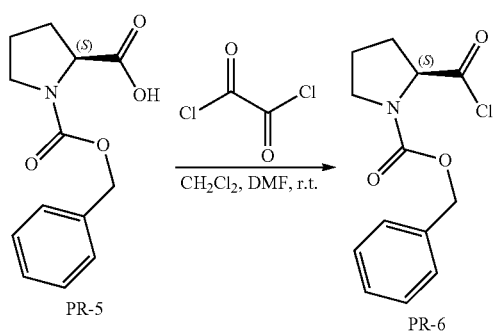

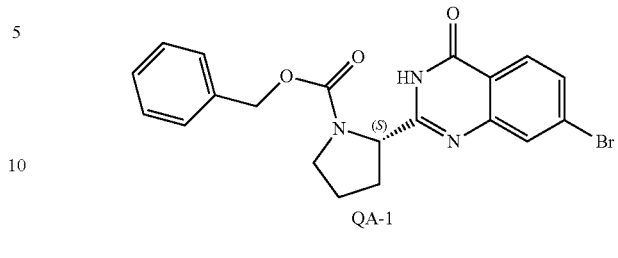

Compound PR-5 (15.7 g, 63.1 mmol) was dissolved in dry CH$_2$Cl$_2$ (250 mL) and DMF (1.5 mL) was added to the solution. Oxalyl chloride (13.5 mL, 157.5 mmol) was added dropwise at room temperature. The reaction mixture was stirred for 0.5 hour at room temperature. The reaction mixture was concentrated in vacuo and the residue (PR-6, 22 g) was used directly without further purification.

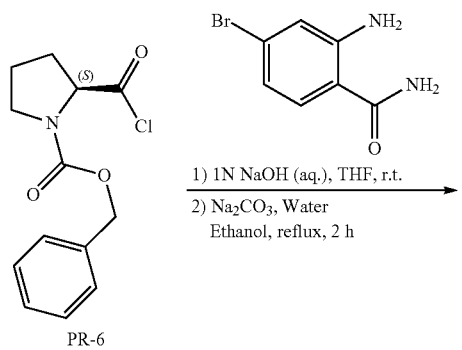

To the solution of compound PR-6 (Crude 22 g) in dry THF (250 mL) was added 2-amino-4-bromobenzamide (7.6 g, 35.3 mmol) and 1 N NaOH (aq. 85 mL, 85 mmol). The mixture was stirred for 1 hour at room temperature. The reaction mixture was extracted with ethyl acetate (3×100 mL). The combined organic layers were washed with 1 N NaOH in water (15 mL), brine, dried over Na$_2$SO$_4$ and concentrated in vacuo resulting in a crude residue (17 g). The crude residue, obtained similar as described above (25 g), and Na$_2$CO$_3$ (17.8 g, 168 mmol) in ethanol (250 mL) and H$_2$O (250 mL) was refluxed for 2 hour. The organic solvent was removed in vacuo. The mixture was extracted with dichloromethane (2×200 mL). The combined organic layers were washed with brine, dried over Na$_2$SO$_4$ and purified by silica gel column chromatography (eluent: ethyl acetate). The desired fractions were evaporated to dryness. The obtained residue was stirred in ethyl acetate (50 mL), the precipitate was filtered off and washed with ethyl acetate resulting in compound QA-1 (17 g).

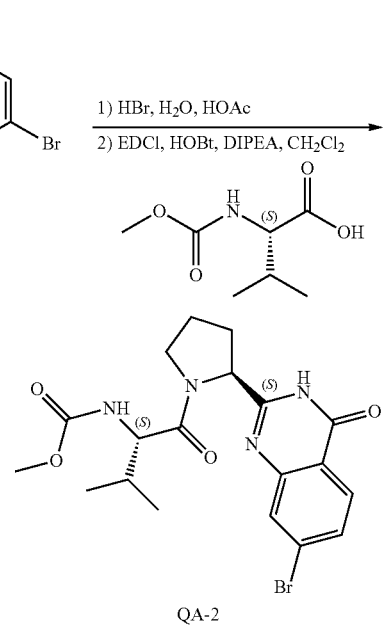

Compound QA-1 (8 g, 18.6 mmol) was dissolved in HOAc (80 mL) and 40% HBr (40 mL) was added. The mixture was stirred at 80° C. overnight. Most of the solvent was removed in vacuo. The precipitate was filtered off and washed with methyl t-butyl ether. The solid was co-evaporated with toluene (2×20 mL) resulting in a crude residue (6.5 g). Part of this residue (6.4 g), (S)-2-(methoxycarbonylamino)-3-methylbutanoic acid (4.5 g, 25.6 mmol), EDCI (4.9 g, 25.6 mmol) and HOBt (1.15 g, 8.5 mmol) in CH₂Cl₂ (120 mL) were then cooled to 0° C. DIPEA (14.8 mL, 85.0 mmol) was added. The mixture was stirred for 1.5 hour at 20° C. The organic layer was washed with saturated aqueous NaHCO₃ (100 mL) and dried over Na₂SO₄. The solvent was removed in vacuo. The residue was purified by silica gel column chromatography (gradient eluent: petroleum ether:ethyl acetate: from 100:0 to 0:100) resulting in compound QA-2 (3.3 g).

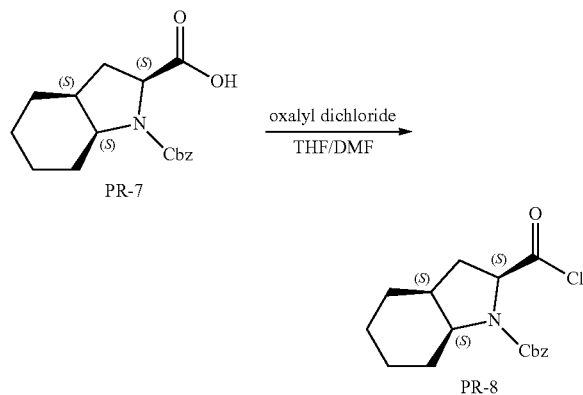

Compound PR-7 (7.0 g, 23.21 mmol) in THF (70 mL) was stirred at 0° C. Oxalyl dichloride (7 mL, 46.2 mmol) and DMF (2 drops) were added dropwise and the mixture was stirred for 10 min at 0° C. The mixture was stirred and refluxed for 1 hour. The mixture was cooled and evaporated in vacuo, resulting in compound PR-8 (7 g)

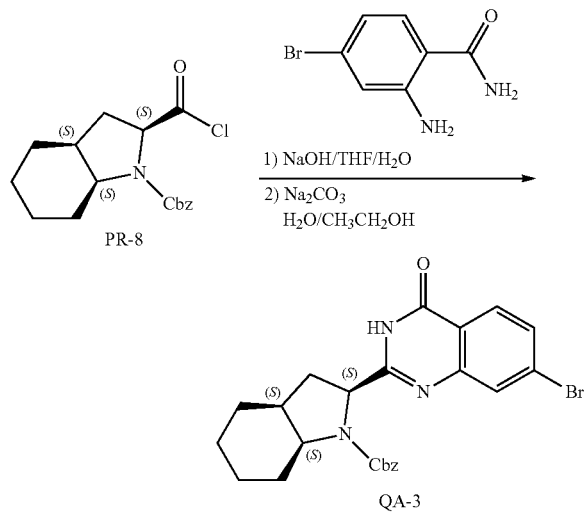

To the solution of compound PR-8 (7 g, 21 mmol) in THF (70 mL) was added 2-amino-4-bromobenzamide (4.5 g, 21 mmol) and 1N NaOH (42 mL, 42 mmol). The mixture was stirred for 1 hour at 25° C. The mixture was extracted with ethyl acetate. The organic layers were collected, washed with 0.5 N NaOH, brine, dried and concentrated in vacuo, resulting in a crude residue (9 g). This residue (9 g) and Na₂CO₃ (5.7 g, 54 mmol) in H₂O (200 mL) and THF (200 mL) was stirred and refluxed for 2 hour. The mixture was concentrated in vacuo and extracted with CH₂Cl₂ (2×), washed with brine, dried and evaporated in vacuo. The residue was dissolved in CH₂Cl₂ and washed with 1 N HCl (3×), brine, dried and evaporated in vacuo, resulting in QA-3 (4.4 g). Method A2; Rt: 1.27 min. m/z=: 484.0 (M+H)⁺ Exact mass: 483.1

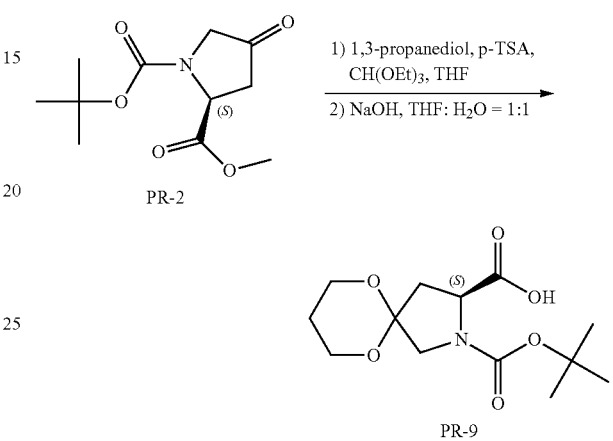

To compound PR-2 (10 g, 41.2 mmol) in THF (100 mL), 1,3-propanediol (22 g, 288-mmol), triethylorthoformate (18.3 g, 123.6 mmol) and Toluene-4-sulfonic acid (1 g, 0.2 mmol) were added at 25° C. The mixture was stirred at refluxed for 2 hour. The mixture was poured into aqueous NH₄Cl (400 mL), extracted with ethyl acetate (3×50 mL) and separated. The combined organic layers were washed with brine and dried over Na₂SO₄. The organic phase was concentrated in vacuo. The residue was purified by silica gel column chromatography (hexane:ether acetate=5:1) and the compound obtained (3.8 g,) was dissolved in THF/H₂O (40 mL, 1:1). NaOH (2.52 g, 63 mmol) was added, the reaction mixture was stirred at room temperature for 1 hour and treated with ethyl acetate (20 mL). The combined inorganic layer was separated, pH=adjusted to 4 with 2N HCl, and extracted with CH₂Cl₂ (3×20 mL). The combined organic layer was washed with brine, dried over Na₂SO₄ and concentrated in vacuo resulting in compound PR-9 (5.9 g).

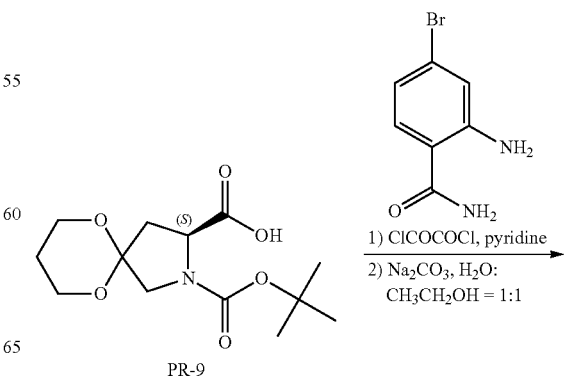

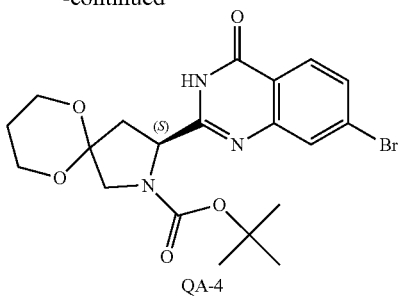

QA-4

Oxalyl dichloride (2.5 mL, 13.11 mmol) was added drop wise to a mixture of the compound PR-9 (2.5 g, 8.74 mmol), 2-amino-4-bromobenzamide (2.5 g, 10.49 mmol) in dichloromethane (20 mL) and pyridine (20 mL) at room temperature. The mixture was stirred for 1 hour at room temperature. The solvent was removed in vacuo. The residue was purified by column chromatography (petroleum ether:acetate ether=1:1). The obtained intermediate amide compound (0.98 g), Na₂CO₃ (1.08 g. 10.15 mmol), H₂O (5 mL) and CH₃CH₂OH (5 mL) were stirred for 2 hours under reflux. Most of CH₃CH₂OH was removed in vacuo and the obtained residue was extracted with ethyl acetate. The organic layer was dried over Na₂SO₄ and concentrated in vacuo. The residue was washed with t-butyl methyl ether resulting in compound QA-4 (0.89 g).

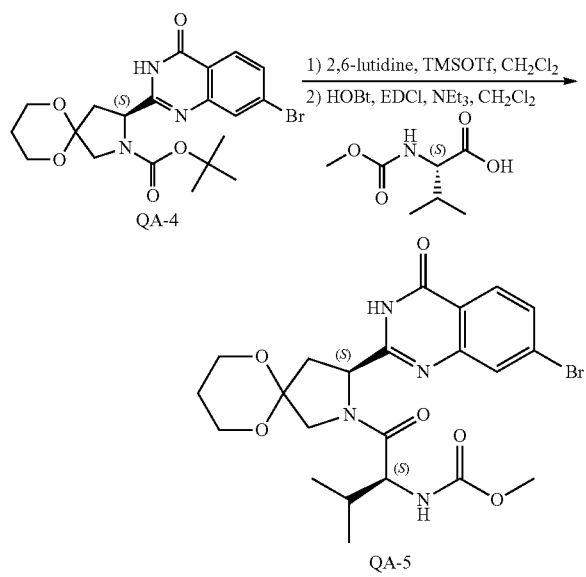

QA-5

To a stirred solution of compound QA-4 (0.89 g, 1.92 mmol) and lutidine (0.41 g, 3.84 mmol) in dry CH₂Cl₂ (10 mL) at 0° C. was added drop wise TMSOTf (1.7 g, 7.68 mmol). The reaction mixture was stirred at 0° C. for 30 minutes, quenched with saturated aqueous NH₄Cl, and extracted with ethyl acetate; the combined organic layers were washed with brine, dried over Na₂SO₄ and concentrated in vacuo. The obtained residue was used as such in the next reaction (0.3 g). Method A2; Rt: 0.68 min. m/z=: 368.0 (M+H)⁺ Exact mass: 367.0. NEt₃ (0.5 mL, 2.46 mmol) was added to the solution of the above obtained residue (0.3 g), (S)-2-(methoxycarbonylamino)-3-methylbutanoic acid (0.22 g, 1.23 mmol), HOBt (0.17 g, 1.23 mmol) and EDCI (0.24 g, 1.23 mmol) in dichloromethane (15 mL) in ice-water bath. The reaction mixture was stirred for 2 hours at room temperature. Then the mixture was diluted with dichloromethane (20 mL) and washed with Saturated NaHCO₃, brine and dried over Na₂SO₄. The solvent was removed in vacuo. The residue was purified by column chromatography (hexane:ether acetate=1:1), resulting in compound QA-5 (0.2 g). Method A2; Rt: 1.14 min. m/z=: 547.1 (M+Na)⁺ Exact mass: 524.1

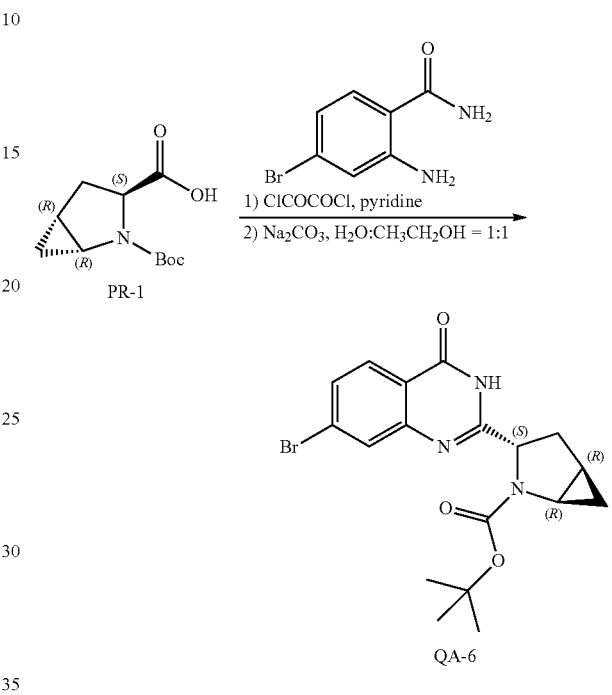

QA-6

Oxalyl chloride (2.9 mL, 33 mmol) was added drop wise to the mixture of compound PR-1 (5 g, 22 mmol), 2-amino-4-bromobenzamide (4.7 g, 22 mmol) and pyridine (50 mL). The mixture was stirred for 1 hour at room temperature. The solvent was removed in vacuo. The obtained residue was purified by chromatography (petroleum ether:acetate ether=5:1) resulting in a intermediate (3.6 g). Method A2; Rt: 1.15 min. m/z=: 447.7 (M+Na)⁺ Exact mass: 425.1 The above obtained intermediate (3.6 g,), Na₂CO₃ (2.7 g. 25.4 mmol), H₂O (20 mL) and CH₃CH₂OH (20 mL) were stirred for 2 hours under reflux. Most of CH₃CH₂OH was removed in vacuo. The residue was extracted with ethyl acetate (3×20 mL). The organic layer was dried over Na₂SO₄ and concentrated in vacuo. The residue was washed with t-butyl methyl ether resulting in compound QA-6 (3.4 g)

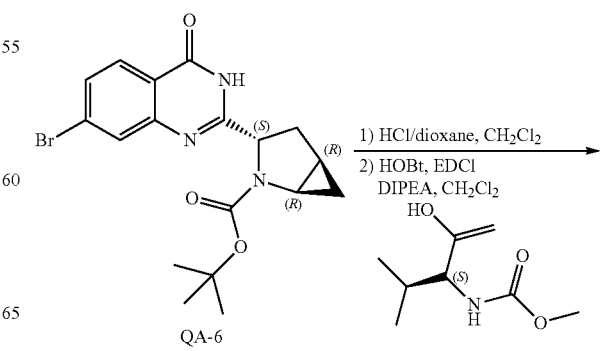

QA-6

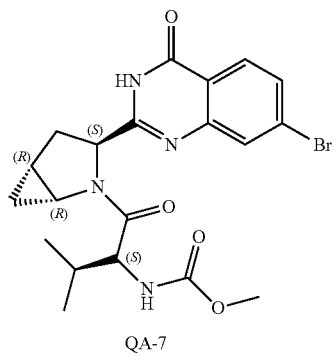

QA-7

Compound QA-6 (3.4 g, 8.4 mmol) was dissolved in dichloromethane (30 mL) and HCl/dioxane (3 mL) was added drop wise to the mixture at 0° C. The reaction mixture was stirred for 5 hours at room temperature. The solvent was removed in vacuo. The residue was washed with t-butyl methyl ether and the obtained crude residue was used as such (2.7 g).To a solution of this crude (2.7 g), (S)-2-(methoxycarbonylamino)-3-methylbutanoic acid (2.75 g, 15.76 mmol), HOBt (2.42 g, 17.33 mmol) and EDCI (3.32 g, 17.33 mmol) in dichloromethane (20 mL) cooled in an ice-water bath, DIPEA (14 mL, 78.8 mmol) was added. The reaction mixture was stirred for 12 hours at room temperature. The mixture was diluted with dichloromethane (20 mL), washed with saturated NaHCO$_3$, brine and dried over Na$_2$SO$_4$. The solvent was removed in vacuo. The residue was purified by silica gel column chromatography (hexane:ether acetate=1:1), resulting in compound QA-7 (2.5 g). SFC: Column: AD-H 250 mm×4.6 mm; 5 um. Flow: 2.35 mL/min, Mobile phase: A: CO$_2$ B: EtOH (0.05% Diethylamine); 5 to 40% B in A; Rt: 9.99 min

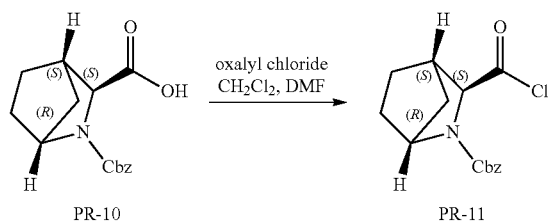

Compound PR-10 (2.0 g, 7.3 mmol) in CH$_2$Cl$_2$ (20 mL) was stirred at 0° C. Oxalyl dichloride (2.3 g, 18.2 mmol) and DMF (2 drops) were added dropwise and the mixture was stirred for 10 minutes at 0° C. The mixture was stirred for 1 hour at 20° C. The mixture was cooled and evaporated in vacuo. The residue was diluted twice with toluene (2×10 mL) and evaporated, resulting in a residue (PR-11, 2.5 g).

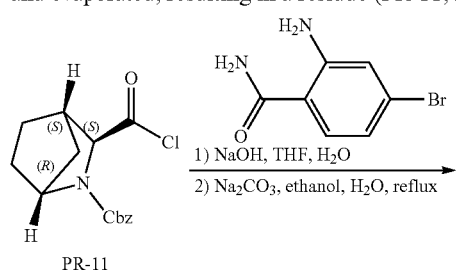

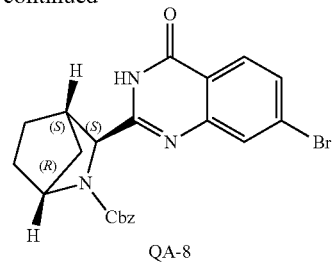

QA-8

To the solution of compound PR-11 (2.5 g) in THF (30 mL) was added 2-amino-4-bromobenzamide (1.57 g, 7.3 mmol) and 1 N NaOH (14.6 mL, 14.6 mmol). The mixture was stirred for 1 hour at 25° C. The mixture was extracted with ethyl acetate (2×). The organic layers were combined, washed with 0.5 N NaOH, brine, dried and concentrated in vacuo, resulting in a residue (3.5 g) that was stirred with Na$_2$CO$_3$ (2.32 g, 21.9 mmol) in H$_2$O (50 mL) and THF (50 mL) and refluxed for 2 hours. The volatiles were removed in vacuo. The mixture was extracted with CH$_2$Cl$_2$ (2×), washed with brine, dried and the volatiles were removed in vacuo. The residue was dissolved in CH$_2$Cl$_2$ and washed with 1 N HCl (3×), brine, dried and the volatiles were removed in vacuo, resulting in compound QA-8 (1.5 g).Method A2; Rt: 1.15 min. m/z=: 453.9 (M+H)$^+$ Exact mass: 453.1

QA-9

ClCOCOCl (44.4 mL, 510.2 mmol) was added dropwise to the mixture of PR-13 (100.6 g, 374 mmol), 2-amino-4-bromobenzamide (73.2 g, 340 mmol) and pyridine (760 mL) under nitrogen at 0° C. The mixture was stirred for 2 hour at room temperature. The solvent was removed in vacuo. Saturated NaHCO$_3$ was added to the residue and the resulting mixture was extracted by ethyl acetate for three times. The combined organic layers were washed with saturated NaHCO$_3$, brine and dried over Na$_2$SO$_4$. The solvent was removed in vacuo. The obtained residue was purified by chromatography (CH$_2$Cl$_2$:MeOH=50:1) resulting in an intermediate amide compound (50.6 g). Method A2; Rt: 1.15 min.

m/z=: 490.1 (M+Na)+ Exact mass: 467.1 A solution of the above obtained intermediate (50.61 g), Na$_2$CO$_3$ (34.51 g. 325.6 mmol), H$_2$O (300 mL) and CH$_3$CH$_2$OH (300 mL) was stirred for 3 hours at reflux. EtOH was removed in vacuo and the mixture was extracted with ethyl acetate (3×300 mL). The combined organic layers were dried over Na$_2$SO$_4$ and concentrated in vacuo. The obtained residue was washed with t-butyl methyl ether resulting in compound QA-9 (39.2 g). Method A2; Rt: 1.37 min. m/z=: 448.1 (M+H)+ Exact mass: 447.1

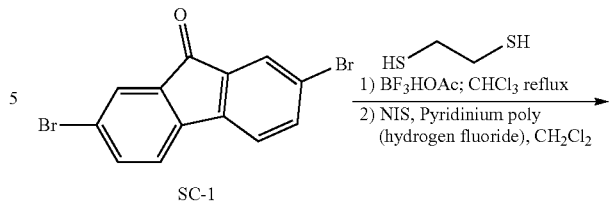

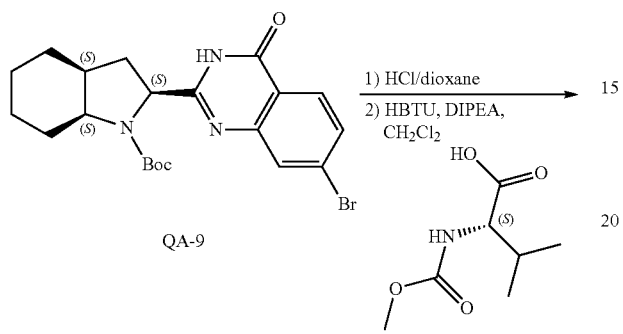

Compound SC-1 (100 g, 296 mmol) was dissolved in CHCl$_3$ (3720 mL). 1,2-ethane-dithiol (53 mL, 592 mmol) and boron trifluoride-acetic acid complex (44 mL, 296 mmol) were added under N$_2$ protection. The mixture was refluxed for 16 hour. The solid was filtrated and dried under high vacuum resulting in the intermediate thioketal (98 g). In a fluoropolymer vessel, NIS (183 g, 811 mmol, 4.8 eq) was dissolved in dry CH$_2$Cl$_2$ (1600 mL). Hydrogen fluoride-pyridine was added at −75° C. The mixture was stirred at −75° C. for 10 minutes. Part of the above obtained thioketal (70 g, 169 mmol) in dry CH$_2$Cl$_2$ (1000 mL) was added dropwise. The mixture was stirred at −75° C. for 15 minutes. The mixture was diluted with CH$_2$Cl$_2$ (800 mL) and passed through a basic alumina gel pad. The solvent was concentrate to 600 mL and washed with saturated Na$_2$SO$_3$ solution (500 mL) and saturated K$_2$CO$_3$ solution (500 mL). The organic layer was dried over Na$_2$SO$_4$ and evaporated in vacuo resulting in compound SC-2 (48 g).

QA-9 (39.2 g, 87.5 mmol) was dissolved in dichloromethane (400 mL). HCl/dioxane (470 mL) was added dropwise to the mixture at 0° C. The reaction mixture was stirred for 3.5 hours at room temperature. The solvent was carefully removed in vacuo. The obtained residue was washed with t-butyl methyl ether, resulting in a residue (30.8 g) Method A2; Rt: 0.92 min. m/z=: 348.1 (M+H)+ Exact mass: 347.1

DIPEA (54.2 mL, 308 mmol) was added, at 0° C., to a solution of the above residue (30.84 g, 61.6 mmol), (S)-2-(methoxycarbonylamino)-3-methylbutanoic acid (11.9 g, 67.8 mmol) and HBTU (35.0 g, 92.4 mmol) in dichloromethane (265 mL) under nitrogen atmosphere. Next, the reaction mixture was stirred for 3 hours under nitrogen atmosphere at room temperature. The reaction mixture was diluted with dichloromethane and washed with saturated NaHCO$_3$, brine and dried over Na$_2$SO$_4$. The solvent was removed in vacuo. The obtained residue was purified by column chromatography (petroleum ether:ethyl acetate=1:1), resulting in compound QA-10 (31.1 g). Method A2; Rt: 1.28 min. m/z=: 507.2 (M+H)+ Exact mass: 506.1

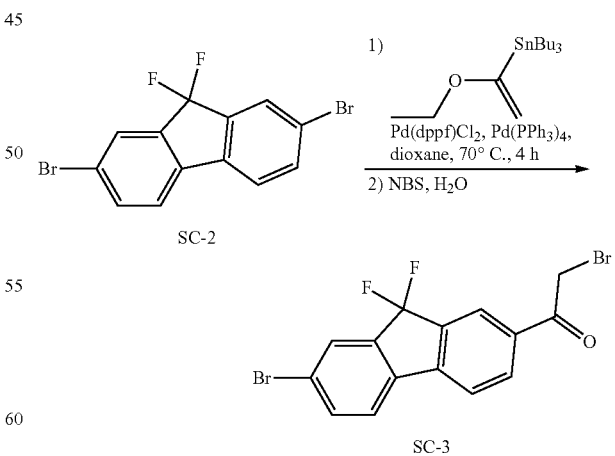

Pd(PPh$_3$)$_4$ (6.5 g, 5.6 mmol, 0.2 eq) and Pd(dppf)$_2$Cl$_2$ (4 g, 5.6 mmol, 0.2 eq) were added to the mixture of compound SC-2 (10 g, 28 mmol, 1 eq), tributyl(1-ethoxy-vinyl)tin (10 g, 28 mmol, 1 eq) and dry dioxane (200 mL). The mixture was stirred at 70° C. under $N_2$ for 4 hours. The mixture was cooled to 20° C. $H_2O$ (50 mL) and NBS (20 g, 112 mmol) were added and the mixture was stirred at 20° C. under $N_2$ for 12 hours. $CH_2Cl_2$ (200 mL) and $H_2O$ (100 mL) were added. The organic layer was dried over $Na_2SO_4$ and evaporated. The residue was purified by silica gel column chromatography (Eluent: petroleum ether:ethyl acetate=3:1) resulting in compound SC-3 (2 g).

(2.4 mL, 17.5 mmol) were added. The mixture was stirred at 25° C. for 3 hours. The solvent was removed in vacuo resulting in a crude residue (4 g). This residue (4 g) was dissolved in toluene (40 mL). $CH_3COONH_4$ (7.7 g, 100 mmol) was added. The mixture was stirred at 100° C. for 2 hours. The solution was diluted with ethyl acetate (20 mL) and washed with $H_2O$ (2×10 mL). The organic layer was dried over $Na_2SO_4$ and evaporated in vacuo. The residue was purified by silica gel column chromatography (Eluent: petroleum ether:ethyl acetate=6:4) resulting in compound SC-4 (2.6 g).

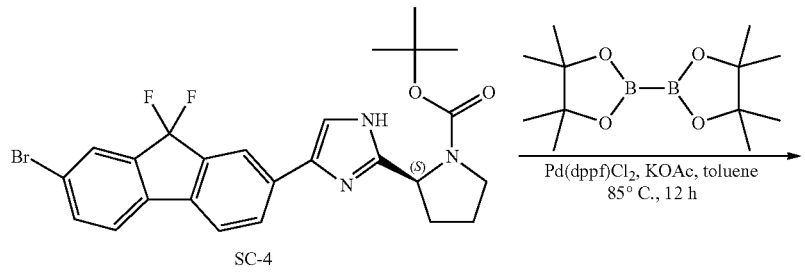

SC-4

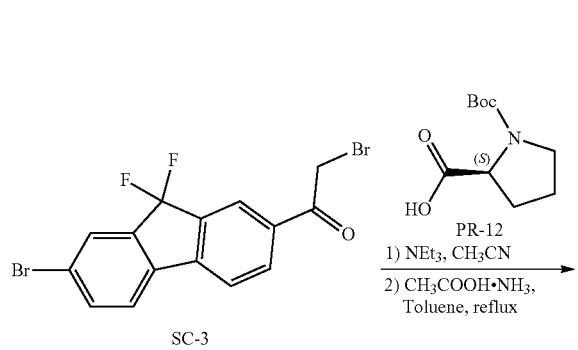

SC-5

Pd(dppf)Cl$_2$ (0.54 g, 0.74 mmol) was added to the mixture of compound SC-4 (4.8 g, 7.4 mmol), KOAc (1.45 g, 14.8 mmol), 4,4,4',4',5,5,5',5'-octamethyl-2,2'-bi(1,3,2-dioxaborolane) (3.76 g, 14.8 mmol) and toluene (48 mL). The mixture was stirred at 85° C. for 12 hours. After cooling, the solvent was evaporated in vacuo, $CH_2Cl_2$ was added and mixture was washed with $H_2O$ (200 mL) and saturated $Na_2CO_3$ solution (200 mL). The combined organic layers was dried over $Na_2SO_4$, filtered and concentrated in vacuo. The residue was purified by silica gel column chromatography (Eluent: $CH_2Cl_2$/ethyl acetate=1:3) resulting in compound SC-5 (2.8 g).

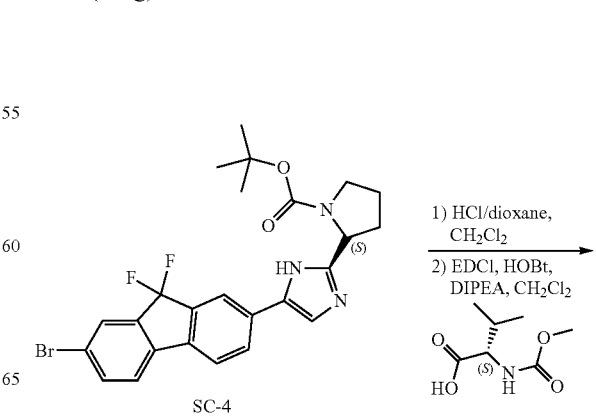

SC-4

Compound SC-3 (2 g, 5 mmol) was dissolved in $CH_3CN$ (20 mL). Boc-L-proline (4.3 g, 20 mmol) and triethylamine -continued

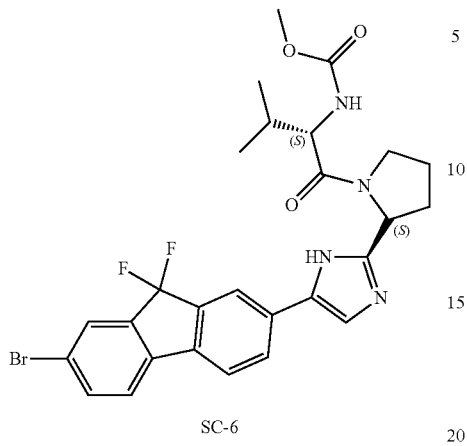

SC-6

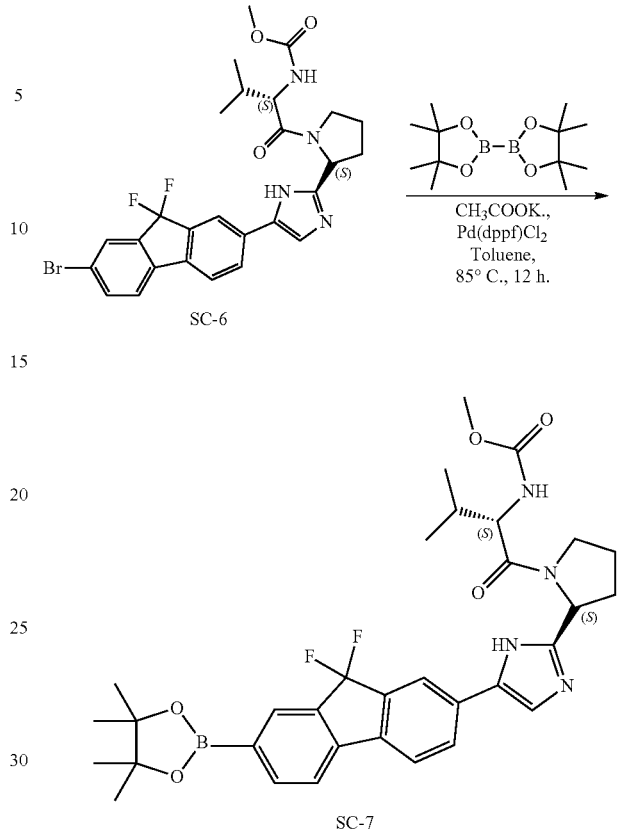

Compound SC-4 (2.6 g, 5 mmol) was dissolved in CH₂Cl₂ (26 mL) and 4N HCl/dioxane (2 mL, 8 mmol) was added at 0° C. The mixture was stirred at 25° C. for 20 minutes. The solvent was removed in vacuo resulting in a residue (2.5 g). Method A2; Rt: 0.95 min. m/z: 415.9 (M+H)⁺ Exact mass: 415.1. This residue (2.5 g), (S)-2-(methoxycarbonylamino)-3-methylbutanoic acid (1.9 g, 11 mmol), EDCI (2.1 g, 11 mmol) and HOBt (1.5 g, 11 mmol) in CH₂Cl₂ (25 mL) was cooled to 0° C. and DIPEA (8.7 mL, 50 mmol) was added. The mixture was stirred at 20° C. for 12 hours.

The mixture was diluted with CH₂Cl₂ (20 mL) and H₂O (5 mL). The organic layer was separated and washed with saturated aqueous NaHCO₃ (5 mL), brine and dried over Na₂SO₄. The solvent was removed in vacuo. The residue was purified by silica gel column chromatography (petroleum ether/ethyl acetate=1:8) resulting in compound SC-6 (2.2 g). Method A2; Rt: 0.97 min. m/z: 575.0 (M+H)⁺ Exact mass: 574.1

Pd(dppf)Cl₂ (0.14 g, 0.19 mmol) was added to the mixture of compound SC-6 (2.2 g, 3.8 mmol), 4,4,4',4',5,5,5',5'-octamethyl-2,2'-bi(1,3,2-dioxaborolane) (1.95 g, 7.6 mmol), CH₃COOK (0.75 g, 7.6 mmol) and dry toluene (45 mL). The mixture was stirred at 85° C. for 12 hours. After cooling, the solvent was evaporated in vacuo, CH₂Cl₂ was added and mixture was washed with H₂O (200 mL) and saturated Na₂CO₃ solution (200 mL). The combined organic layers was dried over Na₂SO₄, filtered and concentrated in vacuo. The residue was purified by silica gel column chromatography (Eluent: petroleum ether/ethyl acetate=1:3) resulting in compound SC-7 (2.05 g). Method A2; Rt: 0.98 min. m/z: 621.1 (M+H)⁺ Exact mass: 620.3

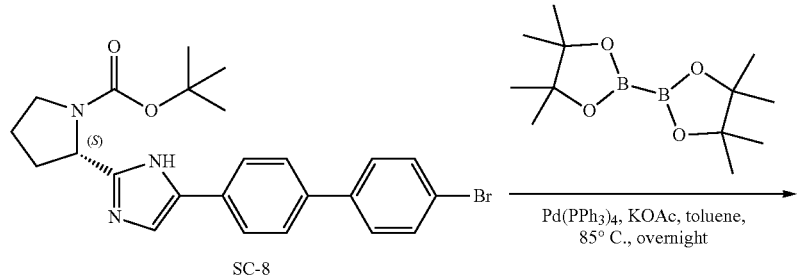

SC-8

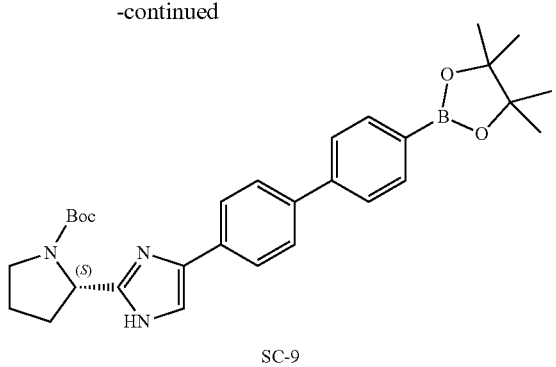

SC-9

Pd(PPh₃)₄ (0.4 g, 0.35 mmol) was added to the mixture of compound SC-8 (3.3 g, 7 mmol), 4,4,4',4',5,5,5',5'-octamethyl-2,2'-bi(1,3,2-dioxaborolane) (3.6 g, 14 mmol), KOAc (1.4 g, 14 mmol) and toluene (75 mL). The mixture was stirred at 85° C. for 12 hours. After cooling, CH₂Cl₂ was added and mixture was washed with saturated Na₂CO₃ solution (200 mL) and brine (200 mL). The water was extracted with CH₂Cl₂ (3×200 mL). The combined organic layers was dried over Na₂SO₄, filtered and concentrated in vacuo. The residue was purified by silica gel column chromatography (Eluent: CH₂Cl₂/Methanol=10:1). The solvent was removed in vacuo resulting in compound SC-9 (1.6 g). Method A2; Rt: 1.11 min. m/z: 516.1 (M+H)⁺ Exact mass: 515.3 was removed in vacuo and the obtained residue was co-evaporated with toluene (2×20 mL) and used to the next step without further purification. Method A2; Rt: 0.96 min. m/z: 368.1 (M+H)⁺ Exact mass: 367.1

The above obtained residue (S)-2-(methoxycarbonylamino)-3-methylbutanoic acid (5.6 g, 32 mmol), EDCI (6.1 g, 32 mmol) and HOBt (1.4 g, 10 mmol) in CH₂Cl₂ (180 mL) was cooled to 0° C. DIPEA (18.6 g, 106 mmol) was added dropwise. The mixture was stirred for 1 hour at 25° C. The organic layer was washed with saturated aqueous layer NaHCO₃ (20 mL) and dried over Na₂SO₄. The solvent was removed in vacuo. The residue was purified by silica gel column chromatography (gradient eluent: ethyl acetate:

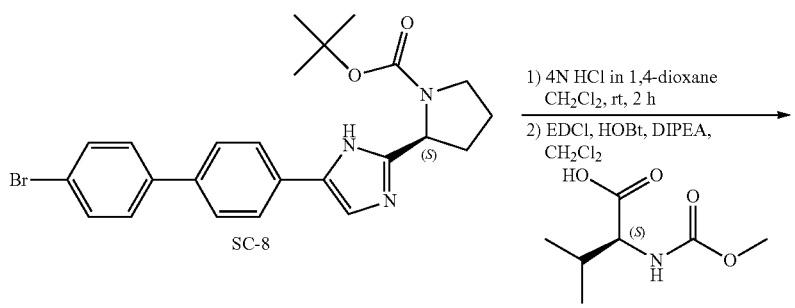

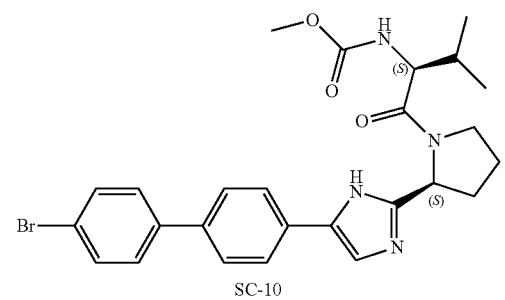

SC-10

Compound SC-8 (10 g, 21 mmol) was dissolved in CH₂Cl₂ (100 mL) and 4 N HCl/dioxane (50 mL) was added dropwise. The mixture was stirred for 30 minutes at 25° C. The solvent methanol: from 100:0 to 20:1), resulting in compound SC-10 (9.9 g) as a white powder. Method A2; Rt: 1.02 min. m/z: 527.1 (M+H)⁺ Exact mass: 526.1

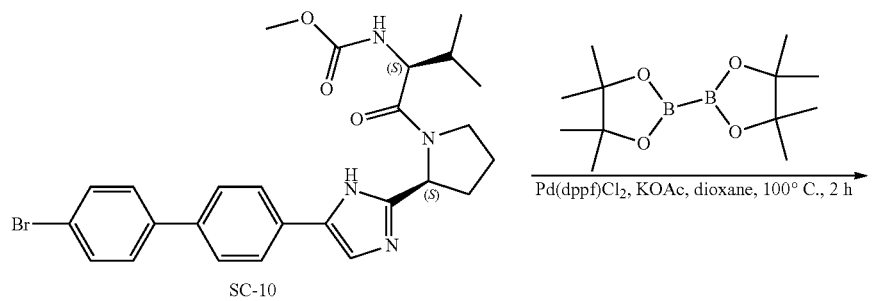

SC-10

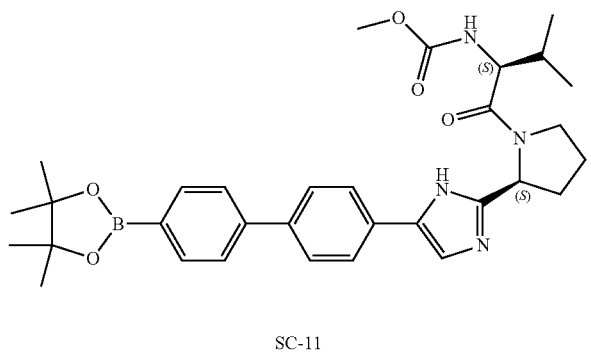

SC-11

A mixture of compound SC-10 (2 g, 3.80 mmol), 4,4,4',4',5,5,5',5'-octamethyl-2,2'-bi(1,3,2-dioxaborolane) (1.9 g, 7.6 mmol), Pd(dppf)Cl$_2$, (0.28 g, 0.38 mmol), KOAc (0.75 g, 7.6 mmol) in dry dixoane (20 mL) was stirred for 2 hours at 100° C. under a N$_2$ atmosphere. The solid was filtered and the filtrate was evaporated to dryness. The residue was purified by silica gel column chromatography (gradient eluent: petroleum ether:ethyl acetate: from 100:0 to 0:100). resulting in compound SC-11 (1.88 g) as a white powder. Method A2; Rt: 1.08 min. m/z: 573.1 (M+H)$^+$ Exact mass: 572.3

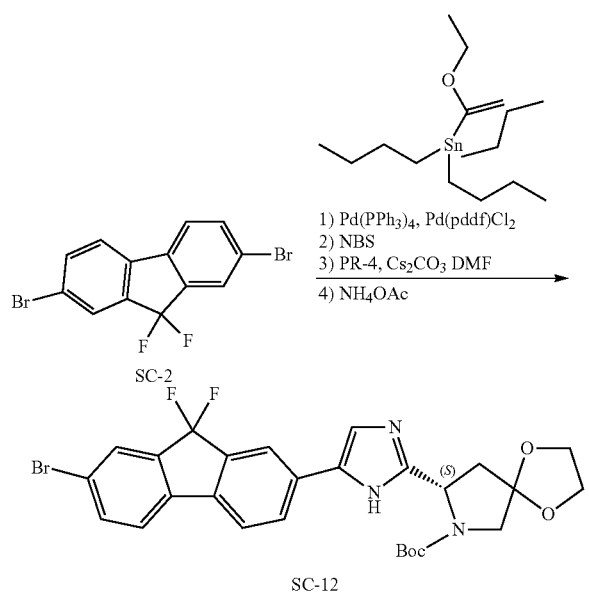

SC-2 (20 g, 55.5 mmol), tributyl(1-ethoxyvinyl)tin (20 g, 55.5 mmol), Pd(PPh$_3$)$_4$ (13 g, 12 mmol) and Pd(ddpf)Cl$_2$ (8 g, 12 mmol) were suspended in 1,4-dioxane (100 mL) at 20° C. The mixture was stirred at refluxed for 4 hours. The mixture was poured into H$_2$O (30 mL) at 20° C. NBS (40 g, 110.0 mmol) was added and the resulting mixture was stirred at 20° C. for 12 hours. The mixture was poured into H$_2$O (50 mL) and extracted with ethyl acetate (3×100 mL). The combined organic layers were washed with brine and dried over Na$_2$SO$_4$. The organic phase was concentrated in vacuo resulting in crude SC-3 (21 g). The obtained residue was used to the next reaction without purification. Cs$_2$CO$_3$ (20.0 g, 61.38 mmol) was added to a stirred solution of PR-4 (7.6 g, 27.81 mmol) in DMF (40 mL). The reaction mixture was stirred at 20° C. for 0.5 hour. Crude SC-3 (21.0 g, 52.23 mmol) was added to the mixture. The reaction mixture was stirred at 20° C. for 2 hours. The mixture was washed with water (20 mL) and extracted with ethyl acetate (3×50 mL). The combined organic layers were washed with brine, dried over Na$_2$SO$_4$ and concentrated in vacuo. The obtained residue was purified by silica gel column chromatography (eluent: hexane:ether acetate=5:1) resulting in (S)-8-(2-(7-bromo-9,9-difluoro-9H-fluoren-2-yl)-2-oxoethyl) 7-tert-butyl 1,4-dioxa-7-azaspiro[4.4]nonane-7,8-dicarboxylate (8 g).

To a stirred solution of (S)-8-(2-(7-bromo-9,9-difluoro-9H-fluoren-2-yl)-2-oxoethyl) 7-tert-butyl 1,4-dioxa-7-azaspiro[4.4]nonane-7,8-dicarboxylate (8 g) in xylene (80 mL) in an autoclave, NH$_4$OAc (20 g, 260 mmol) was added. The reaction mixture was stirred at 140° C. for 1 hour. The mixture was washed with water (90 mL) and extracted with ethyl acetate (3×50 mL); the combined organic layer was washed with brine, dried over Na$_2$SO$_4$ and concentrated in vacuo. The obtained residue was purified by preparative high performance liquid chromatography over RP-18 (eluent: CH$_3$CN in H$_2$O (0.5% NH$_4$HCO$_3$) from 40% to 80%, v/v). The pure fractions were collected and the volatiles were removed in vacuo. The aqueous layer was lyophilized to dryness resulting in SC-12 (4.12 g). Method A2; Rt: 1.12 min. m/z: 576.1 (M+H)$^+$ Exact mass: 575.1

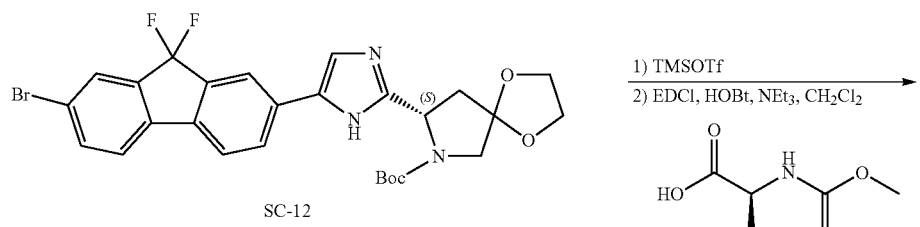

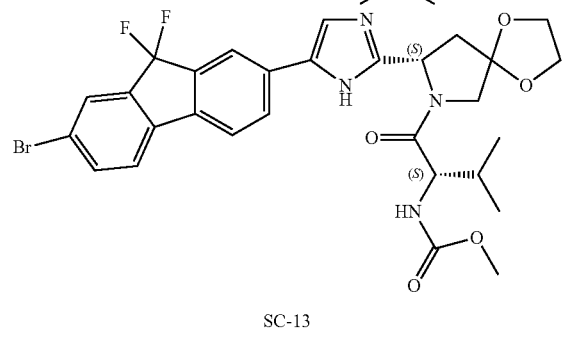

SC-13

To a stirred solution of compound SC-12 (4.5 g, 7.85 mmol) and 2,6-lutidine (1.68 g, 15.7 mmol) in dry CH$_2$Cl$_2$ (50 mL) at 0° C., TMSOTf (7 g, 31.4 mmol) was added drop wise. The reaction mixture was stirred at 0° C. for 30 minutes, quenched with saturated aqueous NH$_4$Cl and extracted with ethyl acetate (3×50 mL). The combined organic layers were washed with brine, dried over Na$_2$SO$_4$ and concentrated in vacuo, resulting in (S)-8-(5-(7-bromo-9,9-difluoro-9H-fluoren-2-yl)-1H-imidazol-2-yl)-1,4-dioxa-7-azaspiro[4.4]nonane (2 g). NEt$_3$ (0.5 g, 45 mmol) was added to a stirred solution of (S)-8-(5-(7-bromo-9,9-difluoro-9H-fluoren-2-yl)-1H-imidazol-2-yl)-1,4-dioxa-7-azaspiro[4.4]nonane (2 g, 4.2 mmol), (S)-2-(methoxycarbonylamino)-3-methylbutanoic acid (0.89 g, 5 mmol), EDCI (0.96 g, 5 mmol) and HOBt (0.67 g, 5 mmol) in dry CH$_2$Cl$_2$ (50 mL). The reaction mixture was stirred at 20° C. for 2 hours, quenched with saturated aqueous Na$_2$CO$_3$, and extracted with CH$_2$Cl$_2$ (3×10 mL). The combined organic layer was washed with brine, dried over Na$_2$SO$_4$ and concentrated in vacuo. The obtained residue was purified by preparative high performance liquid chromatography over RP-18 (eluent: CH$_3$CN in H$_2$O (0.5% NH$_4$HCO$_3$) from 30% to 70%, v/v). The pure fractions were collected and the organic volatiles were removed in vacuo. The aqueous layer was lyophilized to dryness resulting in SC-13 (1.2 g) as a white solid. Method A2; Rt: 1.09 min. m/z: 633.3 (M+H)+ Exact mass: 632.1

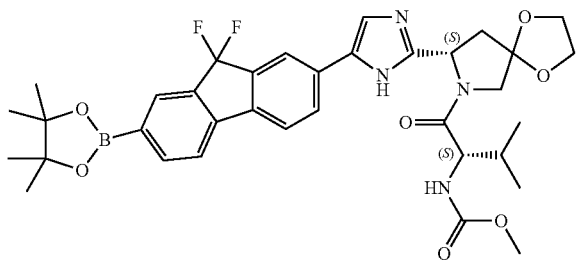

SC-14

To a stirred solution of compound SC-13 (1.2 g, 1.9 mmol) and Pd(dppf)Cl$_2$ (0.1 g, 0.137 mmol) in dry dioxane (25 mL), 4,4,4',4',5,5,5',5'-octamethyl-2,2'-bi(1,3,2-dioxaborolane) (0.72 g, 2.8 mmol) and KOAc (0.37 g, 3.76 mmol) were added. The reaction mixture was refluxed for 30 minutes, quenched with water, and extracted with ethyl acetate (3×20 mL). The combined organic layer was washed with brine, dried over Na$_2$SO$_4$ and concentrated in vacuo. The obtained residue was purified by silica gel column chromatography (hexane:ether acetate=1:1) resulting in compound SC-14 (0.756 g) as a yellow solid.

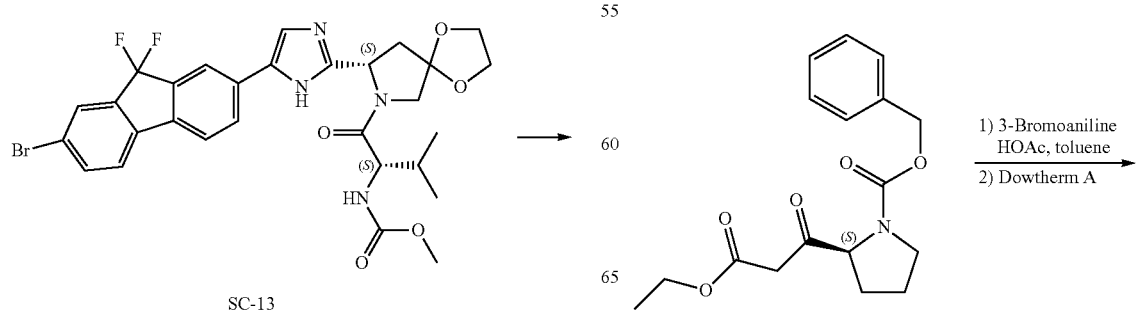

SC-13

1) 3-Bromoaniline HOAc, toluene
2) Dowtherm A

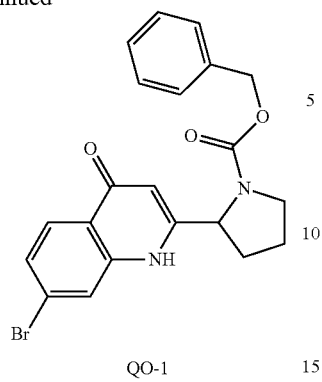

QO-1

3-Bromoaniline (186 g, 1080 mmol) was added to a mixture of (S)-benzyl 2-(3-ethoxy-3-oxopropanoyl)pyrrolidine-1-carboxylate ((460 g, 1440 mmol) in toluene containing acetic acid (86.4 g, 1440 mmol) and was refluxed for 8 hours using a Dean Stark apparatus to remove the reaction water. The mixture was concentrated under reduced pressure and dried in vacuo. The crude product was used in the next step without further purification (662 g). A flask fitted with a stirrer, distillation head and dropping funnel was purged with nitrogen. Dowtherm™ A (90 mL) was added and then was heated to 240° C. A solution of the above obtained residue (662 g) in Dowtherm™ A (900 mL) was added over 10 min, while the temperature was maintained in the range 230-245° C. The mixture was heated for another 1 hour at 240° C. and then cooled to room temperature. Petroleum ether (2000 mL) and heptane (2400 mL) were added. An oily residue formed and the solvent was decanted. The collected oil residue was purified by flash column chromatography (eluent: $CH_2Cl_2$: EtOAc=10:1 to 1:3) resulting in compound 4 (38 g). Method B; Rt: 5.20 min. m/z: 429.0 $(M+H)^+$ Exact mass: 428.1 Columns: AD-H 50 mm*4.6 mm, 3 um Flow: 4 mL/min; Mobile phase: A: $CO_2$ B: EtOH (0.05% Diethylamine), 5% to 40% B in A; Temperature: 40° C., isomer 4a: Rt: 1.53 min; 4b Rt: 1.73 min.

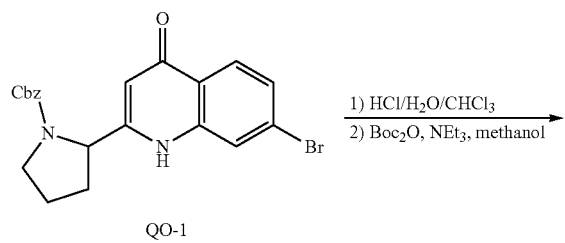

QO-1

Compound QO-1 (1.85 g, 4.3 mmol) was dissolved in $CHCl_3$ (10 mL). Conc. HCl (10 mL) was added and the mixture was stirred in a sealed-tube at 60° C. for 1 hour. The solvent was removed in vacuo. The obtained residue (1.6 g) was dissolved in methanol (30 mL) and $NEt_3$ (1.8 mL, 13.0 mmol) was added. Next, $Boc_2O$ (1.1 g, 5.2 mmol) was added dropwise at 0° C. After addition, the mixture was stirred for 0.5 h at 20° C. The solvent was removed in vacuo and the obtained residue was purified by silica gel column chromatography (gradient eluent: petroleum ether: ethyl acetate: from 100:0 to 0:100). Resulting in compound QO-2 (1.08 g). Method A2; Rt: 0.97 min. m/z=: 392.9 $(M+H)^+$ Exact mass: 392.1

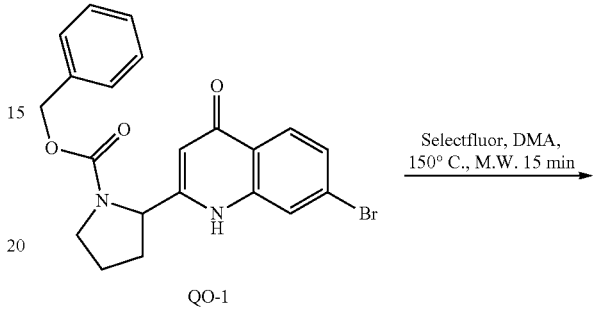

QO-1

QO-3

Compound QO-1 (1 g, 2.3 mmol) and Selectfluor (0.81 g, 2.3 mmol) in DMA (10 mL) were stirred at 150° C. for 15 min. The mixture was cooled to room temperature. and poured into pre-cooled saturated $NaHCO_3$ (100 mL). The precipitate was filtered, washed with $H_2O$ and purified by silica gel chromatography. (Eluent: $CH_2Cl_2$/EtOAc, 1/1). The collected fractions were combined and concentrated in vacuo. The obtained residue was solidified by THF (3 mL), resulting in compound QO-3 (0.13 g). Method A2; Rt: 1.55 min. m/z=: 447.0 $(M+H)^+$ Exact mass: 446.1

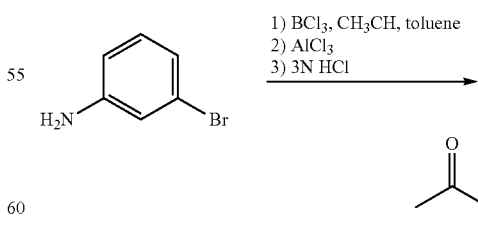

Acetonitrile (23.7 g, 580 mmol) was added to 3-Bromoaniline (10 g, 58 mmol) in toluene (70 mL). The mixture was cooled to 0° C. and $BCl_3$ (1 M in $CH_2Cl_2$, 64 mL, 64 mmol)

was added dropwise, while keeping the temperature below 10° C. Next, AlCl₃ (11.6 g, 87 mmol) was added in small portions at 0° C. The reaction mixture was heated to 90° C. for 5 hours. The reaction mixture was cooled to room temperature and quenched with aqueous HCl (2N, 100 mL). The mixture was heated to 50° C. for 1 hour, cooled to room temperature and separated. The organic layer was separated and washed with water and brine. The organic layer was collected, dried and concentrated, resulting in 1-(2-amino-4-bromophenyl)ethanone (4 g). Method A2; Rt: 0.98 min. m/z=: 215.7 (M+H)⁺ Exact mass: 215.0

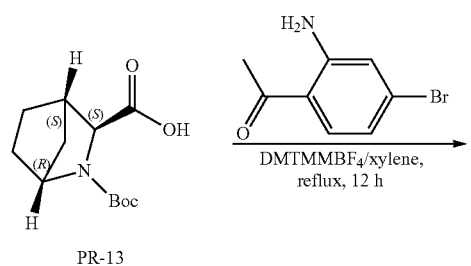

Compound PR-13 (10.6 g, 43.9 mmol), 4 A molecular sieve (1.0 g) and 1-(2-amino-4-bromophenyl)ethanone (9.4 g, 43.9 mmol) in xylene (100 mL) were stirred and refluxed for 1 hour. 4-(4,6-Dimethoxy-1,3,5-triazin-2-yl)-4-methyl-morpholinium BF₄ (DMTMM.BF₄, 15.8 g, 48.3 mmol) was added and the mixture was stirred and refluxed for 12 hours. The mixture was filtrated and the filtrate was concentrated in vacuo. The obtained residue was purified by silica gel column chromatography (eluent: petroleum ether/CH₂Cl₂=5:1 then petroleum ether/ethyl acetate=1/1 v/v). resulting in compound QO-4 (10.9 g).

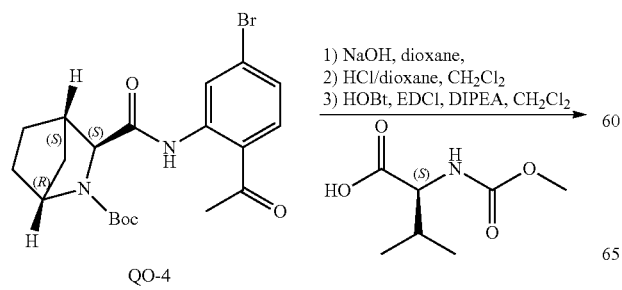

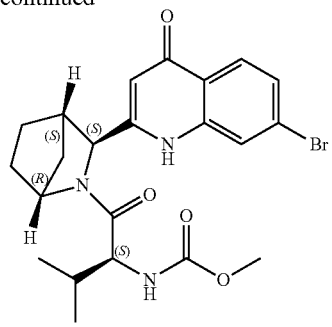

QO-5

Compound QO-4 (10.0 g, 22.9 mmol) and NaOH (co-evaporated with toluene, 3.2 g, 80 mmol) in dioxane (100 mL) were stirred for 1 hour at 100° C. under N₂. The mixture was poured into 10% NH₄Cl (200 mL). The mixture was extracted with CH₂Cl₂ (2×100 mL). The organic layers were washed with brine, dried and concentrated in vacuo. The obtained residue was purified by column chromatography on silica gel (eluent: CH₂Cl₂ then ethyl acetate). The pure fractions were collected and the solvent was removed in vacuo. To the obtained quinolinone (3.0 g) in CH₂Cl₂ (30 mL), 4 N HCl/dioxane (30 mL) was added dropwise. The mixture was stirred for 2 hours at 20° C. and then the volatiles were removed in vacuo. The obtained residue (3.0 g), (S)-2-(methoxycarbonylamino)-3-methylbutanoic acid (1.9 g, 10.8 mmol), EDCI (2.1 g, 10.8 mmol) and HOBt (0.49 g, 3.6 mmol) in CH₂Cl₂ (30 mL) were stirred at 0° C. DIPEA (4.7 g, 36 mmol) was added. The mixture was stirred for 2 hours at 20° C. H₂O (30 mL) was added and the mixture was filtered off. The solid was collected and dried resulting in compound QO-5. The filtrate was separate and the organic layer was washed with H₂O (2×30 mL), brine, dried and evaporated in vacuo. The residue was purified by column chromatography on silica gel (eluent: ethyl acetate then ethyl acetate: CH₃OH=10:1).The pure fractions were collected and the solvent was concentrated in vacuo resulting in more compound QO-5 (3 g in total).

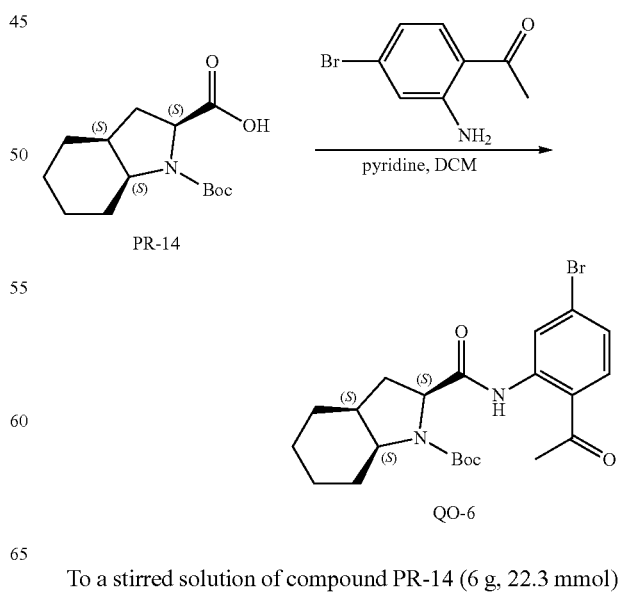

To a stirred solution of compound PR-14 (6 g, 22.3 mmol) in CH₂Cl₂/pyridine (100 mL, 1/1) at 0° C., (COCl)₂ (5.6 g, 44.6 mmol) was added drop wise. The mixture was stirred at 25° C. for 0.5 hour. Then the mixture was added to a solution of 1-(2-amino-4-bromophenyl)ethanone (4.7 g, 22.3 mmol) in CH$_2$Cl$_2$ (30 mL). The mixture was stirred at 25° C. for 1 hour. The mixture was poured into H$_2$O (100 mL), extracted with CH$_2$Cl$_2$ (3×50 mL) and separated. The combined organic layers were washed with brine and dried on Na$_2$SO$_4$. The organic phase was concentrated in vacuo. The residue was purified by column chromatography (hexane:ether acetate=5:1) resulting in compound QO-6 (9 g) as a solid.

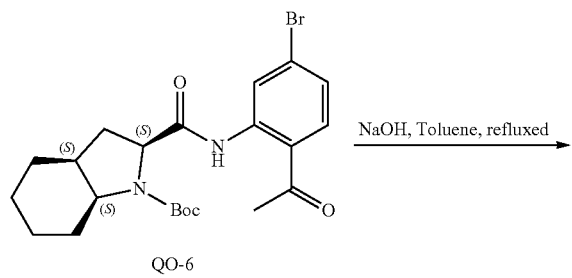

To compound QO-6 (9 g, 19.3 mmol), in toluene (100 mL),NaOH (3 g, 77.2 mmol) was added at 25° C. The mixture was stirred at refluxed for 1 hour. The mixture was poured into aqueous NH$_4$Cl (50 mL), extracted with ethyl acetate (3×100 mL) and separated. The combined organic layers were washed with brine and dried over Na$_2$SO$_4$. The organic phase was concentrated in vacuo. The residue was purified by column chromatography (hexane:ether acetate=10:1) resulting in compound QO-7 (3.5 g). Method A2; Rt: 1.25 min. m/z=: 449.1 (M+H)$^+$ Exact mass: 448.1

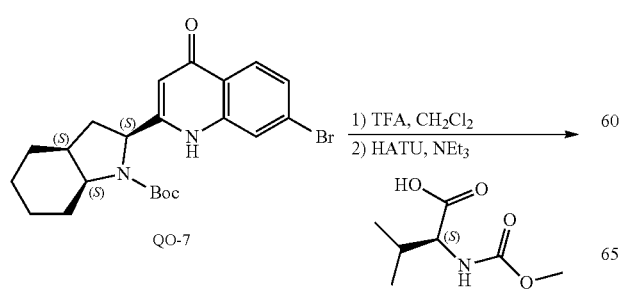

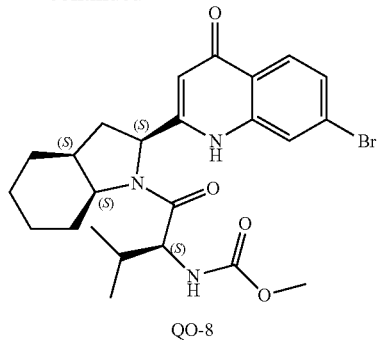

To a solution of compound QO-7 (3.5 g, 7.83 mmol) in CH$_2$Cl$_2$ (100 mL) was added drop wise TFA (10 mL) at 25° C. The mixture was stirred at 25° C. for 0.5 hour. The solvent was removed in vacuo. The residue was washed with t-butyl methyl ether and dried in vacuo, the resulting solid (2.4 g) was stirred in CH$_2$Cl$_2$ (100 mL) with (S)-2-(methoxycarbonylamino)-3-methylbutanoic acid (1.45 g, 8.3 mmol), HATU (3.15 g, 8.3 mmol) and NEt$_3$ (0.84 g, 8.3 mmol) at 25° C. The mixture was stirred at 25° C. for 1 hour. The mixture was poured into H$_2$O (50 mL), extracted with CH$_2$Cl$_2$ (3×50 mL) and separated. The combined organic layers were washed with brine and dried on Na$_2$SO$_4$. The organic phase was concentrated in vacuo. The residue was purified by column chromatography (hexane:ether acetate=5:1) resulting in compound QO-8 (1.5 g) as a solid. Method A2; Rt: 1.11 min. m/z=: 506.2 (M+H)$^+$ Exact mass: 505.1; $^1$H NMR (400 MHz, DMSO-d$_6$) δ ppm 0.85 (d, J=6.7 Hz, 3 H), 0.90 (d, J=6.7 Hz, 3 H), 1.15-1.37 (m, 2 H), 1.37-1.56 (m, 2 H), 1.56-1.79 (m, 3 H), 1.82-2.11 (m, 3 H), 2.23-2.43 (m, 2 H), 3.55 (s, 3 H), 3.93 (t, J=8.7 Hz, 1 H), 4.45 (dt, J=11.7, 5.9 Hz, 1 H), 4.73 (dd, J=10.3, 7.4 Hz, 1 H), 5.89 (br. s., 1 H), 7.44 (dd, J=8.6, 1.9 Hz, 1 H), 7.54 (d, J=8.0 Hz, 1 H), 7.73 (d, J=1.9 Hz, 1 H), 7.95 (d, J=8.5 Hz, 1 H), 11.63 (br. s., 1 H)

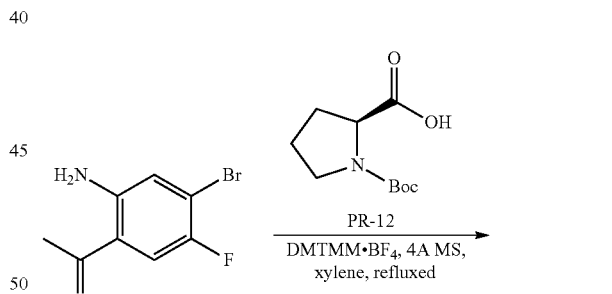

1-(2-amino-4-bromo-5-fluorophenyl)ethanone (0.36 g, 1.57 mmol) and compound PR-12 (0.34 g, 1.57 mmol) in xylene (8 mL) was refluxed for 1 hour. DMTMM.BF$_4$ (0.57 g, 1.73 mmol) was added and the mixture was stirred and refluxed for 8 hours. The solvent was removed in vacuo and the obtained residue was purified by silica gel column chromatography. (Gradient eluent: petroleum ether/ethyl acetate from 1 to 1/2), resulting in compound QO-9 (0.5 g).

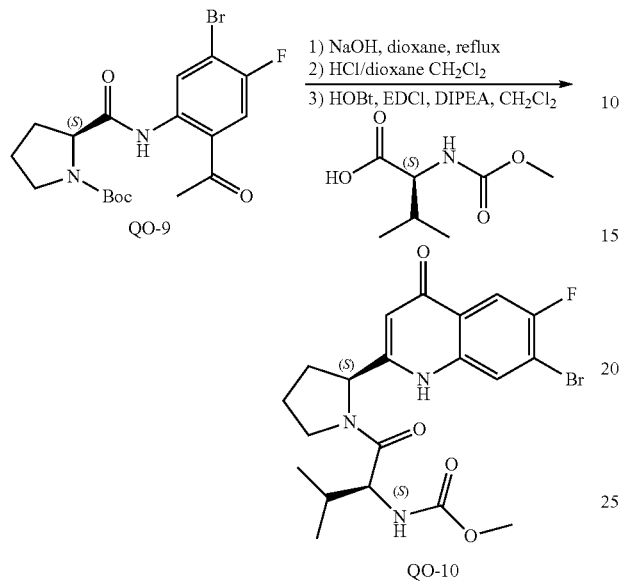

Compound QO-9 (0.5 g, 1.16 mmol) and NaOH (0.16 g, 4.0 mmol) in dry dioxane (5 mL) were stirred at 100° C. for 1 hour under $N_2$. The mixture was poured to 10% $NH_4Cl$ solution (20 mL). The residue was extracted with $CH_2Cl_2$ (2×10 mL), dried over $Na_2SO_4$ and evaporated in vacuo. The obtained residue (0.5 g) was dissolved in $CH_2Cl_2$ (5 mL). 4 N HCl/dioxane (2 mL) was added at 0° C. and the mixture was next stirred at 25° C. for 20 min. The solvent was removed in vacuo. The obtained residue (0.5 g), (S)-2-(methoxycarbonylamino)-3-methylbutanoic acid (0.45 g, 2.55 mmol), EDCI (0.49 g, 2.55 mmol) and HOBt (0.34 g, 2.55 mmol) in $CH_2Cl_2$ (10 mL) was cooled to 0° C. and DIPEA (2.3 mL, 11.6 mmol) was added. The mixture was stirred at 20° C. for 12 hours. The mixture was diluted with $CH_2Cl_2$ (20 mL) and $H_2O$ (5 mL). The organic layer was separated and washed with saturated aqueous $NaHCO_3$ (5 mL), brine and dried over $Na_2SO_4$. The solvent was removed in vacuo. The obtained residue was purified by silica gel column chromatography (Eluent: methanol/$CH_2Cl_2$=15%), resulting in compound QO-10 (150 mg) as a white powder.

Method A2; Rt: 0.92 min. m/z=: 470.1 $(M+H)^+$ Exact mass: 469.0

4-bromo-1-fluoro-2-nitrobenzene (50 g, 227 mmol) was dissolved in ethanol (600 mL). Subsequently, a suspension of $Na_2SO_3$ (71.6 g, 568 mmol) in ethanol (1000 mL) and water (1250 mL) was added. The suspension was stirred at 70° C. for 15 hours. Then, at room temperature, the reaction mixture was acidified with HCl (2N) to pH=2 and concentrated in vacuo. The remaining residue was dissolved under reflux in brine (1000 mL). Subsequently, water (100 mL) was added and the solution was cooled in an ice bath. The precipitate was collected by filtration, resulting in 4-bromo-2-nitrobenzenesulfonic acid (57.3 g, 89%).

To a solution of thionyl chloride (50 mL) was added 4-bromo-2-nitrobenzenesulfonic acid (30 g, 106 mmol) and DMF (1 drop) and the reaction mixture was heated to reflux for 4 hours. Upon cooling, the reaction mixture was azeotroped with toluene for three times. The residue was dissolved in a minimal amount of toluene and then the resulting mixture was added to a mixture of concentrated aqueous ammonium hydroxide solution (1 mL) and THF (10 mL) at −10° C. After stirring for 2 hours the reaction was quenched by adding a solution of 6 M aqueous hydrochloric acid until pH=4. The organic layer was separated and then dried and concentrated in vacuo. Petroleum ether was added to the resulting slurry and the product was collected by vacuum filtration resulting in 4-bromo-2-nitrobenzenesulfonamide.

A suspension of 4-bromo-2-nitrobenzenesulfonamide (21.2 g, 75 mmol) in 57% HI (250 mL) was heated at 90° C. for 4 hours. After cooling to room temperature, the dark purple mixture was diluted with ethyl acetate (500 mL) and next washed successively by saturated aq $Na_2S_2O_3$, saturated aq $NaHCO_3$ and brine. The colorless organic layer was dried on anhydrous $MgSO_4$, filtrated and concentrated to dryness. The crude product was purified by high-performance liquid chromatography (eluent: $CH_3CN$/$H_2O$ from 22/78 to 52/48 with 0.01% $NH_3H_2O$ as buffer). Resulting in 2-amino-4-bromobenzenesulfonamide (18.6 g). Method B; Rt: 3.36 min. m/z=: 250.9 $(M+H)^+$ Exact mass: 249.9

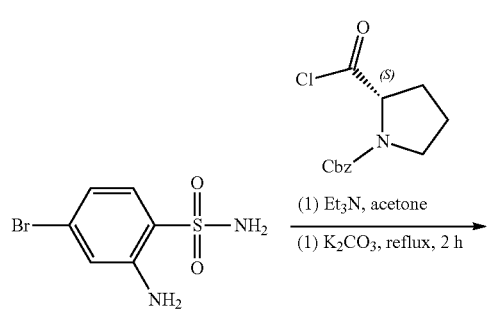

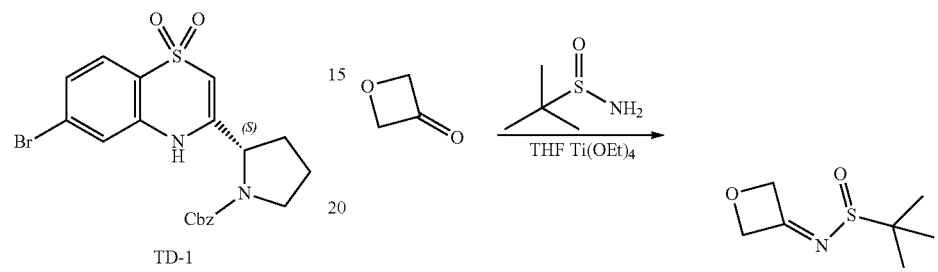

Triethylamine (40.5 mL, 296 mmol) was added to a solution of 2-amino-4-bromobenzenesulfonamide (18.6 g, 74 mmol) in acetone (200 mL). Compound PR-6 (12.8 g, 48 mmol) was added to the reaction mixture under cooling. After stirring for 5 hours, the reaction mixture was diluted with water and acidified by 2 N HCl to pH 4. The resulting precipitate was collected by filtration and then transferred to another flask. A solution of K$_2$CO$_3$ (15 g) in water (100 mL) was added and the reaction mixture was reflux for 2 hours until the reaction became homogeneous. The reaction mixture was acidified by 2 N HCl until pH=4. The precipitate was filtered off and washed with water. The crude product was purified by high performance liquid chromatography (eluent: CH$_3$CN/H$_2$O from 35/65 to 65/35 with 0.75% CF$_3$COOH as buffer), resulting in compound TD-1 (8.3 g, 45%). Method A2; Rt: 1.05 min. m/z=: 487.8 (M+Na)$^+$ Exact mass: 465.0

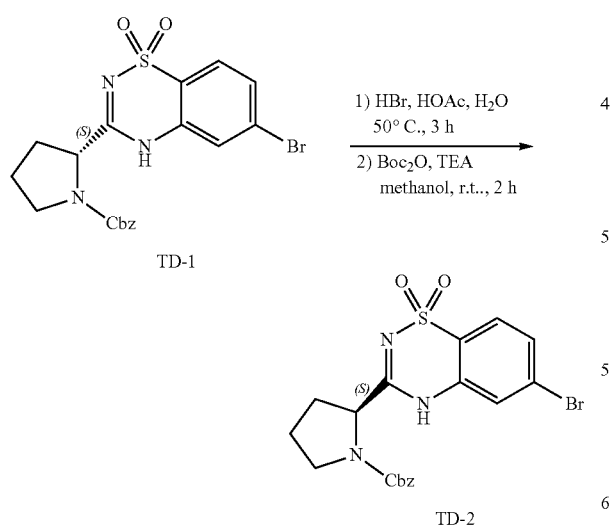

Compound TD-1 (2 g, 4.3 mmol) was dissolved in CH$_3$COOH (20 mL). 40% HBr (30 mL) was added and the mixture was stirred at 50° C. for 3 hours. The solvent was evaporated in vacuo. The obtained residue was washed with tert-butyl methyl ether. The solid was filtered and dried under high vacuum. A solution of the resulting yellow powder. (1.7 g) and Boc$_2$O (1.8 g, 8.2 mmol) in methanol (15 mL) was cooled to 0° C. Triethylamine (2.3 mL, 16.4 mmol) was added. The mixture was stirred at 20° C. for 2 hours and the solvent was removed in vacuo. CH$_2$Cl$_2$ (10 mL) was added and the mixture was washed with H$_2$O (10 mL) and dried on Na$_2$SO$_4$. The solvent was removed in vacuo and the obtained residue was solidified by petroleum ether (5 mL) and filtered. After dried under high vacuum, compound TD-2 was obtained (1.7 g) Method G; Rt: 1.26 min. m/z=: 453.9 (M+Na)$^+$ Exact mass: 431.0

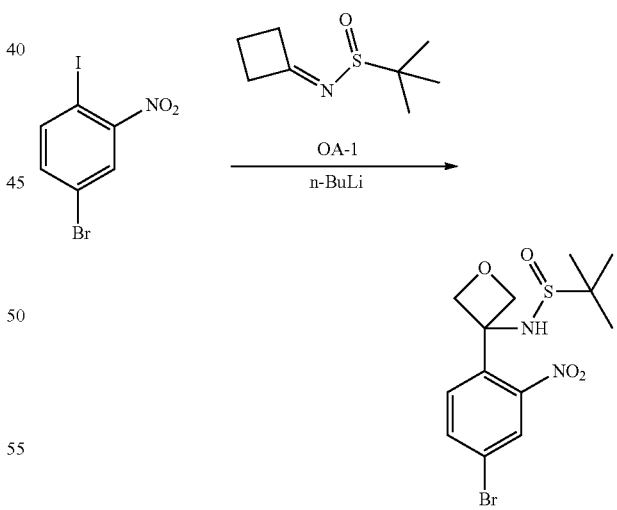

To Oxetan-3-one (5 g, 69 mmol) in THF (50 mL) 2-methylpropane-2-sulfinamide (8.34 g, 69 mmol) and Ti(OEt)$_4$ (20 mL) were added sequentially. The reaction was heated to 50° C. for 5 hours. The reaction was cooled to room temperature and quenched with water (200 mL). The precipitate was filtered and the filtrate was extracted with CH$_2$Cl$_2$ (2×50 mL). The combined organic layer was separated and washed with water (50 mL) and brine (50 mL). The organic layer was dried and concentrated. The crude product was purified by column chromatography (CH$_2$Cl$_2$) resulting in compound OA-1 (5.5 g, 46% yield).

4-bromo-1-iodo-2-nitrobenzene (3 g, 9.18 mmol) was dissolved in anhydrous THF (20 mL) under N$_2$ atmosphere, and the flask was cooled to −78° C. The mixture was stirred for 5 minutes and n-BuLi (4.4 mL, 2.5 mol/L) was slowly added. The reaction mixture turned dark and stirring was continued at −78° C. for 15 minutes. Then, compound OA-1 (1.92 g, 11 mmol) was slowly added to the mixture. The reaction was stirred for 30 minutes at −78° C. and then warmed to room temperature. The mixture was poured into water (50 mL) and extracted with $CH_2Cl_2$ (2×20 mL). The organic phases were separated and washed with brine, dried over $Na_2SO_4$ and concentrated to dryness. The resulting residue was purified by silica gel column chromatography (eluent: petroleum ether/ethyl acetate=3/1), resulting in compound OA-2 (1.3 g, 38% yield). Method A2; Rt: 1.04 min. m/z=: 378.7 (M+H)$^+$ Exact mass: 378.0

Compound OA-2 (1.3 g, 3.45 mmol) was dissolved in MeOH (10 mL) and HCl/dioxane (4N, 10 mL) was slowly added. The reaction was stirred at room temperature for 30 minutes and the mixture was concentrated, resulting in a residue (0.89 g). Method A2; Rt: 0.60 min. m/z=: 272.7 (M+H)$^+$ To the obtained residue, (0.89 g) in a 50 mL flask, HATU (1.49 g, 3.94 mmol), triethylamine (0.66 g, 6.56 mmol) and (S)-1-(tert-butoxycarbonyl) pyrrolidine-2-carboxylic acid (0.84 g, 3.94 mmol,) were added. The residue was dissolved in $CH_2Cl_2$ (10 mL). The reaction mixture was stirred at room temperature for 40 minutes. The mixture was quenched with water (20 mL) and extracted with $CH_2Cl_2$ (2×10 mL). The phases were separated and the organic phase was washed with brine, dried over $Na_2SO_4$ and then concentrated. The obtained residue was purified by silica gel column chromatography (eluent: petroleum ether/ethyl acetate=2/1) resulting in a nitro-intermediate (1.27 g). This nitro-intermediate (1 g, 2.1 mmol) was dissolved in MeOH/water (20 mL 1:1), Fe powder (0.35 g, 6.3 mmol) and $NH_4Cl$ (0.55 g, 10.5 mmol) were added and the mixture was stirred at reflux for 3 hours. The reaction mixture was cooled to room temperature and then concentrated to dryness. The obtained residue was washed with water (10 mL), and extracted with $CH_2Cl_2$ (2×10 mL). The organic layer was separated and concentrated in vacuo, resulting in a intermediate (0.77 g). Method A2; Rt: 1.07 min. m/z=: 464.0 (M+Na)$^+$ Exact mass: 441.1. This intermediate (0.77 g, 1.75 mmol) was dissolved in AcOH (20 mL). The resulting solution was stirred at 80° C. for 30 minutes. The reaction mixture was concentrated in vacuo and the resulting residue was purified by column chromatography (petroleum ether: ethyl acetate=1:1) resulting in compound OA-3 (0.49 g, 66%). Method B; Rt: 4.06 min. m/z=: 422.0 (M+H)$^+$ Exact mass: 421.1

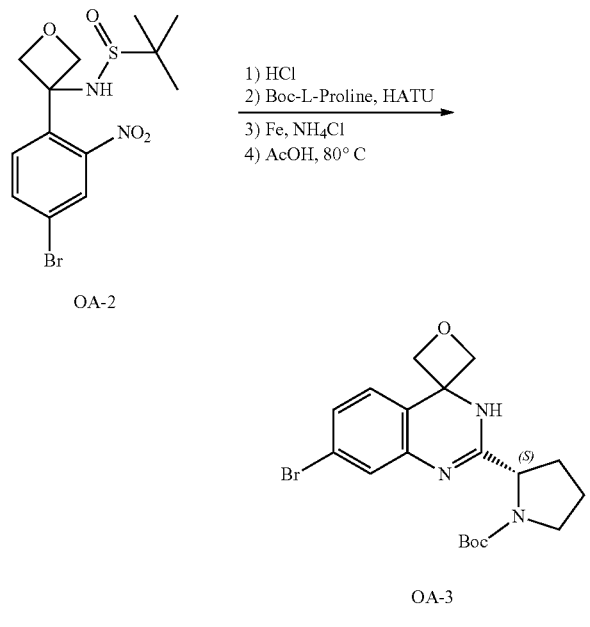

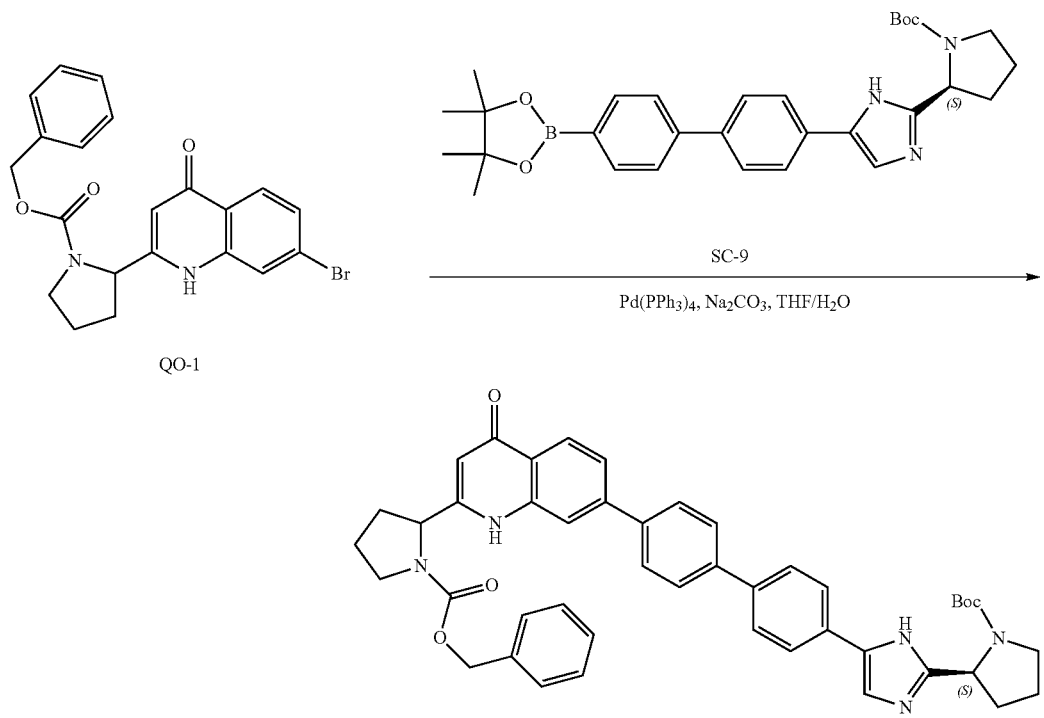

Pd(PPh$_3$)$_4$ (0.14 g, 0.12 mmol) was added to a mixture of compound SC-9 (0.5 g, 1.2 mmol), compound QO-1 (0.41 g, 1.2 mmol), Na$_2$CO$_3$ (0.51 g, 4.8 mmol), THF (20 mL) and H$_2$O (10 mL) under N$_2$ atmosphere. The mixture was stirred under microwave irradiation at 80° C. for 15 minutes. CH$_2$Cl$_2$ (20 mL) and H$_2$O (15 mL) were added to the reaction mixture. The organic layer was separated, washed with brine and dried over Na$_2$SO$_4$. The solvent was evaporated in vacuo. The obtained residue was purified by silica gel column chromatography (Eluent: ethyl acetate: petroleum ether=3:1) resulting in compound 1 (0.43 g). Method A2; Rt: 0.89 min. m/z=: 736.3 (M+H)$^+$ Exact mass: 735.3

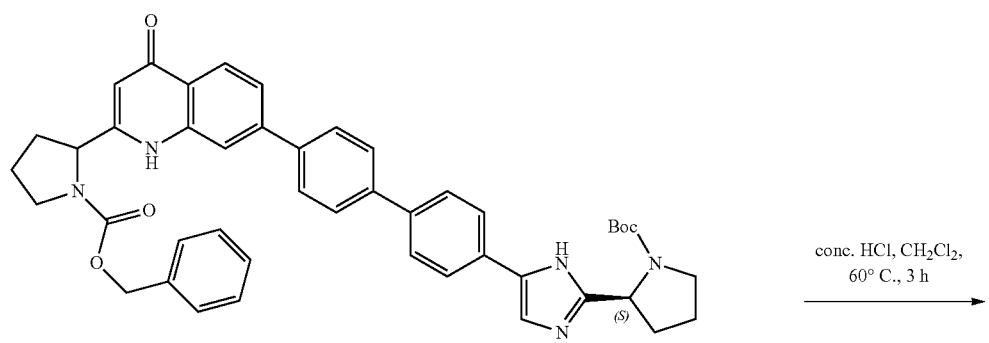

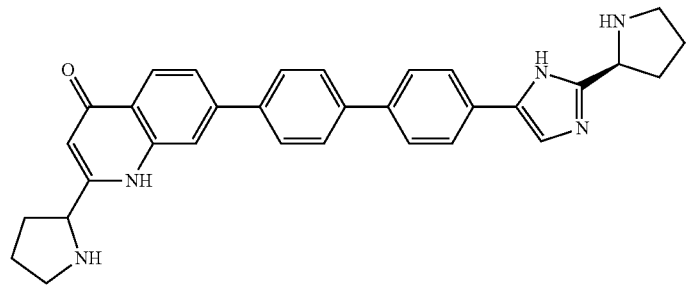

Compound 1 (0.43 g, 0.58 mmol) was dissolved in CHCl$_3$ (4.3 mL). Concentrated HCl (4.3 mL) was added. The mixture was stirred at 60° C. in seal tube for 1 hour. The solvent was evaporated in vacuo resulting in compound 2 (0.6 g). Method A2; Rt: 0.92 min. m/z=: 502.3 (M+H)$^+$ Exact mass: 501.3

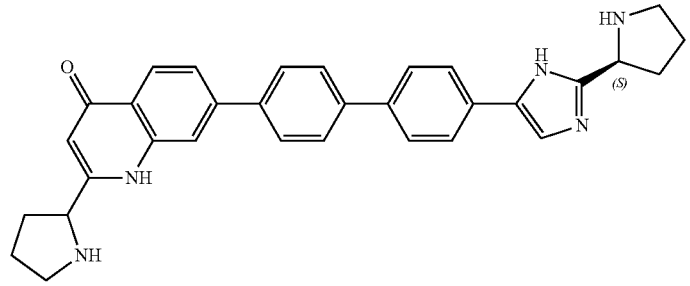

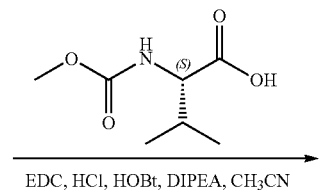

• x HCl

2

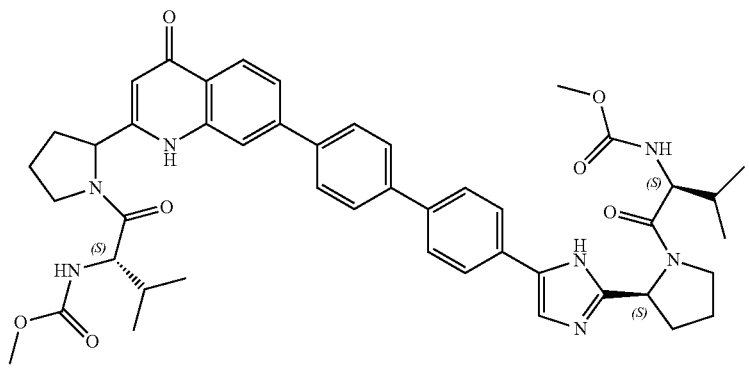

3

To a solution of (S)-2-(methoxycarbonylamino)-3-methylbutanoic acid (0.49 g, 2.78 mmol) in acetonitrile (20 mL), EDCI (0.53 g, 2.78, mmol) and HOBt (0.38 g, 2.78 mmol) were added. After stirring for 1 hour at 10° C., compound 2 (0.6 g) was added. The mixture was then cooled to 0° C. and DIPEA (1.5 g, 11.6 mmol) was added. The mixture was stirred at 10° C. for 12 hours. The solid was filtrated, the obtained filtrate was concentrated and diluted with $CH_2Cl_2$ (20 mL) and 1 N HCl (5 mL). The organic layer was separated and washed with saturated aqueous $NaHCO_3$ (5 mL) and brine and then dried over $Na_2SO_4$. The solvent was removed in vacuo. The obtained compound 3, a mixture of two diastereoisomers 3a and 3b, was purified by high-performance liquid chromatography (Column: Grace Vydac 250*20 mm*5um, Mobile phase A: water (containing 0.075% TFA, V/V % Mobile phase B: acetonitrile (containing 0.025% TFA, V/V % Flow rate: 30 mL/min; Gradient: 35-50% B (v/v) from 0 to 11 min). The two pure fractions were collected and basified with $NaHCO_3$ to pH=8. The volatiles were removed in vacuo. The residue was extracted with $CH_2Cl_2$ (2×10 mL). The organic layer was washed with brine (10 mL) and dried over $Na_2SO_4$. The solvent was removed in vacuo. The obtained residue was washed with acetonitrile (1 mL) and t-butyl methyl ether (1 mL). The solid was dried under high vacuum resulting in the two separate diastereoisomers compound 3a (14 mg) and compound 3b (26 mg).

3a: Method B; Rt: 4.71 min. m/z: 816.3 $(M+H)^+$ Exact mass: 815.4

SFC: Column: OJ-H 250 mm×4.6 mm; 5 um. Flow: 2.35 mL/min, Mobile phase: A: $CO_2$ B: EtOH (0.05% Diethylamine); 5 to 40% B in A; Rt: 8.39 min SFC: Column: OD-H 250 mm×4.6 mm; 5 um. Flow: 2.35 mL/min, Mobile phase: A: $CO_2$ B: MeOH (0.05% Diethylamine); 40% B in A; Rt: 7.67 min 3b: Method B; Rt: 4.79 min. m/z: 816.3 $(M+H)^+$ Exact mass: 815.4

SFC: Column: OJ-H 250 mm×4.6 mm; 5 um. Flow: 2.35 mL/min, Mobile phase: A: $CO_2$ B: MeOH (0.05% Diethylamine); 5 to 40% B in A; Rt: 7.41 min SFC: Column: OD-H 150 mm×4.6 mm; 5 um. Flow: 2.35 mL/min, Mobile phase: A: $CO_2$ B: MeOH (0.05% Diethylamine); 5 to 40% B in A; Rt: 9.60 min

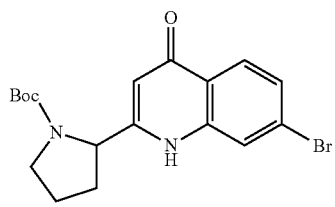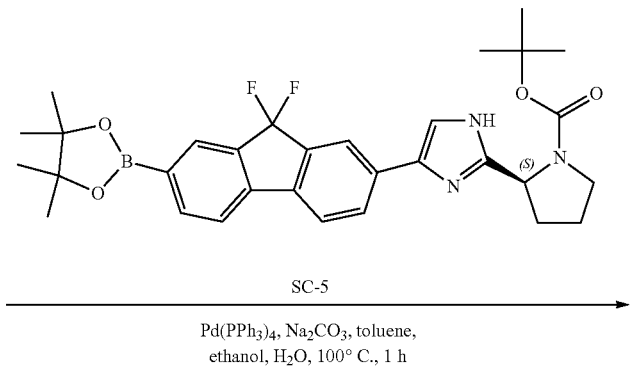

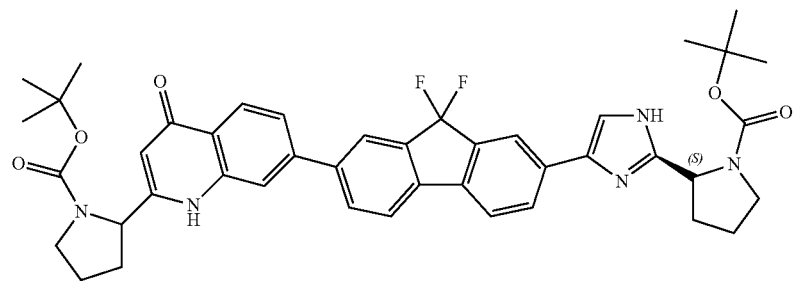

A mixture of compound QO-2 (1.0 g, 2.5 mmol), compound SC-5 (1.4 g, 2.5 mmol), Na₂CO₃ (2.1 g, 20 mmol), Pd(PPh₃)₄ (0.29 g, 0.25 mmol) in H₂O (10 mL), ethanol (10 mL) and toluene (10 mL) was stirred for 1 hour at 100° C. under N₂ atmosphere. Water (10 mL) was added and the mixture was extracted with dichloromethane (2×30 mL). The combined organic layers were dried over Na₂SO₄. After filtration, the solvent was removed in vacuo. The residue was purified by silica gel column chromatography ((gradient eluent: first, ethyl acetate:methanol: from 100:0 to 10:1; then, dichloromethane:methanol: from 10:1 to 1:1), resulting in compound 4 (1.04 g) Method A2; Rt: 0.99 min. m/z: 750.3 (M+H)+ Exact mass: 749.3;

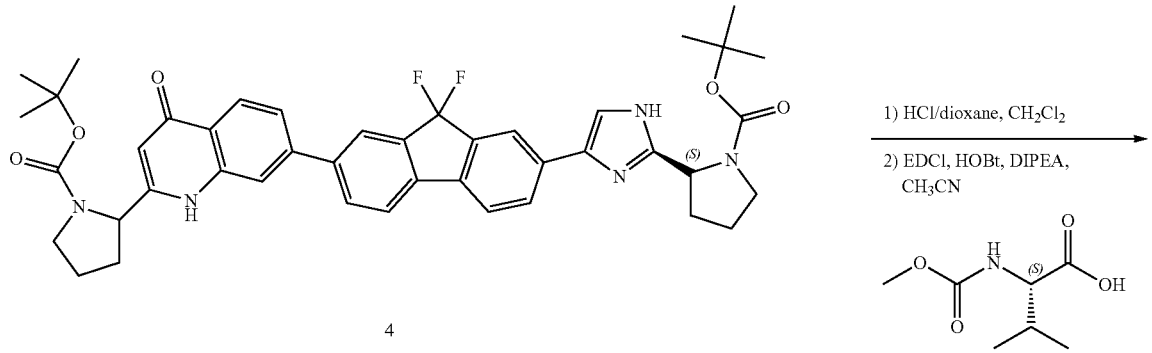

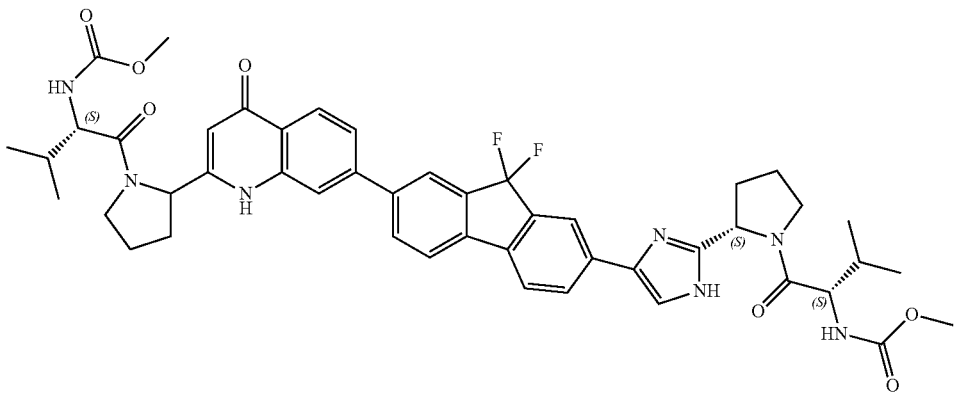

5

Compound 4 (1 g, 1.3 mmol) was dissolved in CH₂Cl₂ (10 mL). 4 N HCl/dioxane (10 mL) was added. The mixture was stirred for 20 minutes at 25° C. The solvent was removed in vacuo. The residue was co-evaporated with toluene (10 mL), resulting in 0.85 g of residue. Method A2; Rt: 0.84 min. m/z: 550.1 (M+H)⁺ Exact mass: 549.2; To this residue (0.85 g, 1.3 mmol) in CH₂Cl₂ (10 mL), (S)-2-(methoxycarbonylamino)-3-methylbutanoic acid (0.51 g, 2.9 mmol), EDCI (0.59 g, 2.9 mmol) and HOBt (0.09 g, 0.67 mmol) were added and the mixture was cooled to 0° C. DIPEA (2.3 mL, 13.3 mmol) was next added and the mixture was stirred for 1.5 hour at 25° C. Water (20 mL) and dichloromethane (20 mL) were added and the organic layer was separated and dried over Na₂SO₄. After filtration, the solvent was removed in vacuo. Compound 5 (mixture of diastereoisomers 5a and 5b) was purified by silica gel column chromatography (gradient eluent: ethyl acetate: methanol: from 100:0 to 6:1) resulting in a light yellow solid. The obtained solid was washed with acetonitrile and further purified by supercritical fluid chromatography (Column: OJ 250 mm*30 mm, 5 um; Mobile phase: A: Supercritical CO₂, B: isopropanol; 0.05% diethyl amine), A:B=65:35 at 55 mL/min, Column Temp: 38° C., Nozzle Pressure: 100 Bar, Nozzle Temp: 60° C., Evaporator Temp: 20° C., Trimmer Temp: 25° C., Wavelength: 220 nm). The obtained fraction of compound 5a and 5b were washed with acetonitrile and further purified by supercritical fluid chromatography (Column: OJ 250 mm*30 mm, 5 um; Mobile phase: A: Supercritical CO₂, B: isopropanol (0.05% diethyl amine), A:B=65:35 at 55 mL/min, Column Temp: 38° C., Nozzle Pressure: 100 Bar, Nozzle Temp: 60° C., Evaporator Temp: 20° C., Trimmer Temp: 25° C., Wavelength: 220 nm). This resulted in compound 5a (148 mg) and 5b (200 mg).

5a: Method C; Rt: 3.66 min. m/z: 864.4 (M+H)+ Exact mass: 863.4;
SFC: Column: OJ-H 250 mm×4.6 mm; 5 um. Flow: 2.35 mL/min, Mobile phase: A: CO2 B: iPrOH (0.05% Diethylamine); 5 to 40% B in A; Rt: 8.18 min 5b: Method C; Rt: 3.72 min. m/z: 864.4 (M+H)+ Exact mass: 863.4;
SFC: Column: OJ-H 250 mm×4.6 mm; 5 um. Flow: 2.35 mL/min, Mobile phase: A: CO2 B: iPrOH (0.05% Diethylamine); 5 to 40% B in A; Rt: 8.77 min

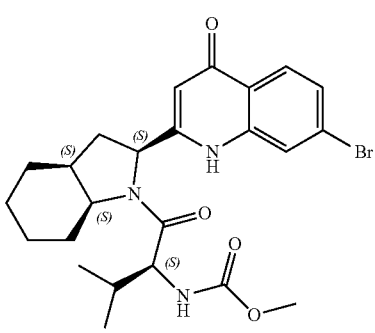

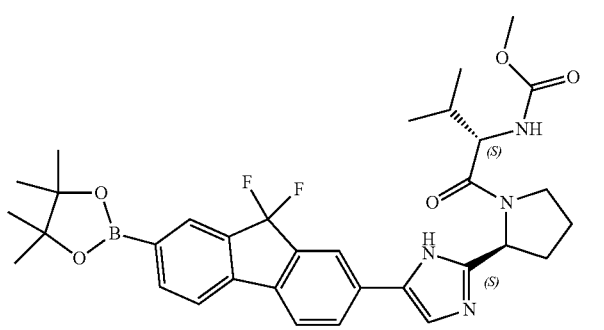

SC-7

Pd(dppf)Cl₂, 2N Na₂CO₃, dioxane, refluxed

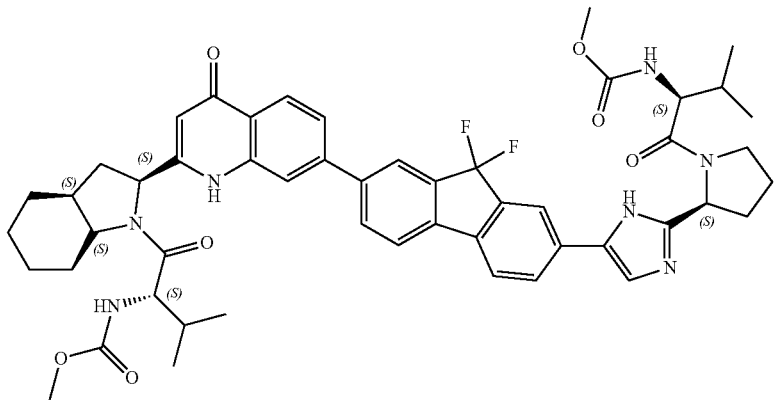

6

To a stirred solution of compound QO-8 (900 mg, 1.78 mmol), compound SC-7 (922 mg, 1.49 mmol) and Pd(dppf)Cl$_2$ (100 mg, 1.9 mmol) in dry THF (20 mL) was added Na$_2$CO$_3$ (10 mL, 2N). The reaction mixture was stirred at refluxed for 20 minutes, quenched with water (20 mL), and extracted with ethyl acetate (3×10 mL). The combined organic layer was washed with brine, dried on Na$_2$SO$_4$ and after filtration the obtained filtrate was concentrated in vacuo. The obtained residue was purified by high-performance liquid chromatography (Column: Phenomenex Synergi C18 150*20 mm*5um. A: H$_2$O+0.1% TFA B: MeCN. FlowRate (mL/min): 40). The pure fractions was collected and neutralized by saturated NaHCO$_3$. The organic solvent was concentrated in vacuo. The precipitate was filtered, washed with H$_2$O (10 mL) and dried under high vacuum resulting in compound 6 (450 mg)

Method H; Rt: 3.68 min. m/z: 818.5 (M+H)$^+$ Exact mass: 817.4;

SFC: Column: OJ-H 250 mm×4.6 mm; 5 um. Flow: 2.35 mL/min, Mobile phase: A: CO$_2$ B: MeOH (0.05% Diethylamine); 5 to 40% B in A; Rt: 8.24 min $^1$H NMR (600 MHz, DMSO-d$_6$) δ ppm 0.88 (d, J=6.5 Hz, 3 H), 0.88 (d, J=6.7 Hz, 3 H), 0.92 (d, J=6.6 Hz, 3 H), 0.95 (d, J=6.7 Hz, 3 H), 1.19-1.36 (m, 3 H), 1.45 (d, J=11.0 Hz, 1 H), 1.54 (q, J=12.0 Hz, 1 H), 1.60-1.69 (m, 1 H), 1.70-1.80 (m, 2 H), 1.89-2.09 (m, 5 H), 2.10-2.21 (m, 2 H), 2.31-2.44 (m, 2 H), 3.54 (s, 3 H), 3.56 (s, 3 H), 3.83 (t, J=6.2 Hz, 2 H), 3.95 (t, J=8.8 Hz, 1 H), 4.08 (t, J=8.4 Hz, 1 H), 4.48 (dt, J=11.0, 6.3 Hz, 1 H), 4.79 (t, J=8.9 Hz, 1 H), 5.09 (dd, J=7.0, 3.4 Hz, 1 H), 5.88 (s, 1 H), 7.34 (d, J=8.5 Hz, 1 H), 7.57 (d, J=7.9 Hz, 1 H), 7.71 (d, J=8.8 Hz, 1 H), 7.72 (s, 1 H), 7.84 (br. s., 1 H), 7.86 (d, J=7.9 Hz, 1 H), 7.93-8.00 (m, 3 H), 8.05 (s, 1 H), 8.08 (s, 1 H), 8.12 (d, J=8.4 Hz, 1 H), 11.76 (br. s., 1 H), 11.96 (br. s., 1 H)

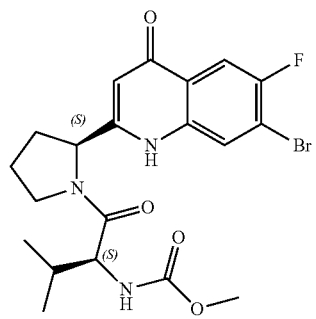

QO-10

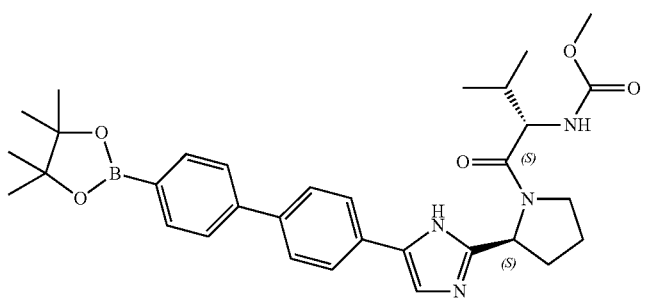

SC-11

→ Pd(PPh$_3$)$_4$, Na$_2$CO$_3$, toluene ethanol, H$_2$O, 100° C., 2h

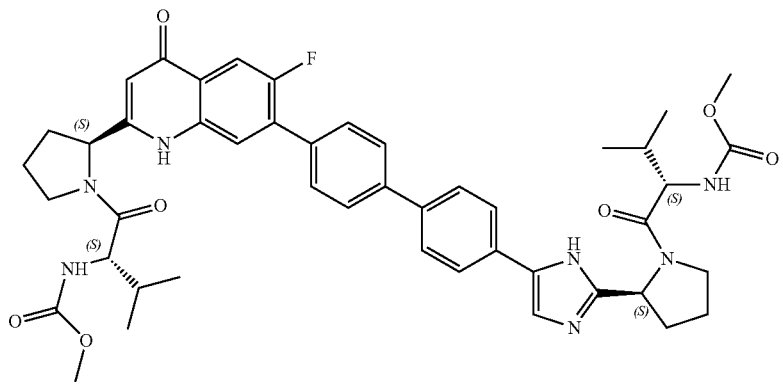

7

A mixture of compound QO-10 (0.12 g, 0.26 mmol), compound SC-11 (0.15 g, 0.26 mmol), Pd(PPh$_3$)$_4$ (0.030 g, 0.026 mmol) and Na$_2$CO$_3$ (0.22 g, 2.05 mmol) in a mixture of toluene, ethanol and H$_2$O (1:1:1, 4.5 mL) was stirred for 2 hours at 100° C. under N$_2$ atmosphere. The volatiles were removed in vacuo. Dichloromethane (15 mL) and water (10 mL) were added. The organic layer was separated and dried over Na$_2$SO$_4$. The solvent was removed in vacuo. The residue was purified by silica gel column chromatography (gradient eluent: first: petroleum ether:EtOAc: from 100:0 to 0:100, then EtOAc:methanol: from 100:0 to 10:1). The obtained solid was washed with acetonitrile and co-evaporated with methanol. The obtained solid was further purified by supercritical fluid chromatography (Columns: OD-3 150×4.6 mm I.D., 3 um, Flow: 2.5 mL/min, Mobile phase: 40% methanol (0.05% Diethylamine) in CO$_2$), resulting in compound 7 (0.1 g) as a white powder. Method H; Rt: 3.39 min. m/z: 834.5 (M+H)$^+$ Exact mass: 833.4 SFC: Column: OD-H 150 mm×4.6 mm; 3 um. Flow: 2.5 mL/min, Mobile phase: A: CO$_2$ B: MeOH (0.05% Diethylamine); 40% B in A; Rt: 6.56 min

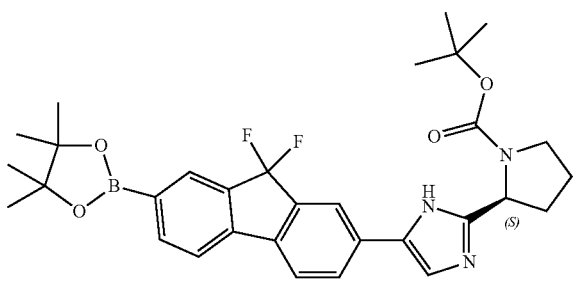

SC-5

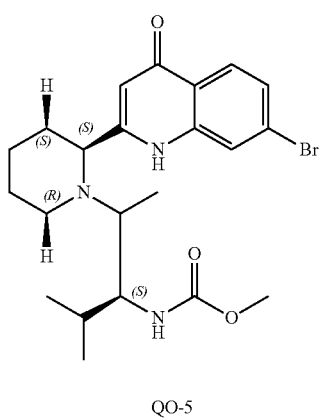

QO-5

1) Pd(PPh$_3$)$_4$, Na$_2$CO$_3$, toluene, ethanol H$_2$O, reflux.

2) HCl/dioxane, CH$_2$Cl$_2$
3) EDCl, HOBt, DIPEA, CH$_2$Cl$_2$

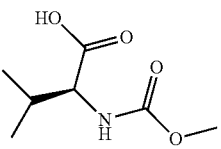

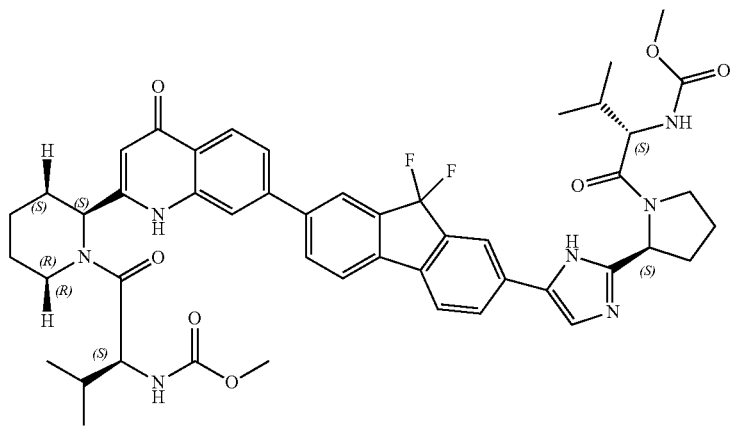

8

Compound QO-15 (0.30 g, 0.63 mmol), compound SC-5 (0.35 g, 0.63 mmol), Pd(PPh₃)₄ (0.22 g, 0.19 mmol) and Na₂CO₃ (0.27 g, 2.5 mmol) in toluene (3 mL), ethanol (3 mL) and H₂O (3 mL) were refluxed under N₂ for 12 hours. The volatiles were removed in vacuo. The mixture was extracted with CH₂Cl₂ (2×10 mL). The organic layers were washed with brine, dried and evaporated in vacuo resulting in a residue (0.5 g). This residue (0.50 g) in CH₂Cl₂ (5 mL) was stirred at 0° C. 4 N HCl/dioxane (5 mL) was added. The mixture was stirred for 1 hour at 20° C. and the volatiles were removed in vacuo, resulting in a residue (0.50 g). To this residue (0.5 g) in CH₂Cl₂ (5 mL), (S)-2-(methoxycarbonylamino)-3-methylbutanoic acid (0.13 g, 0.76 mmol), EDCI (0.22 g, 1.14 mmol) and HOBt (0.043 g, 0.32 mmol) were added and the mixture was stirred at 0° C. Next, DIPEA (0.4 g, 3.2 mmol) was added. The mixture was stirred for 2 hour at 20° C. and subsequently washed with H₂O (2×), and brine, dried on Na₂SO₄ and the solvent was removed in vacuo. The obtained residue was purified by high-performance liquid chromatography (C18, eluent: CH₃CN/H₂O from 15/85 to 35/65 with 0.1% CF₃COOH as buffer). The pure fractions were collected and the mixture was basified with NaHCO₃ to pH=9. The organic solvent was evaporated and the mixture was filtered off. The solid was dried and evaporated in vacuo resulting in compound 8 (140 mg). Method H; Rt: 3.52 min. m/z: 890.3 (M+H)⁺ Exact mass: 889.4; SFC: Column: AS-H 250 mm×4.6 mm; 3 um. Flow: 2.5 mL/min, Mobile phase: A: CO₂ B: MeOH (0.05% Diethylamine); 40% B in A; Rt: 2.9 min; SFC: Column: OD-3 150 mm×4.6 mm; 3 um. Flow: 2.5 mL/min, Mobile phase: A: CO₂ B: EtOH (0.05% Diethylamine); 40% B in A; Rt: 5.2 min

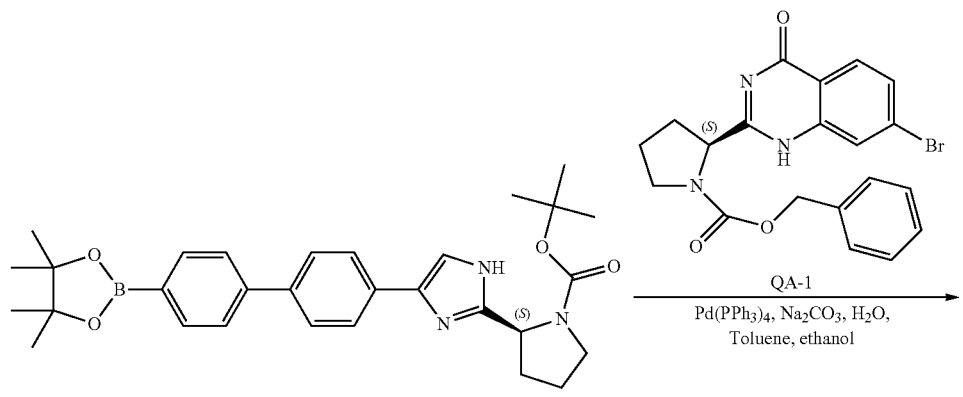

SC-9

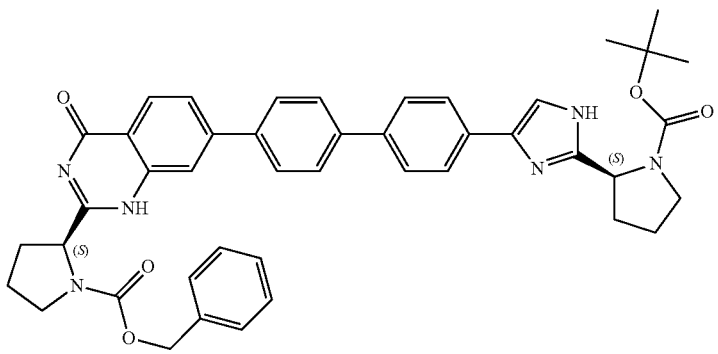

9

A solution of Na₂CO₃ (0.24 g, 2.3 mmol) in H₂O (6 mL) was added to a mixture of compound SC-9 (0.6 g, 1.16 mmol), compound QA-1 (0.5 g, 1.16 mmol), ethanol (6 mL) and toluene (12 mL). Pd(PPh₃)₄ (55 mg, 0.058 mmol) was added to the mixture in one portion under nitrogen. The mixture was stirred for 10 hours at 90° C. Then the solution was cooled to room temperature and filtered. The filtrate was concentrated in vacuo. The obtained residue was dissolved in CH₂Cl₂ (20 mL) and washed with water (3×10 mL). The solution was dried over Na₂SO₄ and concentrated under reduced pressure. The residue was purified by silica gel column chromatography (gradient eluent: EtOAc:dichloromethane=1:3 to 2:1 and EtOAc:MeOH=100:1 to 100:5). The desired fraction was collected, the solvent was removed in vacuo and the obtained residue was dried in vacuo resulting in compound 9 (0.52 g). Method A2; Rt: 1.03 min. m/z: 737.3 (M+H)⁺ Exact mass: 736.3

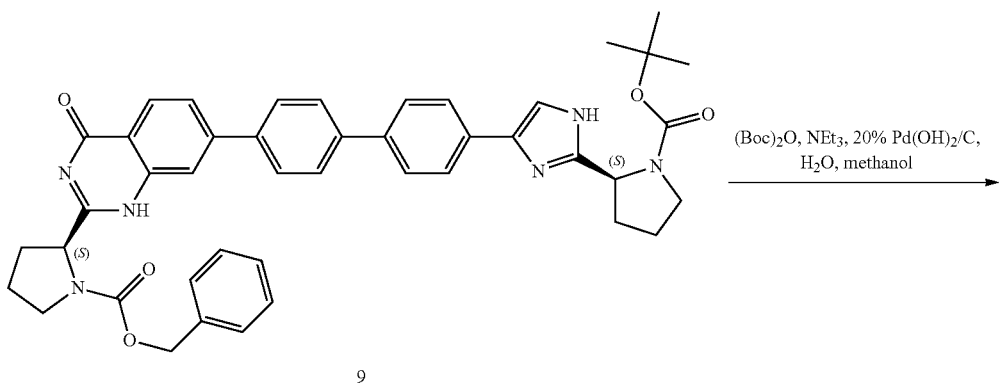

9

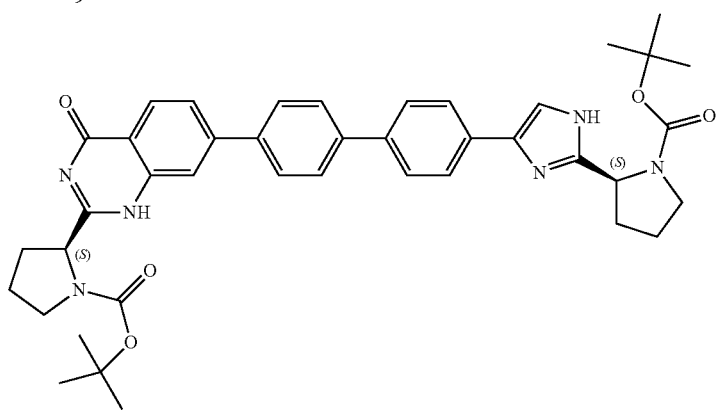

10

A mixture of compound 9 (0.52 g, 0.71 mmol), (Boc)₂O (0.307 g, 1.41 mmol), NEt₃ (0.212 g, 2.1 mmol) and 20% Pd(OH)₂/C (0.5 g) in methanol (5 mL) was hydrogenated (1 atm) at 10° C. for 1.5 hours. The mixture was filtrated and the volatiles were removed in vacuo. The residue was dissolved in CH₂Cl₂ (10 mL) and washed with H₂O (5 mL). The organic layer was dried over Na₂SO₄ and evaporated in vacuo. The residue was washed with tert-butyl methyl ether (3 mL). The solid was filtrated and dried under high vacuum resulting compound 10 (0.47 g). Method A2; Rt: 1.03 min. m/z: 703.3 (M+H)⁺ Exact mass: 702.4

HCl (5 mL) aqueous solution. The organic layer was separated, washed with NaHCO₃ saturated aqueous and brine, and concentrated in vacuo to obtain crude compound. The crude mixture was purified by preparative high-performance liquid

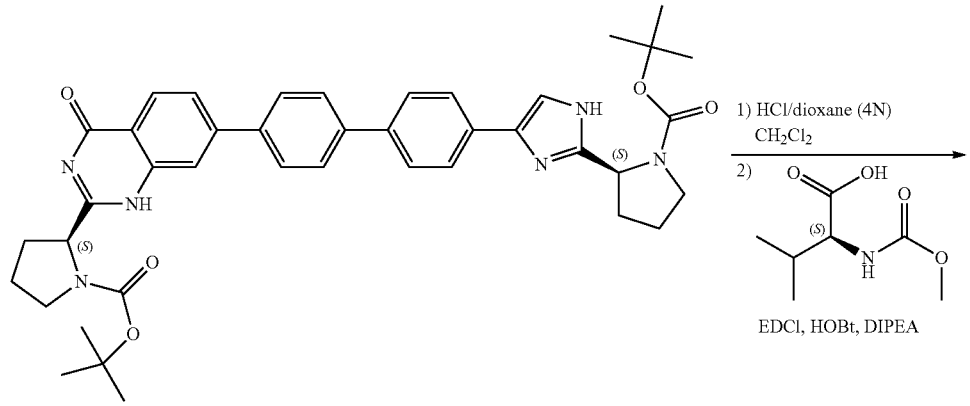

10

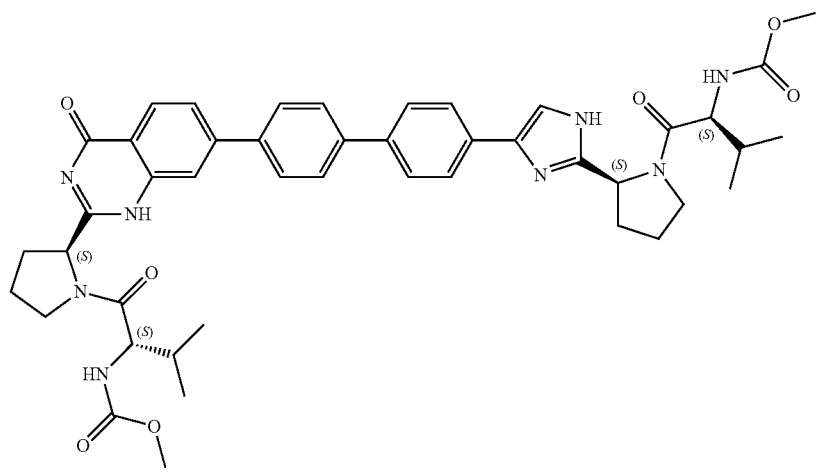

11

Compound 10 (0.47 g, 0.67 mmol) was dissolved in CH₂Cl₂ (5 mL) and HCl/dioxane (4N) (0.5 mL, 2 mmol) was added dropwise at 0° C. The mixture was stirred at 10° C. for 1 hour. The solvent was removed in vacuo and the obtained residue was solidified with t-butyl methyl ether (2 mL). The solid was filtered and dried under high vacuum resulting in a yellow powder. Method A2; Rt: 0.79 min. m/z: 503.1 (M+H)⁺ Exact mass: 502.3. This powder was added to a solution that was obtained by treating (S)-2-(methoxycarbonylamino)-3-methylbutanoic acid (0.28 g, 1.61 mmol) in acetonitrile (5 mL) with EDCI (0.31 g, 1.61 mmol) and HOBt (0.217 g, 1.61 mmol) at 20° C. for 1 hour. The slurry was cooled to 0° C. and DIPEA (0.35 g, 2.7 mmol) was added. The mixture was stirred at room temperature for 15 hours. The mixture was concentrated and diluted with CH₂Cl₂ (20 mL) and of 1 N chromatography (eluent: CH₃CN/H₂O=30/70 to 60/40, 0.1% CF₃COOH). The desired fraction was collected and the pH value of the solution was adjusted to about 8 by adding solid NaHCO₃. The excess acetonitrile was removed under reduced pressure. The aqueous layer was extracted with CH₂Cl₂ (3×50 mL), the organic layers were combined and dried on Na₂SO₄. The obtained solution was concentrated and the residue was further dried in vacuo, resulting in compound 11 (0.1 g). Method B; Rt: 5.06 min. m/z: 817.3 (M+H)⁺ Exact mass: 816.4, SFC: Column: OD-H 250 mm×4.6 mm; 5 um. Flow: 2.35 mL/min, Mobile phase: A: CO₂ B: MeOH (0.05% Diethylamine); 40% B in A; Rt: 7.5 min; SFC: Column: OD-H 250 mm×4.6 mm; 5 um. Flow: 2.35 mL/min, Mobile phase: A: CO₂ B: EtOH (0.05% Diethylamine); 40% B in A; Rt: 5.25 min

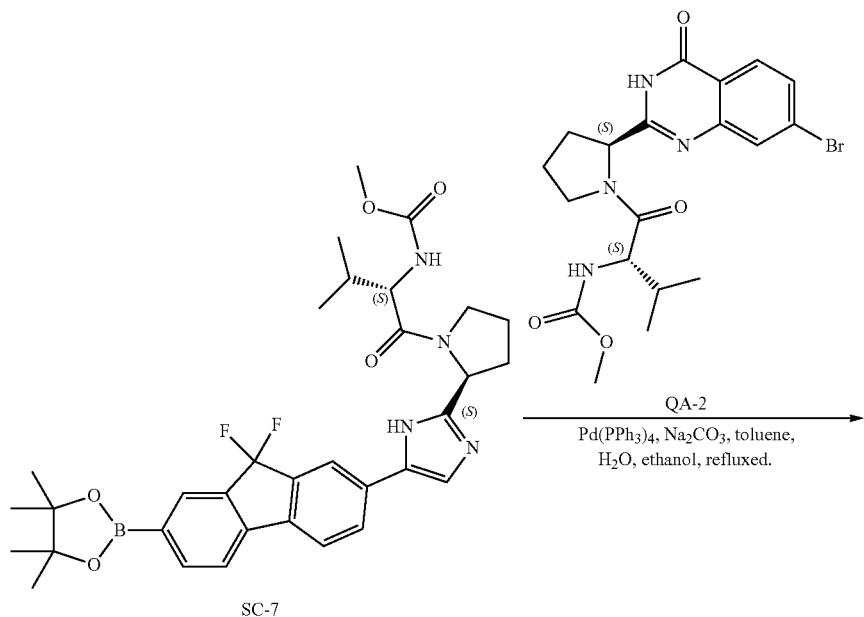

SC-7

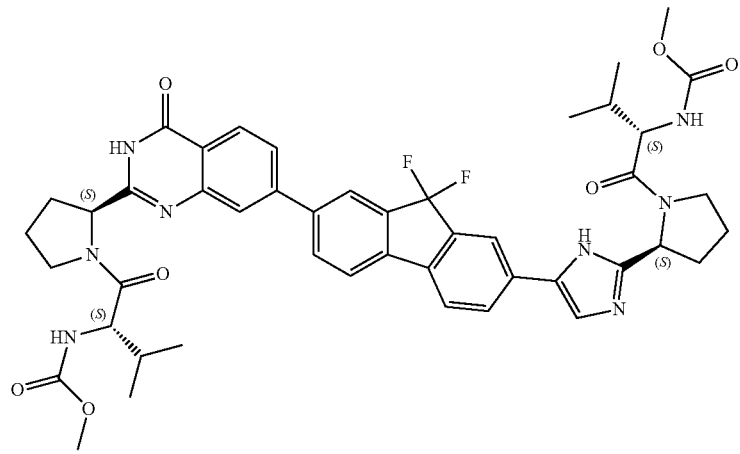

12

Na₂CO₃ (1.7 g, 16 mmol, 10 eq) in H₂O (10 mL) was added to the mixture of compound SC-7 (1 g, 1.6 mmol, 1 eq), compound QA-2 (0.73 g, 1.6 mmol, 1 eq), toluene (10 mL) and ethanol (10 mL). Pd(PPh₃)₄ (0.18 g, 0.16 mmol, 0.1 eq) was added. The mixture was stirred at 100° C. for 3 hour under N₂ atmosphere. CH₂Cl₂ (10 mL) and H₂O (5 mL) were added. The organic layer was separated, dried on Na₂SO₄ and evaporated resulting in a crude residue (3 g). A part of this crude material (0.9 g) was purified by high-performance liquid chromatography (Column: Grace Vydac 250*20 mm*5um Mobile phase A: water; Mobile phase B: acetonitrile; Flow rate: 30 mL/min; Gradient: 35-50% B (v/v) from 0 to 11 min). The pure fraction was collected and evaporated in vacuo resulting in compound 12 (0.1 g) Method H; Rt: 3.56 min. m/z: 865.4 (M+H)⁺ Exact mass: 864.4; SFC: Column: OD-H 250 mm×4.6 mm; 5 um. Flow: 2.35 mL/min, Mobile phase: A: CO₂ B: EtOH (0.05% Diethylamine); 40% B in A: Rt: 4.80 min; SFC: Column: AS-H 250 mm×4.6 mm; 5 um. Flow: 2.35 mL/min, Mobile phase: A: CO₂ B: MeOH (0.05% Diethylamine); 5 to 40% B in A; Rt: 9.0 min

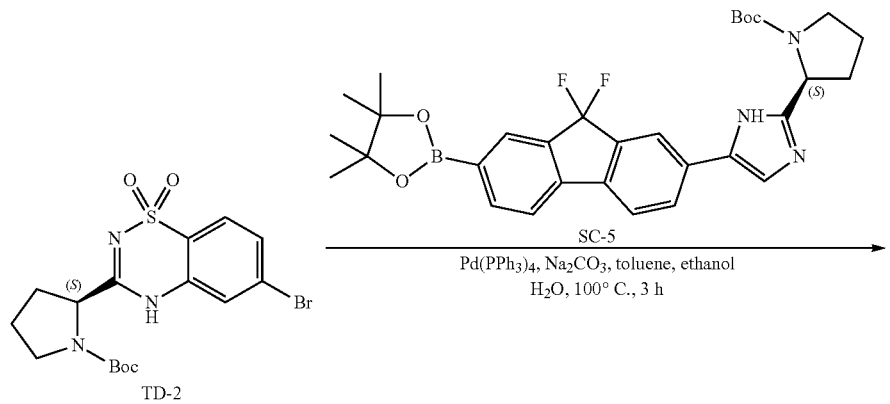

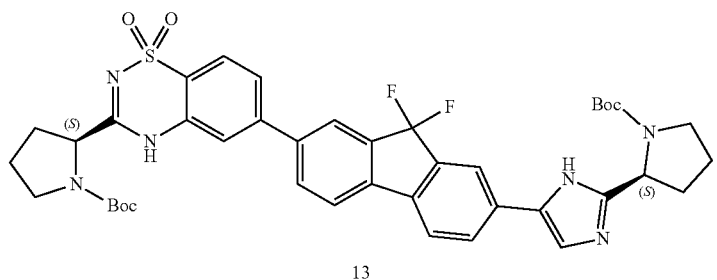

Na$_2$CO$_3$ (0.94 g, 8.9 mmol) in H$_2$O (5 mL) was added to a mixture of compound SC-5 (0.5 g, 0.89 mmol,) and compound TD-2 (0.38 g, 0.89 mmol) in toluene (5 mL) and ethanol (5 mL). N$_2$ was bubbled through the solution and then. Pd(PPh$_3$)$_4$ (0.1 g, 0.089 mmol) was added. The mixture was stirred at 100° C. for 3 hours under N$_2$. atmosphere. CH$_2$Cl$_2$ (20 mL) and H$_2$O (10 mL) were added and the after separation, the organic layer was dried on Na$_2$SO$_4$ and the solvent removed in vacuo. The residue was purified by silica gel column chromatography (Eluent: ethyl acetate: petroleum from 75% to 100%), resulting in compound 13 (0.5 g). Method A2; Rt: 1.05 min. m/z: 787.4 (M+H)$^+$ Exact mass: 786.3;

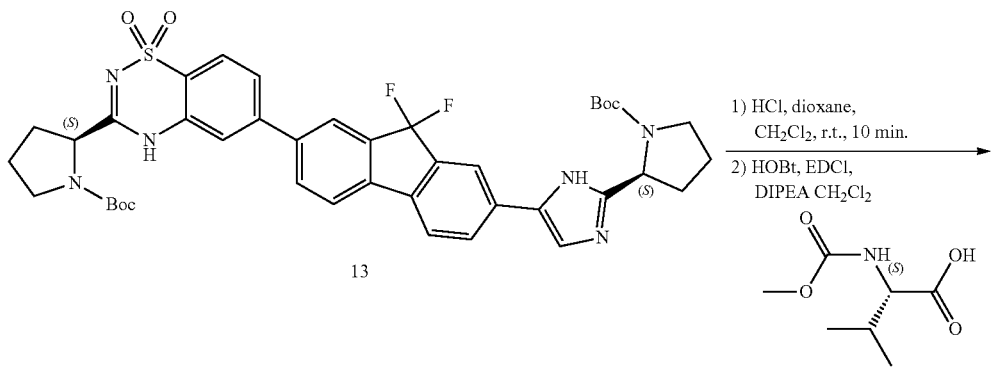

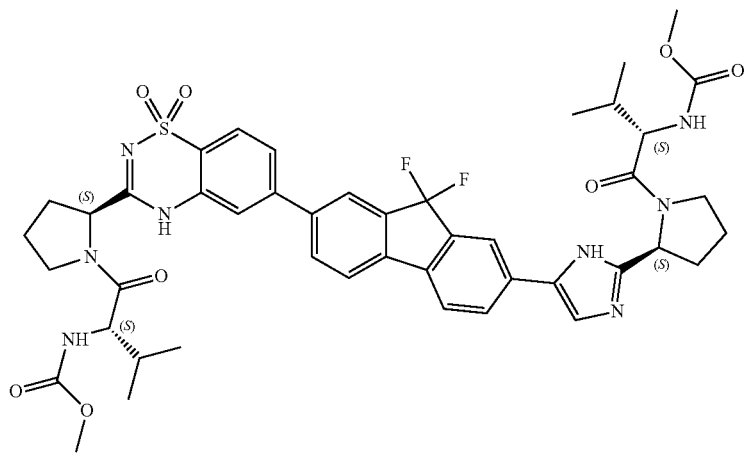

14

HCl/dioxane (2 mL) was added to the mixture of compound 13 (0.5 g, 0.64 mmol, 1 eq), and CH$_2$Cl$_2$ (5 mL) at 0° C. The mixture was stirred at 20° C. for 10 min. The solvent was removed in vacuo. Method A2; Rt: 0.84 min. m/z: 587.1 (M+H)$^+$ Exact mass: 586.2; To the obtained residue in CH$_2$Cl$_2$ (5 mL), (S)-2-(methoxycarbonylamino)-3-methylbutanoic acid (0.24 g), EDCI (0.27 g, 1.4 mmol) and HOBt (0.19 g, 1.4 mmol) were added, the mixture was cooled to 0° C. and DIPEA (1.1 mL, 6.4 mmol, 10 eq) was added. The mixture was next stirred at 20° C. for 12 hours. The mixture was diluted with CH$_2$Cl$_2$ (20 mL) and H$_2$O (5 mL). The organic layer was separated and washed with saturated aqueous NaHCO$_3$ (5 mL), brine and dried over Na$_2$SO$_4$. The solvent was removed in vacuo. The residue was purified by high-performance liquid chromatography (Column: Grace Vydac 250*20 mm*5 u; Mobile phase A: water (containing 0.075% TFA, V/V %) Mobile phase B: acetonitrile (containing 0.025% TFA, V/V %; Flow rate: 30 mL/min; Gradient: 35-50% B (v/v) from 0 to 11 min). The relevant fraction was collected and basified with saturated NaHCO$_3$ solution to pH=8. The volatiles were removed in vacuo. The residue was extracted with CH$_2$Cl$_2$ (2×10 mL). The organic layer was washed with brine (10 mL) and dried over Na$_2$SO$_4$. The solvent was removed in vacuo. The residue was separated by Supercritical fluid chromatography. (Column: AS 250 mm×30 mm, Sum; Mobile phase: A: Supercritical CO$_2$, B: MeOH (0.05% Diethylamine, A:B=60:40 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm). The relevant fraction was collected and the solvent removed in vacuo. The residue was dissolved in CH$_2$Cl$_2$ (5 mL) and washed with saturated NaHCO$_3$ solution (2×5 mL). The organic layer was dried over Na$_2$SO$_4$ and evaporated. The residue was washed with t-butyl methyl ether (2 mL) and filtrated. The solid was dried under high vacuum, resulting in compound 14 (0.153 g). Method C; Rt: 3.98 min. m/z: 901.3 (M+H)$^+$ Exact mass: 900.3; SFC: Column: OJ-H 250 mm×4.6 mm; 5 um. Flow: 2.35 mL/min, Mobile phase: A: CO$_2$ B: MeOH (0.05% Diethylamine); 5 to 40% B in A; Rt: 7.44 min SFC: Column: AS-H 250 mm×4.6 mm; 5 um. Flow: 2.35 mL/min, Mobile phase: A: CO$_2$ B: EtOH (0.05% Diethylamine); 5 to 40% B in A; Rt: 8.90 min

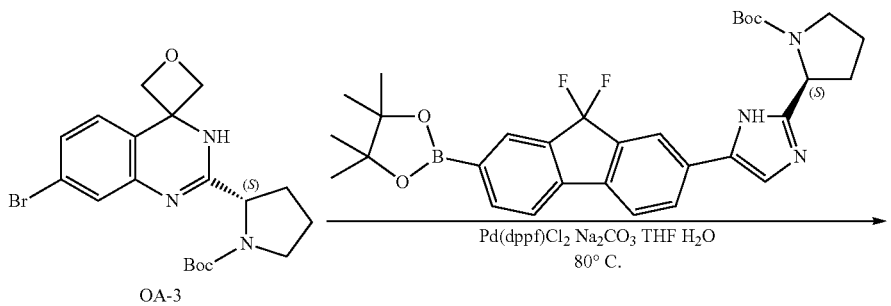

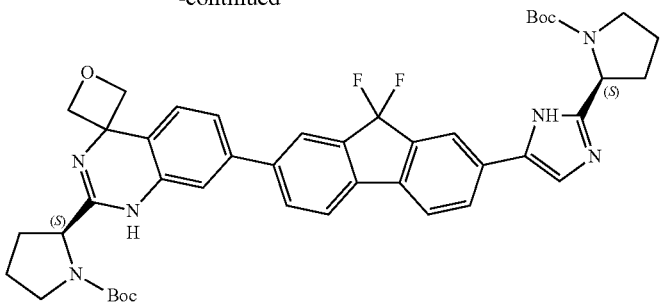

15

To compound OA-3 (0.49 g, 1.16 mmol), (S)-tert-butyl 2-(5-(9,9-difluoro-7-(4,4,5,5-tetramethyl-1,3,2-dioxaborolan-2-yl)-9H-fluoren-2-yl)-1H-imidazol-2-yl)pyrrolidine-1-carboxylate (0.78 g, 1.4 mmol,), Pd(dppf)Cl₂ (45 mg, 0.058 mmol,), THF (10 mL) and aqueous Na₂CO₃ (2 mL, 2N) were added. The mixture was flushed with nitrogen gas (3×). The reaction mixture was stirred at 80 degree for 15 minutes, quenched with water (10 mL) and extracted with CH₂Cl₂ (2×5 mL). The phases were separated and the organic phase was washed with brine and dried over Na₂SO₄. After removal of the volatiles, the obtained residue was purified by silica gel column chromatography (eluent: CH₂Cl₂/methanol=10/1) resulting in compound 15 (0.49 g). Method A; Rt: 0.99 min. m/z: 779.4 (M+H)⁺ Exact mass: 778.4;

Compound 15 (0.2 g, 0.28 mmol) was dissolved in CH₂Cl₂ (5 mL) and TFA (5 mL,) was slowly added. The reaction was stirred at room temperature for 30 minutes and the volatiles were removed, resulting in a residue (0.19 g). To a solution of part of the obtained residue (45 mg) in CH₂Cl₂ (5 mL) were added (S)-2-(methoxycarbonylamino)-3-methylbutanoic acid (26 mg, 0.15 mmol), EDCI (29 mg, 0.15 mmol), HOBt (8 mg, 0.058 mmol) and NEt₃ (23 mg, 0.23 mmol) The mixture was stirred at room temperature overnight. The mixture was washed with water (10 mL) and the water layer was extracted with CH₂Cl₂ (2×10 mL). The combined organic layer was dried on Na₂SO₄ and after filtration, the filtrate was concentrated, resulting in a residue. The obtained residue was purified by high-performance liquid chromatography (Column:

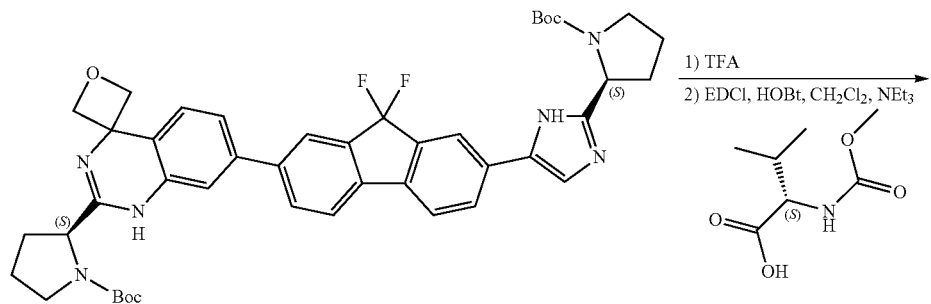

15

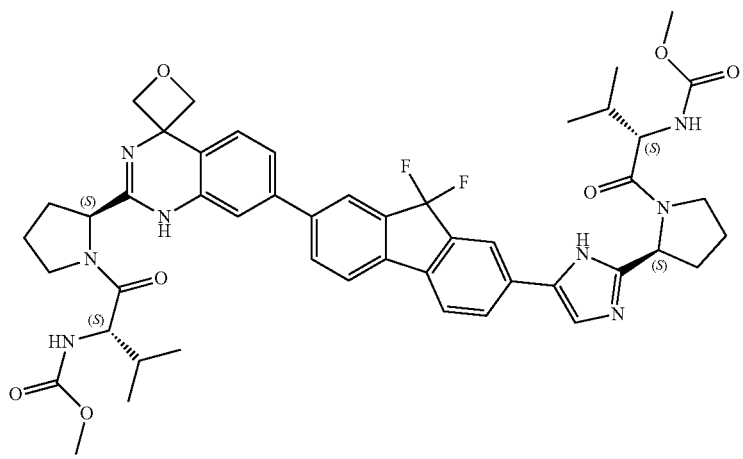

16

Phenomenex Synergi C18 150*30 mm*4 um. Method: From 30 to 50% B in A in-12 minutes. A: H₂O+0.1% TFA B: MeCN. FlowRate (mL/min): 25), to the fractions containing product, Na₂CO₃ was added until pH value was 9. The organic solvent was removed in vacuo and the water layer was extracted with CH₂Cl₂ (2×20 mL). The organic layer was separated, dried on Na₂SO₄, and after filtration, the solvent was removed resulting in compound 16 (11 mg). Method B; Rt: 4.58 min. m/z: 892.4 (M+H)⁺ Exact mass: 893.3; SFC: Column: OD-H 250 mm×4.6 mm; 5 um. Flow: 2.35 mL/min, Mobile phase: A: CO₂ B: EtOH (0.05% Diethylamine); 40% B in A; Rt: 6.17 min

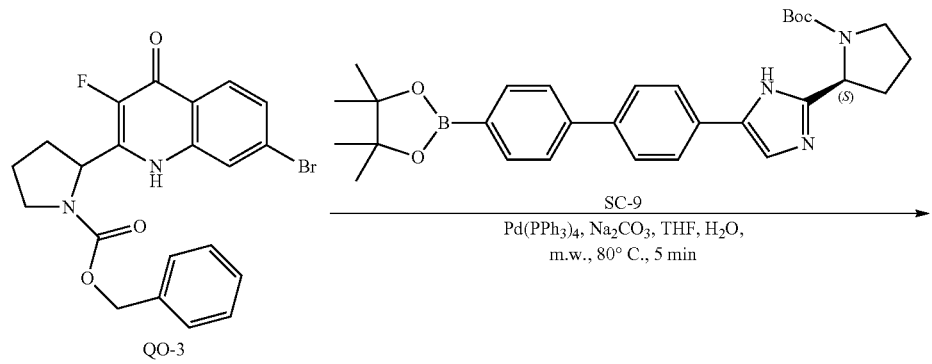

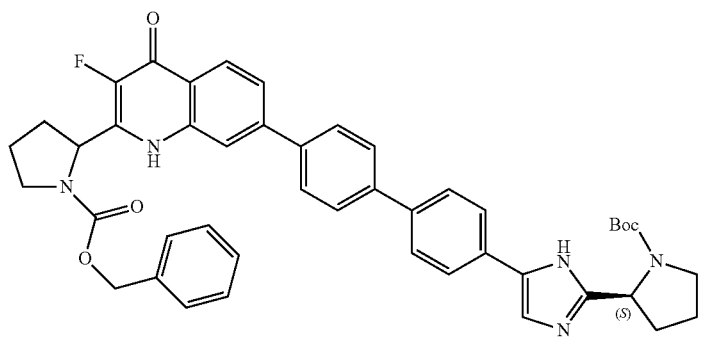

Compound QO-3 (0.2 g, 0.44 mmol), compound SC-9 (0.25 g, 0.49 mmol), Pd(PPh₃)₄ (0.10 g, 0.088 mmol) and Na₂CO₃ (0.21 g, 1.98 mmol) in THF (8 mL) and H₂O (2.4 mL) were stirred at 80° C. under microwave irradiation for 5 minutes. The solvent was removed in vacuo, the obtained residue was dissolved in CHCl₃ and filtered. The filtrate was concentrated and purified by preparative TLC. (Eluent: ethyl acetate/methanol, 10:1), resulting in compound 17 (0.25 g).

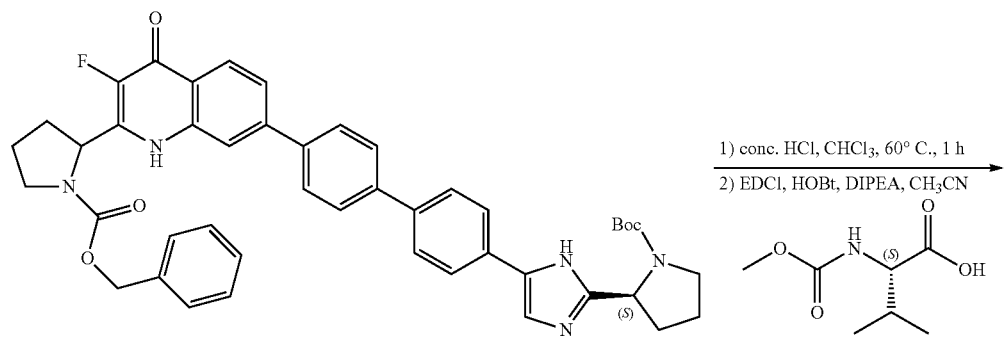

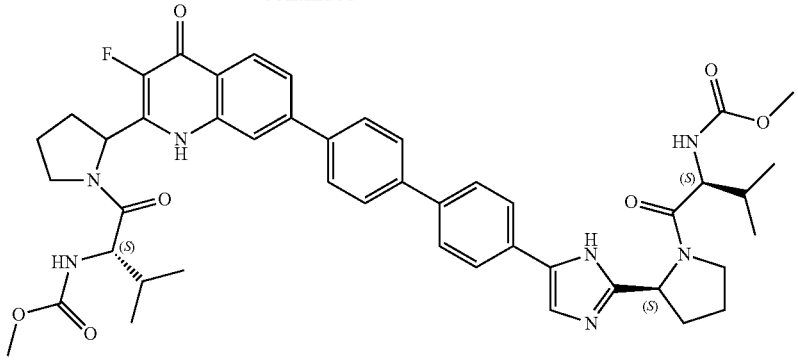

18

Compound 17 (0.24 g, 0.32 mmol) in CHCl₃ (10 mL) and concentrated HCl (10 mL) were stirred at 60° C. in a seal tube for 2 hours. The aqueous layer was separated and concentrated in vacuo. The residue (0.2 g) was co-evaporated with toluene and THF and added to a solution that was formed by adding EDCI (0.25 g, 1.32 mmol) and HOBt (0.18 g, 1.32 mmol) to a solution of (S)-2-(methoxycarbonylamino)-3-methylbutanoic acid (0.23 g, 1.32 mmol) in CH₃CN (5 mL) and stirring at 10° C. for 1 hour. The mixture was then cooled to 0° C. and DIPEA (1 mL, 5.6 mmol) was added. The mixture was stirred at 10° C. overnight. The solvent was removed in vacuo and the obtained compound 18 (mixture of diastereoisomers 18a and 18b) was purified by preparative HPLC. (C18, eluent: CH₃CN, H₂O, TFA, 40:60:0.05) Two fractions were obtained. The fractions were neutralized with saturated NaHCO₃. The organic solvent was removed in vacuo. The resulting precipitate was filtered and dried under high vacuum, resulting in 18a (33 mg; e.e. 99%) of 18b (33 mg; e.e. 90%) were obtained. Compound 18b was purified by SFC. Column: OD 250 mm*30 mm, 5 um; Mobile phase: A: Supercritical CO₂, B: EtOH; 0.05% Diethylamine;, A:B=60:40 at 50 mL/min; Column Temp: 38° C.; Nozzle Pressure: 100 Bar; Nozzle Temp: 60° C.; Evaporator Temp: 20° C. Trimmer Temp: 25° C.; Wavelength: 220 nm) The collected fractions were combined and concentrated in vacuo. The residue was washed with saturated NaHCO₃ and dried under high vacuum. Resulting in compound 18b was obtained. (26 mg, e.e. 99%)

18a; Method B; Rt: 4.75 min. m/z: 833.4 (M+H)⁺ Exact mass: 834.6; SFC: Column: OD-3 150 mm×4.6 mm; 3 um. Flow: 2.5 mL/min, Mobile phase: A: CO₂ B: MeOH (0.05% Diethylamine); 40% B in A; Rt: 6.08 min 18b; Method B; Rt: 4.87 min. m/z: 833.4 (M+H)⁺ Exact mass: 834.5; SFC: Column: OD-H 250 mm×4.6 mm; 5 um. Flow: 2.35 mL/min, Mobile phase: A: CO₂ B: EtOH (0.05% Diethylamine); 40% B in A; Rt: 4.25 min

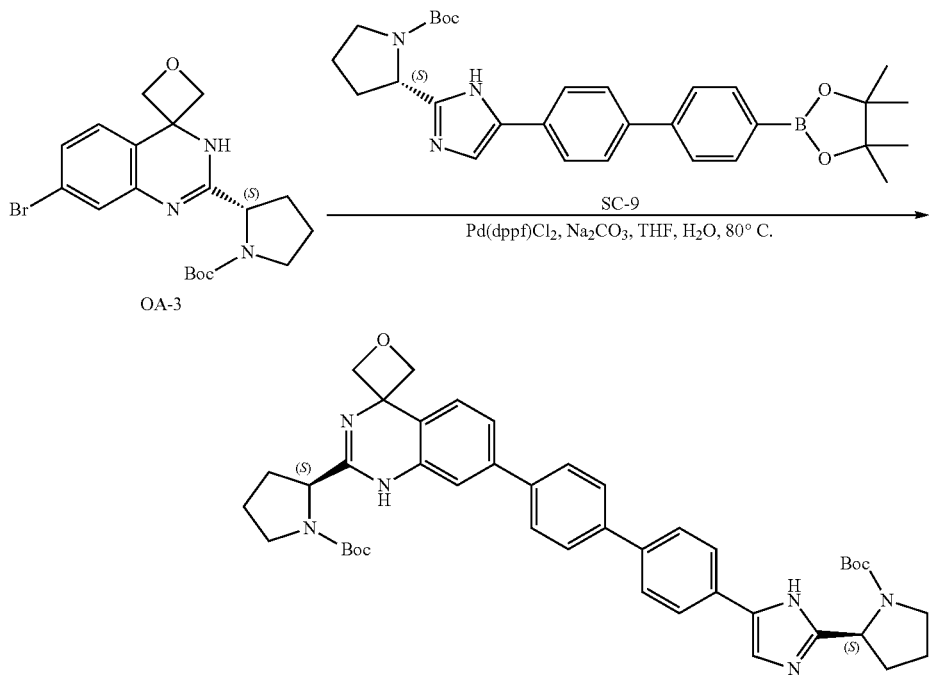

19

A mixture of compound OA-3 (0.46 g, 1.09 mmol), SC-9 (0.67 g, 1.3 mmol), Pd(dppf)Cl$_2$ (45 mg, 0.058 mmol), THF (10 mL) and aqueous Na$_2$CO$_3$ (2 mL, 2N) was flushed with nitrogen gas for three times. The reaction mixture was stirred at 80 degree for 15 minutes. The mixture was quenched with water (10 mL) and extracted with CH$_2$Cl$_2$ (2×5 mL). The phases were separated and the organic phase was washed with brine and dried over Na$_2$SO$_4$. After removal of the volatiles the obtained residue was purified by silica gel column chromatography (eluent: CH$_2$Cl$_2$/methanol=10/1) resulting in compound 19 (0.42 g).

mmol) and NEt$_3$ (60 mg, 0.6 mmol) The mixture was stirred at room temperature overnight. The mixture was washed with water (10 mL) and extracted with CH$_2$Cl$_2$ (2×10 mL). The combined organic layer was dried and concentrated resulting in a residue that was purified by high-performance liquid chromatography (MeCN/H$_2$O (Column: Diamonsil C18 150*20 mm*5 um. Method: From 20 to 40% B in A in 14 min. A: H$_2$O+0.1% TFA B: MeCN. FlowRate (mL/min): 40)) To the fractions containing product, Na$_2$CO$_3$ was added until pH value was 9, the organic solvent was removed, and the water layer was washed with CH$_2$Cl$_2$ (2×20 mL) was. The organic

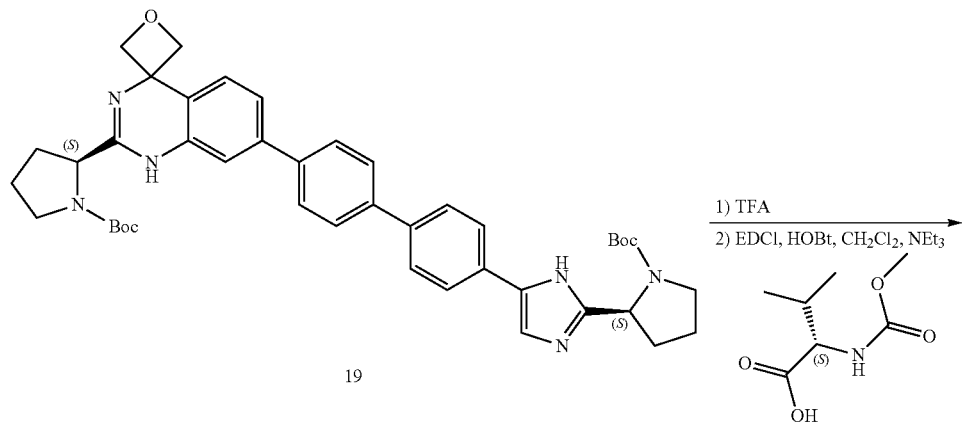

19

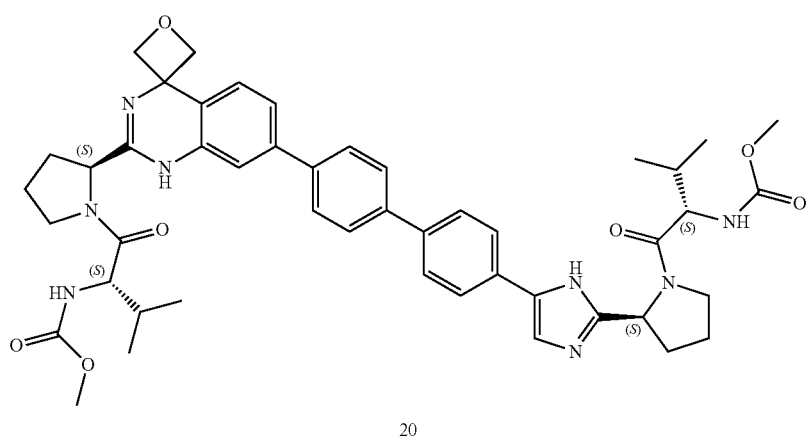

20

Compound 19 (0.2 g, 0.28 mmol) was dissolved in CH$_2$Cl$_2$ (5 mL) and TFA (5 mL,) was slowly added. The reaction was stirred at room temperature for 30 minutes and the mixture was concentrated resulting in a residue (0.19 g). To part of this residue (110 mg) in CH$_2$Cl$_2$ (5 mL) were added (S)-2-(methoxycarbonylamino)-3-methylbutanoic acid (105 mg, 0.60 mmol), EDCI (114 mg, 0.60 mmol), HOBt (13.5 mg, 0.1 layer was separated and concentrated to dryness resulting in compound 20 (40 mg). Method C; Rt: 3.48 min. m/z: 845.5 (M+H)$^+$ Exact mass: 844.4; SFC: Column: OD-H 250 mm×4.6 mm; 5 um. Flow: 2.35 mL/min, Mobile phase: A: CO$_2$ B: MeOH (0.05% Diethylamine); 40% B in A; Rt: 8.48 min

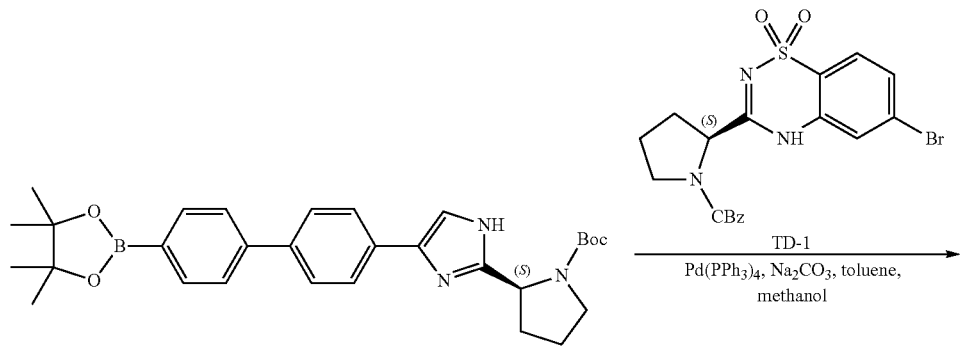

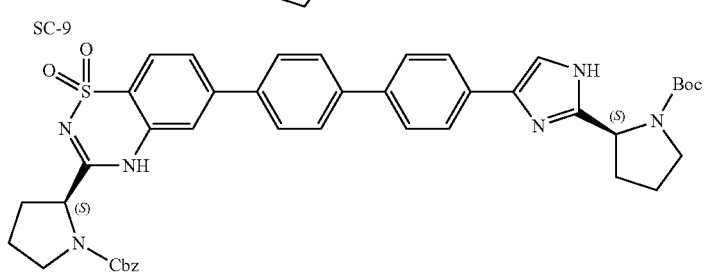

21

Na₂CO₃ (0.4 g, 3.8 mmol, 2 eq) in H₂O (10 mL) was added to the mixture of compound SC-9 (1 g, 1.9 mmol), compound TD-1 (0.9 g, 1.9 mmol), ethanol (10 mL) and toluene (20 mL). Pd(PPh₃)₄ (0.11 g, 0.095 mmol) was added. The mixture was stirred at 90° C. for 10 hour at N₂ protection. The organic solvent was removed in vacuo. The residue was extracted with CH₂Cl₂ (10 mL). The organic layer was washed with brine (5 mL) and dried over Na₂SO₄. The solvent was removed in vacuo. The residue was purified by flash column (Eluent: CH₂Cl₂/Methanol=10:1). The solvent was evaporated resulting in compound 21 (1.7 g)

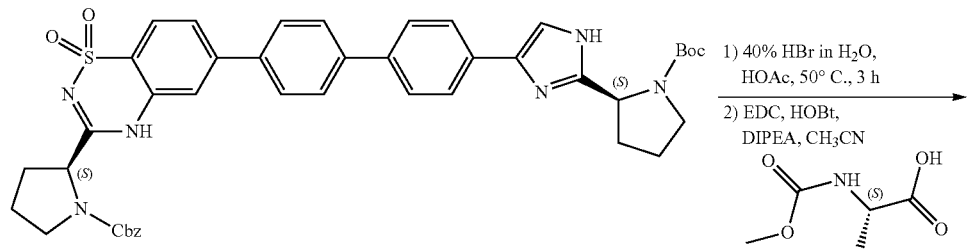

21

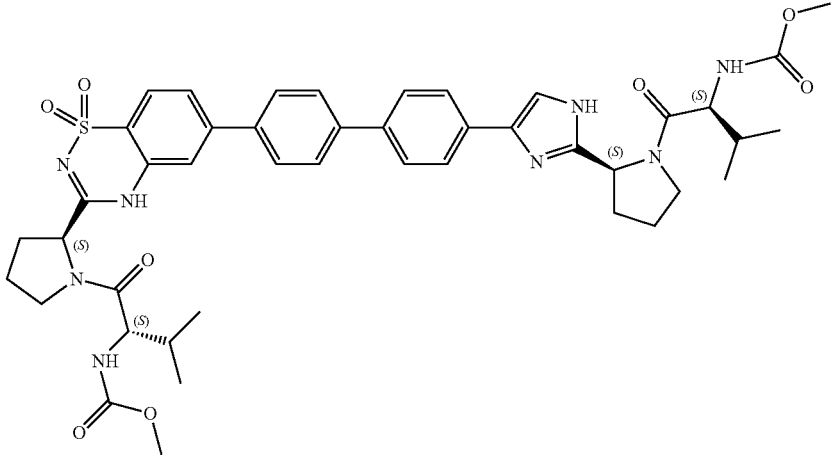

22

Compound 21 (1.7 g, 1.1 mmol) was dissolved in CH$_3$COOH (20 mL). 40% HBr in H$_2$O (10 mL) was added. The mixture was stirred at 50° C. for 3 hour. The solvent was evaporated in vacuo. The residue was washed with the mixture of tert-butyl methyl ether and methanol (1:1). The solid was filtrated and dried under high vacuum resulting in a residue (1.7 g). Part of this residue (0.7 g) was added to a preformed solution formed by adding EDCI (0.46 g, 2.4 mmol) and HOBt (0.32 g, 2.4 mmol) to (S)-2-(methoxycarbonylamino)-3-methylbutanoic acid (0.42 g, 2.4 mmol) in acetonitrile (14 mL) and stirring at 10° C. for 1 hour. The slurry was cooled to 0° C. and DIPEA (1 g, 8 mmol) was added. The mixture was stirred at 10° C. for 12 hours. The solid was filtrated. The filtrate was concentrated and diluted with CH$_2$Cl$_2$ (20 mL) and 1 N HCl (5 mL). The organic layer was separated and washed with saturated aqueous NaHCO$_3$ (5 mL), brine and dried over Na$_2$SO$_4$. The solvent was removed in vacuo. The residue was purified by high-performance liquid chromatography; Column: Grace Vydac 250*20 mm*5um Mobile phase A: water; containing 0.075% TFA, V/V % Mobile phase B: acetonitrile (containing 0.025% TFA, V/V % Flow rate: 30 mL/min; Gradient: 35-50% B (v/v) from 0 to 11 min). The pure fractions were collected and basified with NaHCO$_3$ to pH=8. The volatiles were removed in vacuo. The residue was extracted with CH$_2$Cl$_2$ (2×15 mL). The organic layer was washed with brine (10 mL) and dried over Na$_2$SO$_4$. The solvent was removed in vacuo. The residue was separated by Supercritical fluid chromatography. (Column: AS 250 mm*30 mm, 5um; Mobile phase: A: Supercritical CO$_2$, B: MeOH (0.05% Diethylamine), A:B=60:40 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm). The fractions were collected and the solvent removed in vacuo. The residue was dissolved in CH$_2$Cl$_2$ (5 mL) and washed with saturated NaHCO$_3$ solution (5 mL) and brine (5 mL). The organic layer was dried over Na$_2$SO$_4$ and evaporated resulting in compound 22 (98 mg); Method B; Rt: 4.94 min. m/z: 853.3 (M+H)$^+$ Exact mass: 852.4; SFC: Column: AS-H 250 mm×4.6 mm; 5 um. Flow: 2.5 mL/min, Mobile phase: A: CO$_2$ B: MeOH (0.05% Diethylamine); 40% B in A; Rt: 4.53 min.

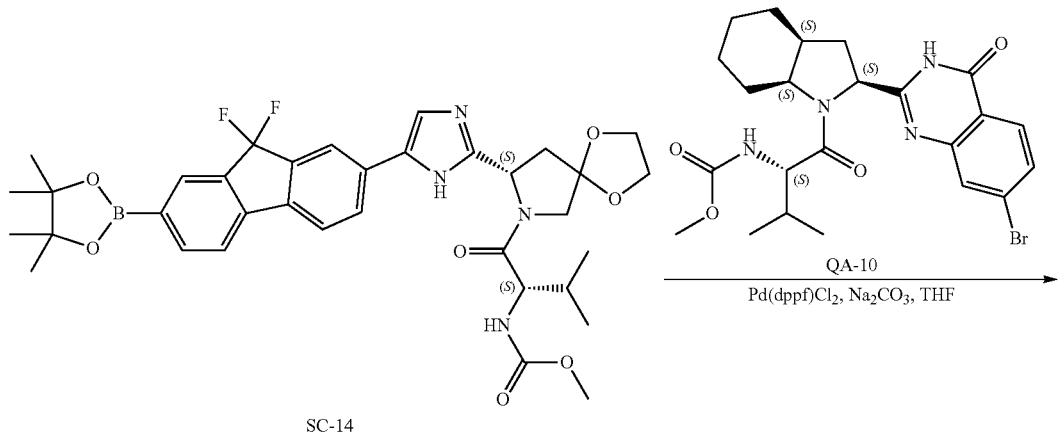

SC-14

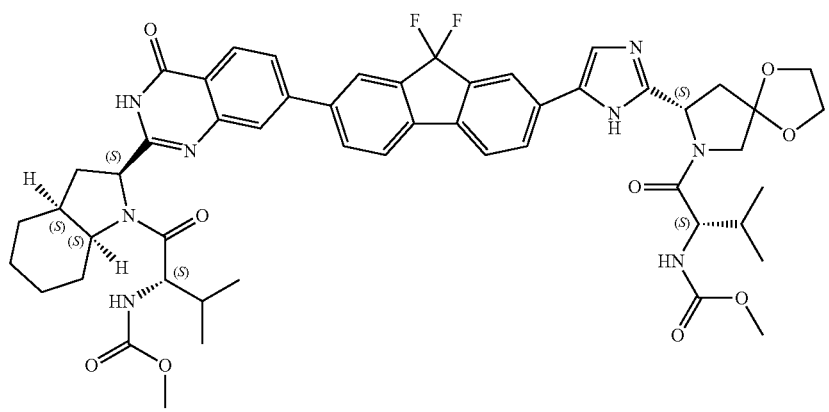

23

To a stirred solution of SC-14 (800 mg, 1.18 mmol), QA-10 (713 mg, 1.42 mmol) and Pd(dppf)Cl$_2$ (100 mg) in dry THF (10 mL), Na$_2$CO$_3$ (5 mL, 2 N aq.) was added. The reaction mixture was stirred at reflux by heating in a pre-heated oil bath at 90° C., for 20 minutes. The mixture was next quenched with water (20 mL) and extracted with ethyl acetate (3×10 mL). The combined organic layers was washed with brine, dried over Na$_2$SO$_4$ and concentrated in vacuo. The obtained residue was purified by high-performance liquid chromatography (Column: Phenomenex Synergi C18 150*20 mm*5um. Method: 34 to 64% B in A: $H_2O$+0.1% TFA B: MeCN. FlowRate (mL/min): 25). The pure fractions were collected and neutralized by saturated $NaHCO_3$. The mixture was concentrated in vacuo. The obtained product was further purified by supercritical fluid chromatography (Column: Chiralpak OD-3 50*4.6 mm I.D., 3 um Mobile phase: A: methanol (0.05% diethylamine), B: $CO_2$, A/B=40/60, Flow rate: 2.5 mL/min, Wavelength: 220 nm). The pure fractions were collected and the volatiles were removed in vacuo. The obtained residue was dissolved in dichloromethane (20 mL). The organic layer was washed with saturated aqueous $NaHCO_3$ (10 mL) and dried over $Na_2SO_4$. The solvent was removed in vacuo, resulting in compound 23 (247 mg). Method B; Rt: 5.84 min. m/z: 977.7 $(M+H)^+$ Exact mass: 976.4; $^1H$ NMR (400 MHz, DMSO-$d_6$) δ ppm 12.29-12.54 (1 H, m), 12.03 (1 H, br. s), 8.12-8.21 (1 H, m), 8.01-8.11 (2 H, m), 7.91-8.01 (3 H, m), 7.79-7.91 (2 H, m), 7.62-7.76 (2 H, m), 7.54 (1 H, d, J=7.3 Hz), 7.32 (1 H, d, J=8.3 Hz), 5.01-5.15 (1 H, m), 4.67-4.81 (1 H, m), 4.37-4.52 (1 H, m), 3.81-4.13 (7 H, m), 3.70-3.80 (1 H, m), 3.54 (6 H, br. s), 2.31-2.46 (3 H, m), 2.16-2.29 (1 H, m), 1.82-2.16 (5 H, m), 1.56-1.82 (3 H, m), 1.37-1.51 (1 H, m), 1.16-1.36 (2 H, m), 0.71-0.99 (12 H, m).

BIOLOGICAL EXAMPLES

Anti-HCV Activity of Compounds of Formula I

Replicon Assay

The compounds of formula (I) were examined for inhibitory activity in the HCV replicon. This cellular assay is based on a bicistronic expression construct, as described by Lohmann et al. (Science (1999) 285: 110-113; Journal of Virology (2003) 77: 3007-3019) with modifications described by Krieger et al. (Journal of Virology (2001) 75: 4614-4624), and Lohmann et al. (Journal of Virology (2003) 77: 3007-3019) for genotype 1b and by Yi et al. (Journal of Virology (2004) 78: 7904-7915) for genotype 1a, in a multi-target screening strategy.

Stable Transfection

The method was as follows. The assay utilized the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an Internal Ribosome Entry Site (IRES) from encephalomyocarditis virus (EMCV), preceded by a reporter portion (FfL-luciferase), and a selectable marker portion (neoR, neomycine phosphotransferase). The construct is flanked by 5' and 3' NTRs (non-translated regions) from HCV type 1b. Continued culture of the replicon cells in the presence of G418 (neoR) is dependent on the replication of the HCV RNA. The stably transfected replicon cells that replicate HCV RNA autonomously and to high levels, encoding inter alia luciferase, were used for screening the antiviral compounds.

The replicon cells were plated in 384 well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound was monitored on the Huh-Luc cells, enabling a dose-response curve for each test compound. $EC_{50}$ values were then calculated, which represent the amount of compound required to decrease the level of detected luciferase activity by 50%, or more specifically, to reduce the ability of the genetically linked HCV replicon RNA to replicate.

Results

Where a compound of formula (I) was tested more than once in the replicon assay, the average of all test results is given in this Table 1.

| STRUCTURE | Compound nr. | HCV-REP-HUH7LUC_$EC_{50}$ (nM) |
|---|---|---|
| (structure shown) | 3 | |
| | 3a | 0.021 |
| | 3b | 1.13 |

-continued

| STRUCTURE | Compound nr. | HCV-REP-HUH7LUC_EC$_{50}$ (nM) |
|---|---|---|
| 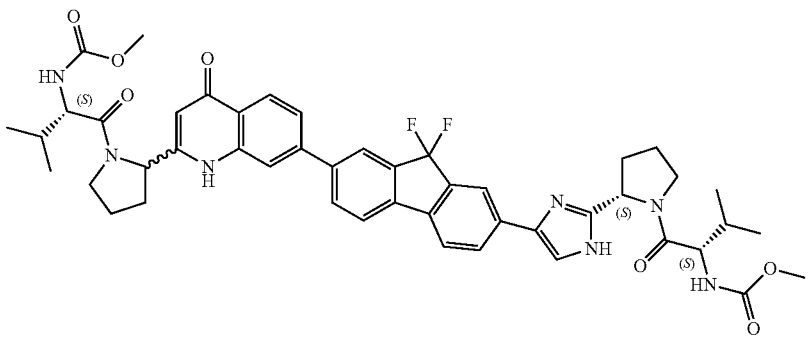 | 5 | |
| | 5a | 0.014 |
| | 5b | 0.228 |
| 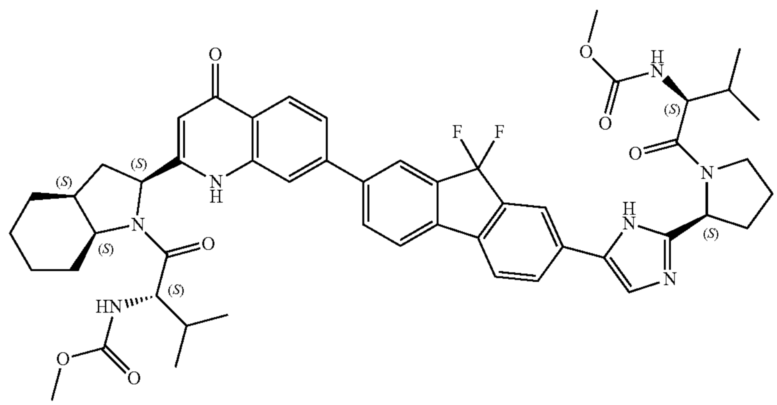 | 6 | 0.012 |
| 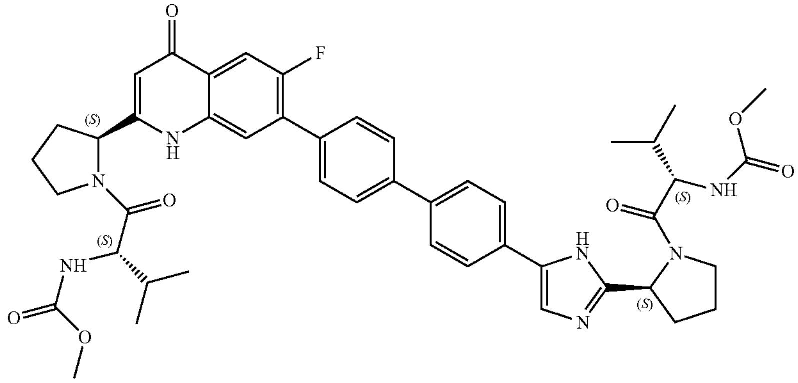 | 7 | 0.008 |

| STRUCTURE | Compound nr. | HCV-REP-HUH7LUC_EC$_{50}$ (nM) |
|---|---|---|
| 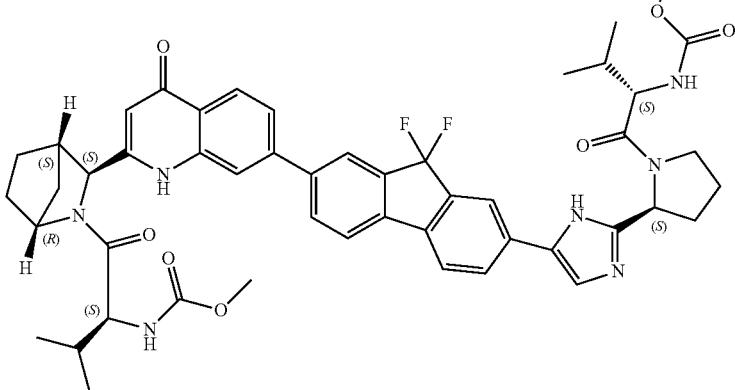 | 8 | 0.004 |
| 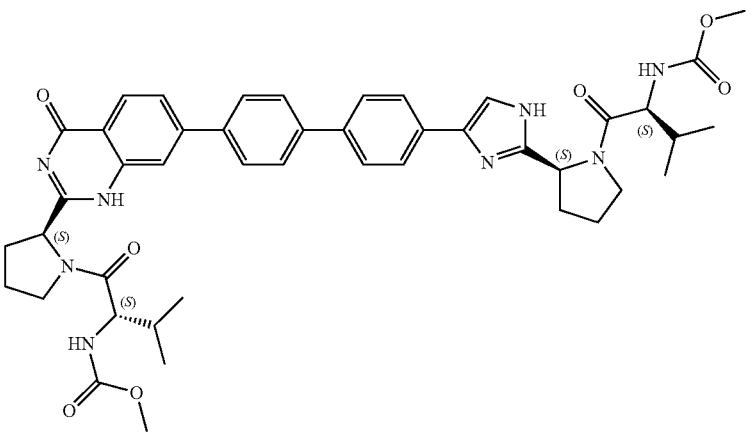 | 11 | 0.149 |
| 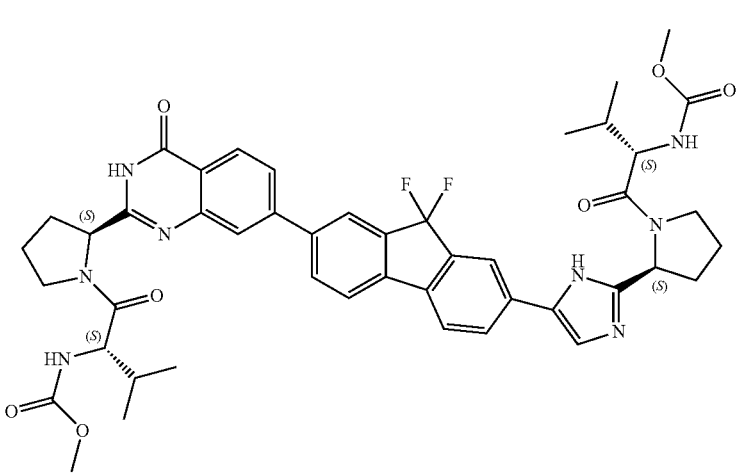 | 12 | 0.007 |

-continued

| STRUCTURE | Compound nr. | HCV-REP-HUH7LUC_EC$_{50}$ (nM) |
|---|---|---|
| 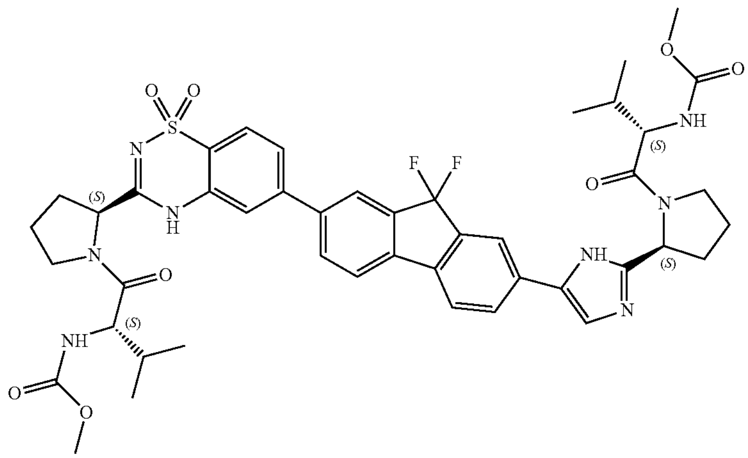 | 14 | 0.008 |
| 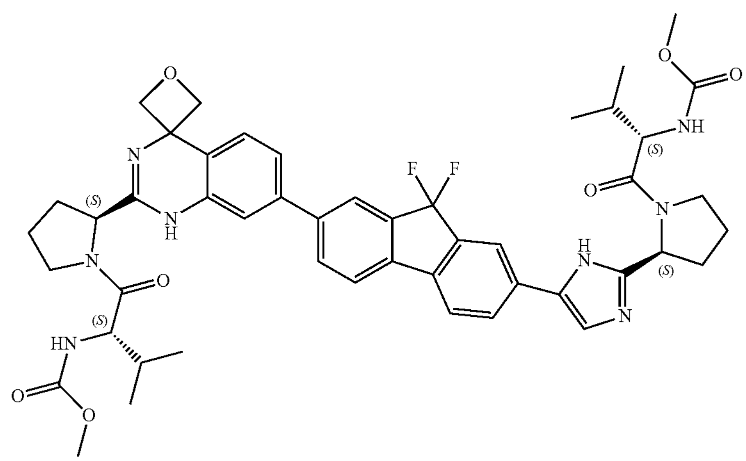 | 16 | 0.011 |
| 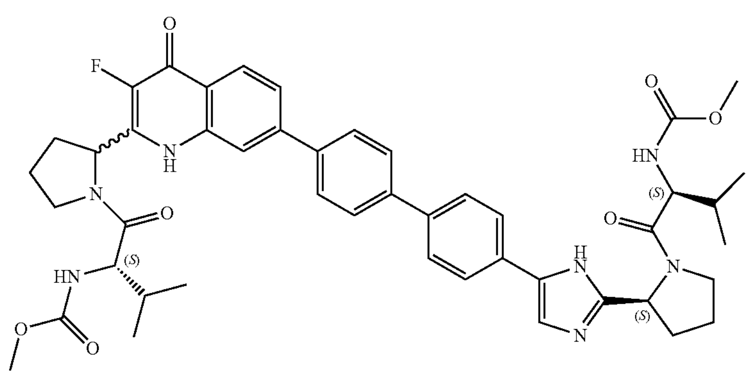 | 18 | |
| | 18a | 0.030 |
| | 18b | 4.4 |

| STRUCTURE | Compound nr. | HCV-REP-HUH7LUC_EC$_{50}$ (nM) |
|---|---|---|
| 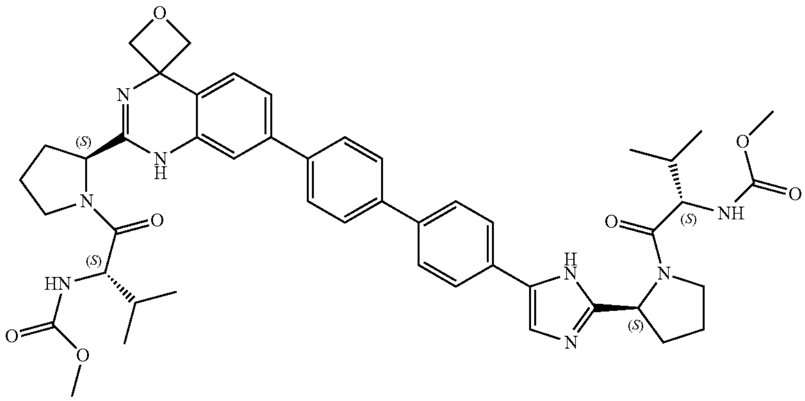 | 20 | 0.023 |
| 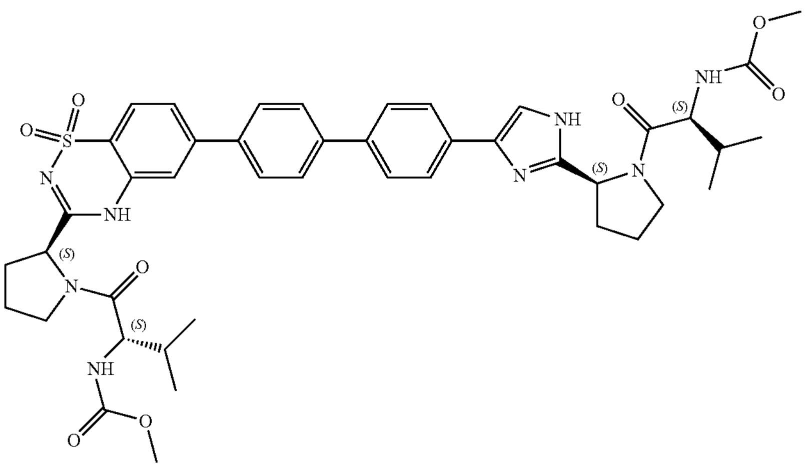 | 22 | 0.012 |
| 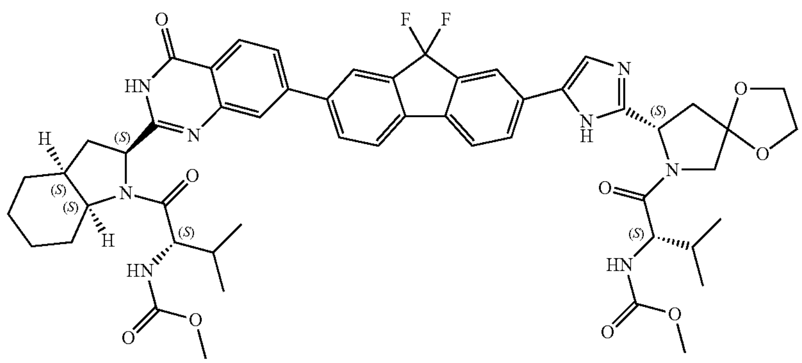 | 23 | 0.006 |

Transient Transfection

In a transient set-up, a Huh-7 lunet hepatoma cell line was transiently transfected with an autonomously replicating RNA encoding a bi-cistronic expression construct. This construct comprises a firefly luciferase reporter gene preceding the NS3-NS5B subgenomic region of HCV (genotype 1a H77 or 1b Con1). Translation of the HCV subgenomic region is mediated by an internal ribosome entry site of encephalomyocarditis virus. The construct is furthermore flanked by 5' and 3' untranslated regions of HCV (genotype 1a H77 or 1b Con 1, respectively), which allow for replication of the RNA.

Cells were plated in 384 well plates in the presence of test and control compounds, which were added in various concentrations. Following an incubation of two days, replication of the HCV subgenomic replicon RNA was measured by assaying luciferase activity (using standard luciferase assay substrates and reagents and a Perkin Elmer ViewLux™ ultraHTS microplate imager). HCV subgenomic replicon containing cells in the control cultures have high luciferase expression in the absence of any inhibitor. The inhibitory activity of the compound was monitored, enabling a dose-response curve for each test compound. EC$_{50}$ values were then calculated, which represent the amount of compound required to decrease the level of detected luciferase activity by 50%, or more specifically, to reduce the ability of the genetically linked HCV subgenomic RNA to replicate.

Counterscreens

Counterscreen cell lines included a Huh-7 hepatoma cell line containing a human cytomegalovirus major immediate-early promoter-Luc construct (Huh7-CMV-Luc) and an MT4 T-cell line containing a long terminal repeat-Luc reporter (MT4-LTR-Luc).

| Compound number | 1b EC$_{50}$ (Transient) nM | 1a EC$_{50}$ (Transient) nM | CC$_{50}$ MT4-LTR-luc (μM) | CC$_{50}$ Huh7-CMV-luc (μM) |
|---|---|---|---|---|
| 3a  | 0.025   | 0.008  | >0.984 | >0.984 |
| 3b  | 1.36    | 0.941  | >0.984 | >0.984 |
| 5a  | 0.013   | 0.007  | >0.984 | >0.984 |
| 5b  | 0.63    | 0.210  | >0.984 | >0.984 |
| 6   | 0.013   | 0.005  | >0.984 | >0.984 |
| 7   | 0.021   | 0.042  | >0.984 | >0.984 |
| 8   | 0.005   | 0.003  | 0.77   | >0.984 |
| 11  | 0.025   | 1.47   | >0.984 | >0.984 |
| 12  | 0.005   | 0.047  |        | >0.984 |
| 14  | 0.017   | 0.005  | >0.984 | >0.984 |
| 16  | 0.033   | 0.040  | >0.984 | >0.984 |
| 18a | 0.037   | 0.011  | >0.984 | >0.984 |
| 18b | 6.7     | 65.6   | >0.984 | >0.984 |
| 20  | <0.019  | 0.46   | >0.984 | >0.984 |
| 22  | 0.012   | 0.054  | >0.984 | >0.984 |
| 23  | 0.005   | 0.005  | >0.984 | >0.984 |

The invention claimed is:

1. A compound of Formula I

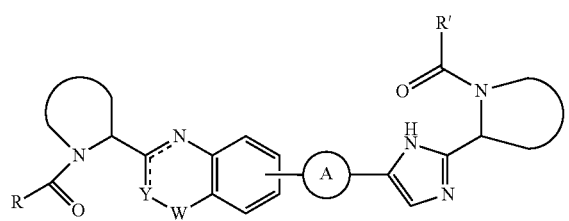

(I)

or a stereoisomer or a tautomer thereof, wherein:

Y is CH, N or CR$_4$;

W is carbonyl, sulfonyl or CR$_5$R$_6$;

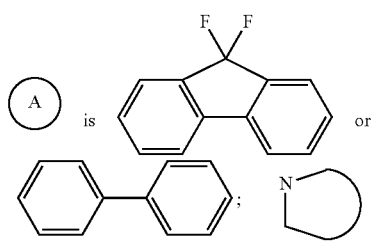

independently is selected from a group comprising

R and R' are independently selected from —CR$_1$R$_2$R$_3$, aryl optionally substituted with 1 or 2 substituents selected from halo and methyl, or heterocycloalkyl, wherein R$_1$ is selected from C$_{1-4}$alkyl, C$_{2-4}$alkyl substituted with methoxy or hydroxyl, and phenyl optionally substituted with 1 or 2 substituents independently selected from halo and methyl;

R$_2$ is hydroxyl, amino, mono- or di-C$_{1-4}$alkylamino, C$_{1-4}$alkyl-carbonylamino, C$_{1-4}$alkyloxycarbonylamino R$_3$ is hydrogen or C$_{1-4}$alkyl;

R$_4$ is hydrogen, C$_{1-4}$alkyl or Fluoro;

R$_5$ and R$_6$, each independently, are C$_{1-4}$alkyl; or

CR$_5$R$_6$ together form C$_{3-7}$cycloalkyl, oxetane, tetrahydrofurane;

or a pharmaceutically acceptable salt or a solvate thereof.

2. The compound according to claim 1, which is of formula Ia

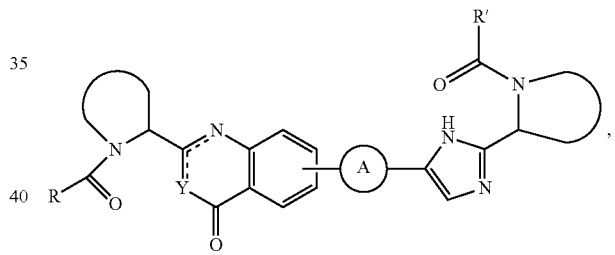

wherein A, Y, R and R' are as defined in claim 1.

3. The compound according to claim 1, which is of formula Ib

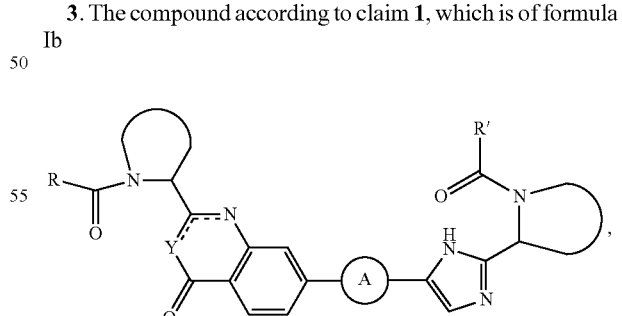

wherein A, Y, R and R' are as defined in claim 1.

4. The compound according to claim 1, which is of formula Ic

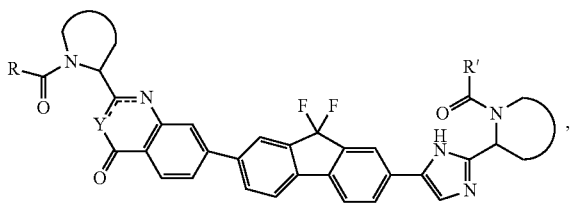

wherein Y, R and R' are as defined in claim 1.

5. The compound of claim 1, wherein each

independently is selected from a group comprising

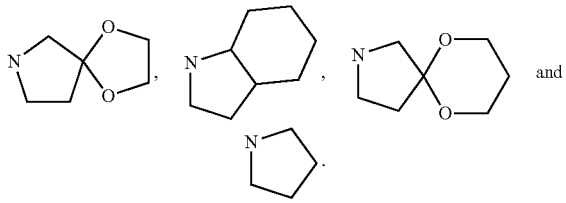 and

6. The compound according to claim 1 wherein at least one

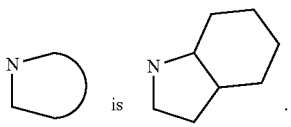 is .

7. The compound according to claim 1 wherein $R_2$ is $C_{1-4}$alkylcarbonylamino or $C_{1-4}$alkyloxycarbonylamino, and $R_3$ is hydrogen.

8. The compound according to claim 1, wherein $R_1$ is selected from branched $C_{3-4}$alkyl; $C_{2-3}$alkyl substituted with methoxy; and phenyl optionally substituted with 1 substituent selected from halo and methyl.

9. The compound according claim 1 which is of formula Id

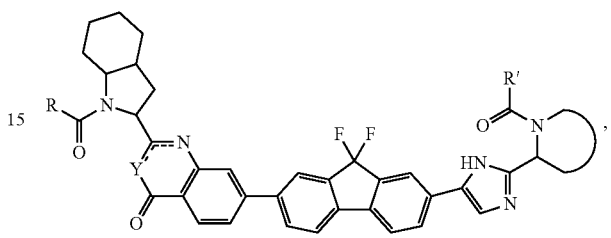

wherein Y, R and R' are as defined in claim 1.

10. A pharmaceutical composition comprising a compound according to claim 1 and a pharmaceutically acceptable carrier.

11. A method of treating an HCV infection in a mammal in need thereof, comprising administering to said mammal a therapeutically effective amount of a compound of claim 1.

12. The method of claim 11, further comprising administration of another HCV inhibitor.

13. The method of claim 12, wherein said compound of claim 1 and said another HCV inhibitor are administered simultaneously, separately or sequentially.

14. The pharmaceutical composition of claim 10, further comprising another HCV inhibitor.

* * * * *